United States Patent
Barouch et al.

(10) Patent No.: US 10,716,845 B2
(45) Date of Patent: Jul. 21, 2020

(54) STABILIZED HUMAN IMMUNODEFICIENCY VIRUS (HIV) CLADE C ENVELOPE (ENV) TRIMER VACCINES AND METHODS OF USING SAME

(71) Applicant: Beth Israel Deaconess Medical Center, Inc., Boston, MA (US)

(72) Inventors: Dan H. Barouch, Newton, MA (US); Christine Bricault, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 15/026,391

(22) PCT Filed: Oct. 3, 2014

(86) PCT No.: PCT/US2014/059093
§ 371 (c)(1),
(2) Date: Mar. 31, 2016

(87) PCT Pub. No.: WO2015/051270
PCT Pub. Date: Apr. 9, 2015

(65) Prior Publication Data
US 2016/0243215 A1    Aug. 25, 2016

Related U.S. Application Data

(60) Provisional application No. 61/886,932, filed on Oct. 4, 2013.

(51) Int. Cl.
  A61K 39/12    (2006.01)
  A61K 39/21    (2006.01)
  C07K 14/16    (2006.01)
  C12N 7/00     (2006.01)
  A61K 39/00    (2006.01)

(52) U.S. Cl.
  CPC ............. *A61K 39/21* (2013.01); *A61K 39/12* (2013.01); *C07K 14/162* (2013.01); *C12N 7/00* (2013.01); *A61K 2039/545* (2013.01); *A61K 2039/55561* (2013.01); *A61K 2039/55566* (2013.01); *A61K 2039/575* (2013.01); *A61K 2039/70* (2013.01); *C07K 2319/00* (2013.01); *C12N 2740/15034* (2013.01); *C12N 2740/16022* (2013.01); *C12N 2740/16034* (2013.01); *C12N 2740/16071* (2013.01); *C12N 2740/16111* (2013.01); *C12N 2740/16122* (2013.01); *C12N 2740/16134* (2013.01); *C12N 2740/16171* (2013.01)

(58) Field of Classification Search
  CPC ....... A61K 39/12; C12N 7/00; C12N 2740/16134; C12N 2740/16122; C07K 2319/00
See application file for complete search history.

(56) References Cited

U.S. PATENT DOCUMENTS

| | | |
|---|---|---|
| 4,603,112 A | 7/1986 | Paoletti et al. |
| 5,639,649 A | 6/1997 | Almond et al. |
| 5,643,576 A | 7/1997 | Johnston et al. |
| 7,592,014 B2 | 9/2009 | Binley et al. |
| 7,939,083 B2 | 5/2011 | Dey et al. |
| 9,017,691 B2 | 4/2015 | Barouch et al. |
| 2005/0232900 A1 | 10/2005 | Vogels et al. |
| 2007/0298051 A1 | 12/2007 | Barouch et al. |
| 2011/0250220 A1 | 10/2011 | Dey et al. |
| 2011/0305749 A1 | 12/2011 | Duch et al. |
| 2012/0045472 A1 | 2/2012 | Harrison et al. |
| 2013/0189754 A1 | 7/2013 | Parks et al. |
| 2014/0302080 A1 | 10/2014 | Barouch et al. |
| 2014/0335126 A1 | 11/2014 | Haynes et al. |
| 2014/0348791 A1 | 11/2014 | Barouch et al. |
| 2015/0291935 A1 | 10/2015 | Barouch et al. |

FOREIGN PATENT DOCUMENTS

| | | |
|---|---|---|
| AU | 2013204885 A1 | 5/2013 |
| WO | WO-2004/044155 A2 | 5/2004 |
| WO | WO-2006/040330 A2 | 4/2006 |
| WO | WO-2007/024941 A2 | 3/2007 |
| WO | WO-2007/104792 A2 | 9/2007 |
| WO | WO-2007/149491 A2 | 12/2007 |
| WO | WO-2010/042942 A2 | 4/2010 |
| WO | WO-2010/059732 A1 | 5/2010 |
| WO | WO-2012/030904 A2 | 3/2012 |
| WO | WO-2013/055908 A1 | 4/2013 |
| WO | WO-2014/047261 A1 | 3/2014 |
| WO | WO-2015/048770 A2 | 4/2015 |
| WO | WO-2016/037154 A1 | 3/2016 |

OTHER PUBLICATIONS

Lynch, R. M. et al., Jan. 2011, The B cell response is redundant and highly focused on V1V2 during early subtype C infection in Zambian seroconverter, J. Virol. 85(2):905-915.*
Huang, W., et al., Jun. 2008, Coreceptor tropism can be influenced by amino acid substitutions in the gp41 transmembrane subunit of human immunodeficiency virus type 1 envelope protien, J. Virol. 82(11):5584-5593.*
Barouch, D. H., Oct. 2008, Challenges in the development of an HIV-1 vaccine, Nature 455:613-619.*
Walker, B. D., and D. R. Burton, May 2008, Toward an AIDS vaccine, Science 320:760-764.*
Kwong, P. D., et al., 2011, Rational design of vaccines to elicit broadly neutralizing antibodies to HIV-1, Cold Spring Harb. Perspect. Med. 1:a007278 (1-16).*
Lewis, G. K., et al., Nov. 2014, Antibody persistence and T-cell balance: Two key factors confronting HIV vaccine development, Proc. Natl. Acad. Sci. 111(44): 15614-15621.*

(Continued)

*Primary Examiner* — Jeffrey S Parkin
(74) *Attorney, Agent, or Firm* — Clark & Elbing LLP

(57) ABSTRACT

The invention features stabilized human immunodeficiency virus (H IV) clade C envelope (Env) trimers. The invention also features vaccines, nucleic acids, and vectors to deliver and/or facilitate production of the stabilized HIV clade C Env trimers. In addition, the invention features methods of making and using the stabilized HIV clade C Env trimers of the invention.

18 Claims, 24 Drawing Sheets

Specification includes a Sequence Listing.

(56) References Cited

OTHER PUBLICATIONS

West, Jr., A. P., et al., Feb. 2014, Structural insights on the role of antibodies in HIV-1 vaccine and therapy, Cell 156:633-648.*

Zolla-Pazner, S., 2014, A critical question for HIV vaccine development: Which antibodies to induce? Science 345:167-169.*

Weng, Y., and C. D. Weiss, Dec. 1998, Mutational Analysis of Residues in the Coiled-Coil Domain of Human Immunodeficiency Virus Type 1 Transmembrane Protein gp41, J. Virol. 72(12):9676-9682.*

Mayr, L. M., et al., Jul. 2013, Epitope Mapping of Conformational V2-specific Anti-HIV Human Monoclonal Antibodies Reveals an Immunodominant Site in V2, PLOS ONE 8(7):e70859 (pp. 1-9).*

Diaz-Aguilar, B., et al., 2013, Significant Differences in Cell-Cell Fusion and Viral Entry between Strains Revealed by Scanning Mutagenesis of the C-Heptad Repeat of HIV gp41, Biochem. 52:3552-3563.*

Abrahams et al., "Quantitating the multiplicity of infection with human immunodeficiency virus type 1 subtype C reveals a non-poisson distribution of transmitted variants," J Virol. 83(8):3556-67 (2009).

Amanna et al., "Contributions of humoral and cellular immunity to vaccine-induced protection in humans," Virology. 411(2):206-15 (2011).

Baba et al., "Human neutralizing monoclonal antibodies of the IgG1 subtype protect against mucosal simian-human immunodeficiency virus infection," Nat Med. 6(2):200-6 (2000).

"Mosaic HIV-1 vaccines expand the breadth and depth of cellular immune responses in rhesus monkeys," available in PMC Sep. 1, 2010, published in final edited form as: Nat Med. 16(3):319-23 (2010) (14 pages).

"Efficacy assessment of a cell-mediated immunity HIV-1 vaccine (the Step Study): a double-blind, randomised, placebo-controlled, test-of-concept trial," available in PMC Nov. 29, 2009, published in final edited form as: Lancet. 372(9653):1881-93 (2008) (25 pages).

Burke et al., "Neutralizing antibody responses to subtype B and C adjuvanted HIV envelope protein vaccination in rabbits," Virology. 387(1):147-56 (2009).

Calarese et al., "Antibody domain exchange is an immunological solution to carbohydrate cluster recognition," Science. 300(5628):2065-71 (2003).

Cardoso et al., "Broadly neutralizing anti-HIV antibody 4E10 recognizes a helical conformation of a highly conserved fusion-associated motif in gp41," Immunity. 22(2):163-73 (2005).

Cardoso et al., "Structural basis of enhanced binding of extended and helically constrained peptide epitopes of the broadly neutralizing HIV-1 antibody 4E10," J Mol Biol. 365(5):1533-44 (2007).

Catanzaro et al., "Phase I clinical evaluation of a six-plasmid multiclade HIV-1 DNA candidate vaccine," Vaccine. 25(20):4085-92 (2007).

"HIV-1 Envelope Glycoprotein Biosynthesis, Trafficking, and Incorporation," available in PMC Jul. 22, 2012, published in final edited form as: J Mol Biol. 410(4):582-608 (2011) (40 pages).

Chen et al., "A chimeric protein of simian immunodeficiency virus envelope glycoprotein gp140 and *Escherichia coli* aspartate transcarbamoylase," J Virol. 78(9):4508-16 (2004).

Cho et al., "Polyvalent envelope glycoprotein vaccine elicits a broader neutralizing antibody response but is unable to provide sterilizing protection against heterologous Simian/human immunodeficiency virus infection in pigtailed macaques," J Virol. 75(5):2224-34 (2001).

Cohen, "Naked DNA points way to vaccines," Science. 259(5102):1691-2 (1993).

Davenport et al., "Binding interactions between soluble HIV envelope glycoproteins and quaternary-structure-specific monoclonal antibodies PG9 and PG16," J Virol. 85(14):7095-107 (2011).

Doores et al., "Antibody 2G12 recognizes di-mannose equivalently in domain- and nondomain-exchanged forms but only binds the HIV-1 glycan shield if domain exchanged," J Virol. 84(20):10690-9 (2010).

Doria-Rose et al., "Frequency and phenotype of human immunodeficiency virus envelope-specific B cells from patients with broadly cross-neutralizing antibodies," J Virol. 83(1):188-99 (2009).

Engelhardt et al., "Ablation of E2A in recombinant adenoviruses improves transgene persistence and decreases inflammatory response in mouse liver," Proc Natl Acad Sci U.S.A. 91(13):6196-200 (1994).

Falkowska et al., "PGV04, an HIV-1 gp120 CD4 binding site antibody, is broad and potent in neutralization but does not induce conformational changes characteristic of CD4," J Virol. 86(8):4394-403 (2012).

Fiebig et al., "Neutralizing antibodies against conserved domains of p15E of porcine endogenous retroviruses: basis for a vaccine for xenotransplantation?" Virology. 307(2):406-13 (2003).

Fischer et al., "Identification of a peptide mimicking the binding pattern of an antiphospholipid antibody," Immunobiology. 211(9):695-99 (2006).

Fischer et al., "Polyvalent vaccines for optimal coverage of potential T-cell epitopes in global HIV-1 variants," Nat Med. 13(1):100-6 (2007).

Freeman et al., "Crystal structure of HIV-1 primary receptor CD4 in complex with a potent antiviral antibody," Structure. 18(12):1632-41 (2010).

Frey et al., "A fusion-intermediate state of HIV-1 gp41 targeted by broadly neutralizing antibodies," Proc Natl Acad Sci U.S.A. 105(10):3739-44 (2008).

Fynan et al., "Dna vaccines: protective immunizations by parenteral, mucosal, and gene-gun inoculations," Proc Natl Acad Sci U.S.A. 90(24):11478-82 (1993).

Gao et al., "Antigenicity and immunogenicity of a synthetic human immunodeficiency virus type 1 group m consensus envelope glycoprotein," J Virol. 79(2):1154-63 (2005).

Gao et al., "Centralized HIV-1 envelope immunogens and neutralizing antibodies," Curr HIV Res. 5(6):572-7 (2007).

Gao et al., "Molecular cloning and analysis of functional envelope genes from human immunodeficiency virus type 1 sequence subtypes A through G," J Virol. 70(3):1651-67 (1996).

Gaschen et al., "Diversity consideration in HIV-1 vaccine selection," Science. 296(5577):2354-60 (2002).

GenBank Accession No. KC769514. Retrieved on Dec. 30, 2014 (2 pages).

Georgiev et al., "Delineating antibody recognition in polyclonal sera from patterns of HIV-1 isolate neutralization," Science. 340(6133):751-6 (2013).

Graham et al., "Phase 1 safety and immunogenicity evaluation of a multiclade HIV-1 DNA candidate vaccine," J Infect Dis. 194(12):1650-60 (2006).

Gray et al., "Isolation of a monoclonal antibody that targets the alpha-2 helix of gp120 and represents the initial autologous neutralizing-antibody response in an HIV-1 subtype C-infected individual," J Virol. 85(15):7719-29 (2011).

"Safety and efficacy of the HVTN 503/Phambili study: a double-blind randomized placebo-controlled test-of-concept study of a clade b-based HIV-1 vaccine in south africa," available in PMC Aug. 13, 2012, published in final edited form as: Lancet Infect Dis. 11(7):507-15 (2011) (19 pages).

Grundner et al., "Analysis of the neutralizing antibody response elicited in rabbits by repeated inoculation with trimeric HIV-1 envelope glycoproteins," Virology. 331(1):33-46 (2005).

Hammer et al., "Efficacy trial of a DNA/rAd5 HIV-1 preventive vaccine," N Engl J Med. 369(22):2083-92 (2013).

Haynes et al., "Immune-correlates analysis of an HIV-1 vaccine efficacy trial," N Engl J Med. 366(14):1275-86 (2012).

Huang et al., "Broad and potent neutralization of HIV-1 by a gp41-specific human antibody," Nature. 491(7424):406-12 (2012).

International Preliminary Report on Patentability for International Patent Application No. PCT/US2014/059093, dated Apr. 5, 2016 (7 pages).

International Search Report and Written Opinion for International Patent Application No. PCT/US2014/059093, dated Jan. 22, 2015 (12 pages).

Julien et al., "Asymmetric recognition of the HIV-1 trimer by broadly neutralizing antibody PG9," Proc Natl Acad Sci USA. 110(11):4351-6 (2013).

(56) References Cited

OTHER PUBLICATIONS

Julien et al., "Broadly neutralizing antibody PGT121 allosterically modulates CD4 binding via recognition of the HIV-1 gp120 V3 base and multiple surrounding glycans," PLoS Pathog. 9(5):e1003342 (2013) (15 pages).
Kim et al., "Comparison of HIV Type 1 ADA gp120 monomers versus gp140 trimers as immunogens for the induction of neutralizing antibodies," Aids Res Hum Retroviruses. 21(1):58-67 (2005).
Kochanek et al., "A new adenoviral vector: Replacement of all viral coding sequences with 28 kb of DNA independently expressing both full-length dystrophin and beta-galactosidase," Proc Natl Acad Sci U.S.A. 93(12):5731-6 (1996).
Kothe et al., "Ancestral and consensus envelope immunogens for HIV-1 subtype C," Virology. 352(2):438-49 (2006).
"Antigenicity and immunogenicity of HIV-1 consensus subtype B envelope glycoproteins," available in PMC Mar. 30, 2008, published in final edited form as: Virology. 360(1):218-34 (2007) (29 pages).
Kovacs et al., "HIV-1 envelope trimer elicits more potent neutralizing antibody responses than monomeric gp120," Proc Natl Acad Sci USA. 109(30):12111-6 (2012).
Kwong et al., "Structure of an HIV gp120 envelope glycoprotein in complex with the CD4 receptor and a neutralizing human antibody," Nature. 393(6686):648-59 (1998).
"Broad HIV-1 neutralization mediated by CD4-binding site antibodies," available in PMC Nov. 19, 2008, published in final edited form as: Nat Med. 13(9):1032-4 (2007) (7 pages).
Li et al., "Characterization of antibody responses elicited by human immunodeficiency virus type 1 primary isolate trimeric and monomeric envelope glycoproteins in selected adjuvants," J Virol. 80(3):1414-26 (2006).
Li et al., "Evidence for potent autologous neutralizing antibody titers and compact envelopes in early infection with subtype C human immunodeficiency virus type 1," J Virol. 80(11):5211-8 (2006).
Li et al., "Human immunodeficiency virus type 1 env clones from acute and early subtype B infections for standardized assessments of vaccine-elicited neutralizing antibodies," J Virol. 79(16):10108-25 (2005).
Li et al., "Removal of a single N-linked glycan in human immunodeficiency virus type 1 gp120 results in an enhanced ability to induce neutralizing antibody responses," J Virol. 82(2):638-51 (2008).
"A group M consensus envelope glycoprotein induces antibodies that neutralize subsets of subtype B and C HIV-1 primary viruses," available in PMC Sep. 30, 2007, published in final edited form as: Virology. 353(2):268-82 (2006) (30 pages).
Liao et al., "Antigenicity and immunogenicity of transmitted/founder, consensus, and chronic envelope glycoproteins of human immunodeficiency virus type 1," J Virol. 87(8):4185-201 (2013).
"Co-evolution of a broadly neutralizing HIV-1 antibody and founder virus," available in PMC Oct. 25, 2013, published in final edited form as: Nature. 496(7446):469-76 (2013) (25 pages).
Lin et al., "Designing immunogens to elicit broadly neutralizing antibodies to the HIV-1 envelope glycoprotein," Curr HIV Res. 5(6):514-41 (2007).
Lynch et al., "The development of CD4 binding site antibodies during HIV-1 infection," J Virol. 86(14):7588-95 (2012).
Malherbe et al., "Sequential immunization with a subtype B HIV-1 envelope quasispecies partially mimics the in vivo development of neutralizing antibodies," J Virol. 85(11):5262-74 (2011).
Mangeat et al., "Lentiviral vectors and antiretroviral intrinsic immunity," Hum Gene Ther. 16(8):913-20 (2005).
Mascola et al., "Protection of Macaques against pathogenic simian/human immunodeficiency virus 89.6PD by passive transfer of neutralizing antibodies," J Virol. 73(5):4009-18 (1999).
Mascola et al., "Protection of macaques against vaginal transmission of a pathogenic HIV-1/SIV chimeric virus by passive infusion of neutralizing antibodies," Nat Med. 6(2):207-10 (2000).

McBurney et al., "Evaluation of heterologous vaginal SHIV SF162p4 infection following vaccination with a polyvalent Clade B virus-like particle vaccine," AIDS Res Hum Retroviruses. 28(9):863-72 (2012).
McBurney et al., "Human immunodeficiency virus-like particles with consensus envelopes elicited broader cell-mediated peripheral and mucosal immune responses than polyvalent and monovalent Env vaccines," Vaccine. 27(32):4337-49 (2009).
McCoy et al., "Potent and broad neutralization of HIV-1 by a llama antibody elicited by immunization," J Exp Med. 209(6):1091-103 (2012).
McGuire et al., "Engineering HIV envelope protein to activate germline B cell receptors of broadly neutralizing anti-CD4 binding site antibodies," J Exp Med. 210(4):655-63 (2013).
Pancera et al., "Crystal structure of PG16 and chimeric dissection with somatically related PG9: structure-function analysis of two quaternary-specific antibodies that effectively neutralize HIV-1," J Virol. 84(16):8098-110 (2010).
"Structure of HIV-1 gp120 V1/V2 domain with broadly neutralizing antibody PG9," available in PMC Dec. 15, 2012, published in final edited form as: Nature. 480(7377):336-43 (2011) (17 pages).
Montefiori, "Evaluating neutralizing antibodies against HIV, SIV, and SHIV in luciferase reporter gene assays," Curr Protoc Immunol. 12:Unit 12.11 (2005) (17 pages).
Mouquet et al., "Complex-type N-glycan recognition by potent broadly neutralizing HIV antibodies," Proc Natl Acad Sci U.S.A. 109(47):E3268-77 (2012).
Nkolola et al., "Characterization and immunogenicity of a novel mosaic M HIV-1 gp140 trimer," J Virol. 88(17):9538-52 (2014).
Ofek et al., "Structure and mechanistic analysis of the anti-human immunodeficiency virus type 1 antibody 2F5 in complex with its gp41 epitope," J Virol. 78(19):10724-37 (2004).
Pancera et al., "Structure of HIV-1 gp120 with gp41-interactive region reveals layered envelope architecture and basis of conformational mobility," Proc Natl Acad Sci USA. 107(3):1166-71 (2010).
Pejchal et al., "A potent and broad neutralizing antibody recognizes and penetrates the HIV glycan shield," Science. 334(6059):1097-103 (2011).
Pejchal et al., "Structure and function of broadly reactive antibody PG16 reveal an H3 subdomain that mediates potent neutralization of HIV-1," Proc Natl Acad Sci USA. 107(25):11483-8 (2010).
Pinter, "Roles of HIV-1 Env variable regions in viral neutralization and vaccine development," Curr HIV Res. 5(6):542-53 (2007).
Plotkin et al., "Postscript relating to new allegations made by Edward Hooper at the Royal Society Discussion Meeting on Sep. 11, 2000," Philos Trans R Soc Lond B Biol Sci. 356(1410):825-9 (2001).
Plotkin, "Correlates of Protection Induced by Vaccination," Clin Vaccine Immunol. 17(7):1055-65 (2010).
Plotkin, "Immunologic correlates of protection induced by vaccination," Pediatr Infect Dis J. 20(1):63-75 (2001).
Plotkin, "The RV144 Thai HIV vaccine trial," Hum Vaccin. 6(2):159 (2010).
Rerks-Ngarm et al., "Vaccination with ALVAC and AIDSVAX to prevent HIV-1 infection in Thailand," N Engl J Med. 361(23):2209-20 (2009).
Rodenburg et al., "Near full-length clones and reference sequences for subtype C isolates of HIV type 1 from three different continents," AIDS Res Hum Retrovirsuses. 17(2):161-8 (2001).
"Mosaic vaccines elicit CD8+ T lymphocyte responses in monkeys that confer enhanced immune coverage of diverse HIV strains," available in PMC Sep. 1, 2010, published in final edited form as: Nat Med. 16(3):324-8 (2010) (12 pages).
Saphire et al., "Crystal structure of a neutralizing human IgG against HIV-1: a template for vaccine design," Science. 293(5532):1155-9 (2001).
Scheid et al., "Sequence and structural convergence of broad and potent HIV antibodies that mimic CD4 binding," Science. 333(6049):1633-7 (2011).
Seaman et al., "Multiclade human immunodeficiency virus type 1 envelope immunogens elicit broad cellular and humoral immunity in rhesus monkeys," J Virol. 79(5):2956-63 (2005).

(56) References Cited

OTHER PUBLICATIONS

Seaman et al., "Standardized assessment of NAb responses elicited in rhesus monkeys immunized with single- or multi-clade HIV-1 envelope immunogens," Virology. 367(1):175-86 (2007).
Simek et al., "Human immunodeficiency virus type 1 elite neutralizers: individuals with broad and potent neutralizing activity identified by using a high-throughput neutralization assay together with an analytical selection algorithm," J Virol. 83(14):7337-48 (2009).
Sok et al., "Promiscuous glycan site recognition by antibodies to the high-mannose patch of gp120 broadens neutralization of HIV," Sci Transl Med. 6(236):236ra63 (2014) (13 pages).
Stamatatos et al., "Neutralizing antibodies generated during natural HIV-1 infection: good news for an HIV-1 vaccine?," Nat Med. 15(8):866-70 (2009).
"Antibody responses elicited through homologous or heterologous prime-boost DNA and protein vaccinations differ in functional activity and avidity," available in PMC Apr. 9, 2011, published in final edited form as: Vaccine. 28(17):2999-3007 (2010) (21 pages).
Vaine et al., "Profiles of human serum antibody responses elicited by three leading HIV vaccines focusing on the induction of Env-specific antibodies," PLoS One. 5(11):e13916 (2010) (8 pages).
Walker et al., "Broad and potent neutralizing antibodies from an African donor reveal a new HIV-1 vaccine target," Science. 326(5950):285-9 (2009).
"Broad neutralization coverage of HIV by multiple highly potent antibodies," available in PMC Jul. 10, 2012, published in final edited form as: Nature. 477(7365):466-70 (2011) (14 pages).
"Cross-subtype antibody and cellular immune responses induced by a polyvalent DNA prime-protein boost HIV-1 vaccine in healthy human volunteers," available in PMC Aug. 14, 2013, published in final edited form as: Vaccine. 26(31):3947-57 (2008) (22 pages).
Wang et al., "Enhanced immunogenicity of gp120 protein when combined with recombinant DNA priming to generate antibodies that neutralize the JR-FL primary isolate of human immunodeficiency virus type 1," J Virol. 79(12):7933-7 (2005).
Wang et al., "Polyvalent HIV-1 Env vaccine formulations delivered by the DNA priming plus protein boosting approach are effective in generating neutralizing antibodies against primary human immunodeficiency virus type 1 isolates from subtypes A, B, C, D and E," Virology. 350(1):34-47 (2006).
Wattanapitayakul et al., "Recent developments in gene therapy for cardiac disease," Biomed Pharmacother. 54(10):487-504 (2000).
Wiznerowicz et al., "Harnessing HIV for therapy, basic research and biotechnology," 23(1):42-7 (2005).
Wu et al., "Rational design of envelope identifies broadly neutralizing human monoclonal antibodies to HIV-1," Science. 329(5993):856-61 (2010).
Yang et al., "Highly stable trimers formed by human immunodeficiency virus type 1 envelope glycoproteins fused with the trimeric motif of t4 bacteriophage fibritin," J Virol. 76(9):4634-42 (2002).
Yang et al., "Improved elicitation of neutralizing antibodies against primary human immunodeficiency viruses by soluble stabilized envelope glycoprotein trimers," J Virol. 75(3):1165-71 (2001).
Yasmeen et al., "Differential binding of neutralizing and non-neutralizing antibodies to native-like soluble HIV-1 Env trimers, uncleaved Env proteins, and monomeric subunits," Retrovirology. 11:41 (2014) (17 pages).
"Structural basis for broad and potent neutralization of HIV-1 by antibody VRC01," available in PMC Aug. 13, 2011, published in final edited format as: Science. 329(5993):811-7 (2010) (19 pages).
Nkolola et al., "Breadth of neutralizing antibodies elicited by stable, homogeneous clade A and clade C HIV-1 gp140 envelope trimers in guinea pigs," J Virol. 84(7):3270-9 (2010).
International Search Report for International Application No. PCT/US2014/010543 dated Mar. 21, 2014 (5 pages).
Written Opinion of the International Searching Authority for International Application No. PCT/US2014/010543 dated Mar. 21, 2014 (6 pages).
International Preliminary Report on Patentability for International Application No. PCT/US2014/010543, dated Mar. 21, 2014 (7 pages).
Lee et al., "A single point mutation in HIV-1 V3 loop alters the immunogenic properties of rgp120," Arch Virol. 145(10):2087-103 (2000).
Watkins et al., "Immune escape by human immunodeficiency virus type 1 from neutralizing antibodies: evidence for multiple pathways," J Virol. 67(12):7493-500 (1993).
Walker et al., "Toward an AIDS vaccine," Science 320(5877):760-4 (2008).
McElrath et al., "Induction of immunity to human immunodeficiency virus type-1 by vaccination," Immunity 33(4):542-54 (2010).
Jeffs et al., "Expression and characterisation of recombinant oligomeric envelope glycoproteins derived from primary isolates of HIV-1," Vaccine. 22(8):1032-46 (2004).
Chen et al., "Expression, purification, and characterization of gp160e, the soluble, trimeric ectodomain of the simian immunodeficiency virus envelope glycoprotein, gp160," J Biol Chem. 275(45):34946-53 (2000).
English Translation of Notice Before Examination for Israeli Patent Application No. 239805, (2 pages).
English Translation of Office Action for Israeli Patent Application No. 239805, (2 pages).
Search Report and Written Opinion for Singaporean Patent Application No. 11201505229X, dated May 5, 2016 (9 pages).
Extended European Search Report for European Patent Application No. 14735323.9, dated Aug. 16, 2016 (9 pages).
Bricault et al., "A multivalent clade C HIV-1 Env trimer cocktail elicits a higher magnitude of neutralizing antibodies than any individual component," J Virol. 89(5):2507-19 (2015).
Extended European Search Report for European Patent Application No. 14851250.2, dated Apr. 11, 2017 (5 pages).
Du et al., "Effect of trimerization motifs on quaternary structure, antigenicity, and immunogenicity on a noncleavable HIV-1 gp140 envelope glycoprotein," Virol. 395(1):33-44 (2009).
Communication pursuant to Article 94(3) EPC for European Patent Application No. 14851250.2, dated Dec. 4, 2017 (5 pages).
Merk et al., "HIV-1 envelope glycoprotein structure," available in PMC Apr. 18, 2014, published in final edited form as: Curr Opin Struct Biol. 23(2):268-76 (2013) (16 pages).
Pancera et al., "Structure and immune recognition of trimeric prefusion HIV-1 Env," Nature 514(7523):455-61 (2014).
Kwon et al., "Crystal structure, conformational fixation, and entry-related interactions of mature ligand-free HIV-1 Env," Nat. Struc. Mol. Biol. 22(7):522-31 (2015).
Abbink et al., "Comparative seroprevalence and immunogenicity of six rare serotype recombinant adenovirus vaccine vectors from subgroups B and D," J Virol. 81(9):4654-63 (2007).
Barouch et al., "Immunogenicity of recombinant adenovirus serotype 35 vaccine in the presence of pre-existing anti-Ad5 immunity," J Immunol. 172(10):6290-7 (2004) (9 pages).
Barouch et al., "International seroepidemiology of adenovirus serotypes 5, 26, 35, and 48 in pediatric and adult populations," Vaccine. 29(32):5203-9 (2011) (14 pages).
International Search Report and Written Opinion for International Application No. PCT/US17/57045, dated Feb. 28, 2018 (17 pages).
Liu et al., "Modulation of DNA vaccine-elicited CD8+ T-lymphocyte epitope immunodominance hierarchies," J Virol. 80(24):11991-7 (2006).
Sumida et al., "Neutralizing antibodies to adenovirus serotype 5 vaccine vectors are directed primarily against the adenovirus hexon protein," J Immunol. 174(11):7179-85 (2005).
Wang et al., "Improved expression of secretory and trimeric proteins in mammalian cells via the introduction of a new trimer motif and a mutant of the tPA signal sequence," Appl Microbiol Biotechnol. 91(3):731-40 (2011).
Communication pursuant to Article 94(3) EPC for European Patent Application No. 14851250.2, dated Aug. 29, 2018 (4 pages).

\* cited by examiner

FIGS. 14A – 14C
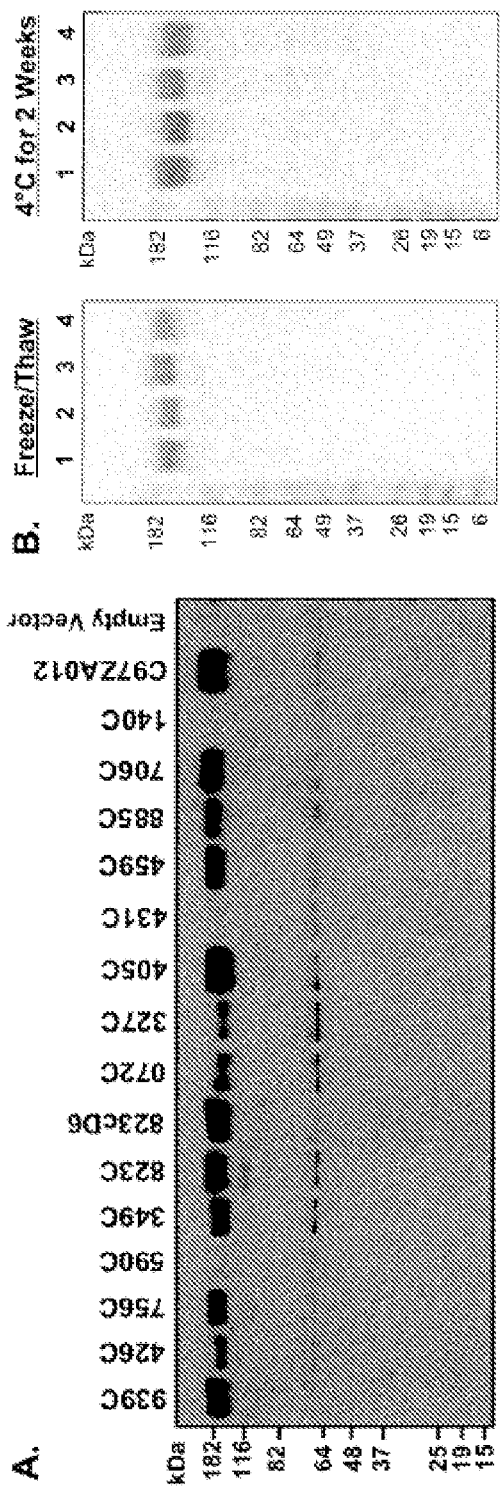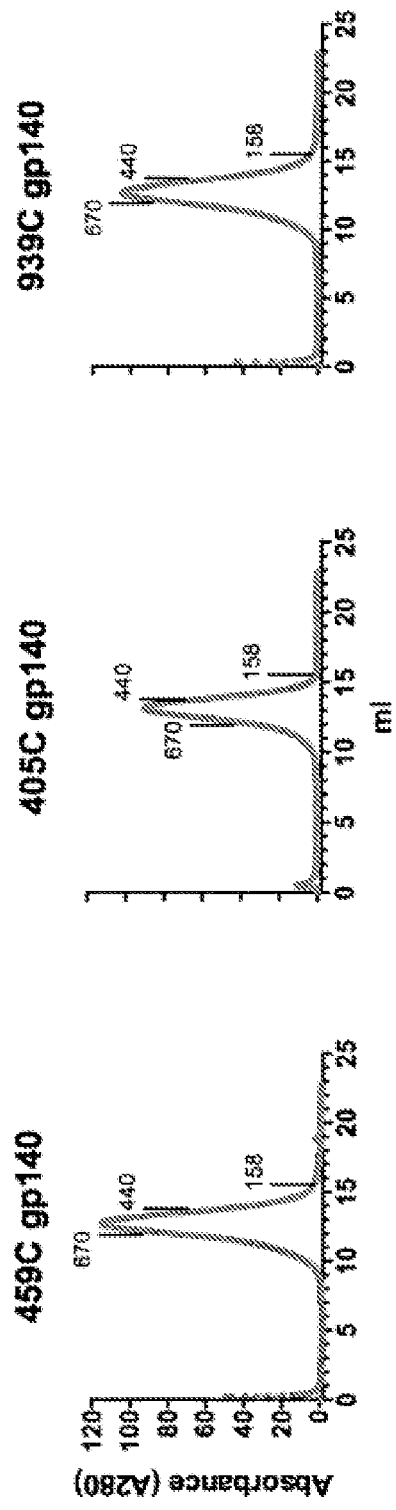

FIGS. 21A – 21C
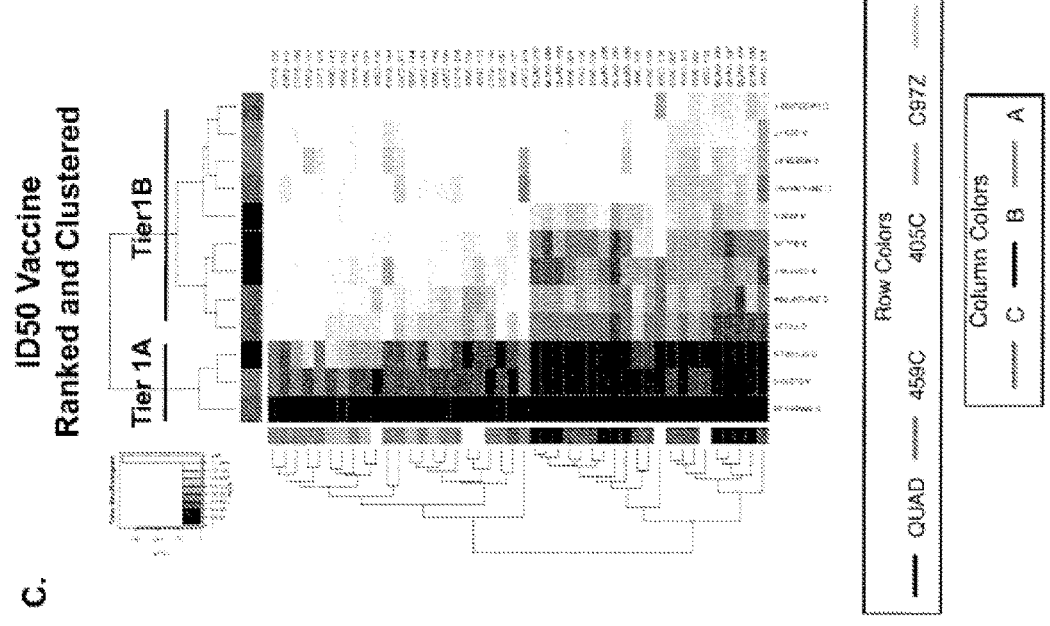
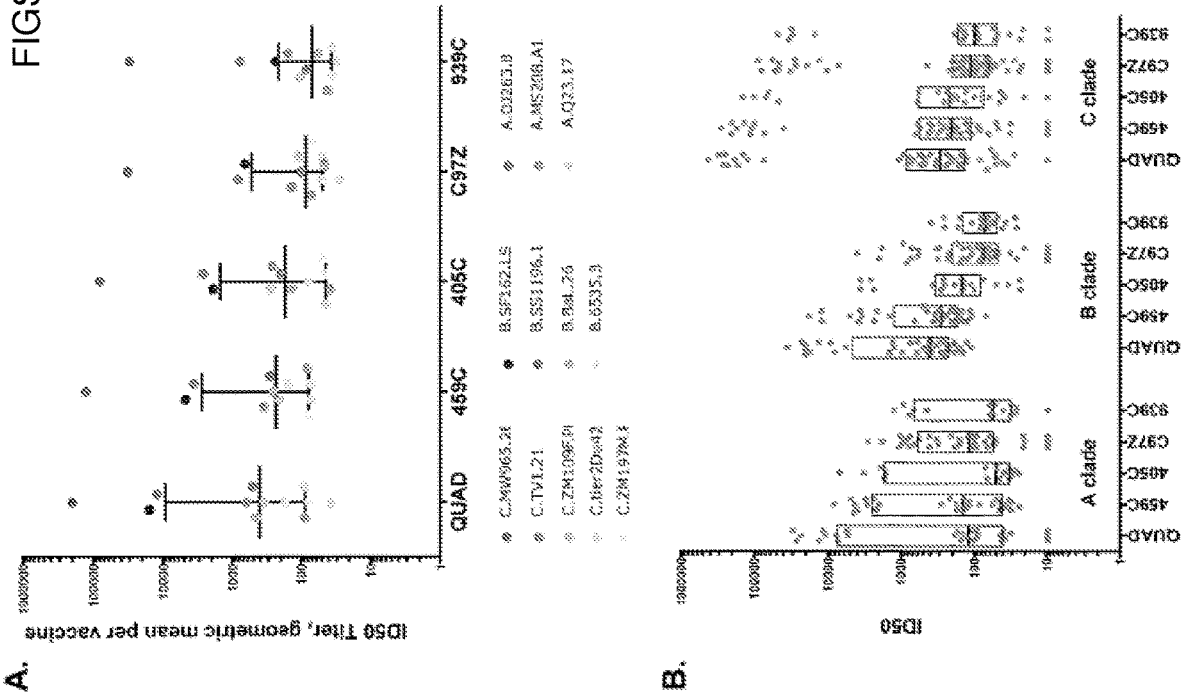

SEQUENCE LISTING

<160> NUMBER OF SEQ ID NOS: 8

<210> SEQ ID NO 1
<211> LENGTH: 728
<212> TYPE: PRT
<213> ORGANISM: Artificial Sequence
<220> FEATURE:
<223> OTHER INFORMATION: Synthetic Construct

<400> SEQUENCE: 1

```
Met Arg Val Arg Gly Ile Gln Arg Asn Cys Gln His Leu Trp Arg Trp
1               5                   10                  15
Gly Thr Leu Ile Leu Gly Met Leu Met Ile Cys Ser Ala Val Gly Asn
                20                  25                  30
Leu Trp Val Thr Val Tyr Tyr Gly Val Pro Val Trp Arg Glu Ala Lys
            35                  40                  45
Thr Thr Leu Phe Cys Ala Ser Asp Ala Lys Ala Tyr Asp Arg Glu Val
50                  55                  60
His Asn Val Trp Ala Thr His Ala Cys Val Pro Thr Asp Pro Asn Pro
65                  70                  75                  80
Gln Glu Ile Val Leu Glu Asn Val Thr Glu Asn Phe Asn Met Trp Lys
                85                  90                  95
Asn Asp Met Val Asp Gln Met His Glu Asp Ile Ile Ser Leu Trp Asp
                100                 105                 110
Gln Ser Leu Lys Pro Cys Val Lys Leu Thr Pro Leu Cys Val Thr Leu
            115                 120                 125
Asn Cys Thr Asn Val Thr Ser Ser Ala Ala Asn Val Thr Ser Asn Val
130                 135                 140
Thr Asn Asp Ala Asn Asn Ala Ser Asn Ala Asn Gly Arg Asn Val Ile
145                 150                 155                 160
Asn Glu Asp Met Gln Asn Cys Ser Phe Asn Ala Thr Thr Glu Ile Arg
                165                 170                 175
Asp Arg Lys Lys Glu Met Tyr Ala Leu Phe Tyr Lys Leu Asp Ile Val
            180                 185                 190
Pro Leu Asp Gly Glu Lys Ser Asp Asn Arg Tyr Arg Leu Ile Asn Cys
            195                 200                 205
Asn Thr Ser Thr Leu Thr Gln Ala Cys Pro Lys Val Ser Phe Asp Pro
210                 215                 220
Ile Pro Ile His Tyr Cys Thr Pro Ala Gly Phe Ala Ile Leu Lys Cys
225                 230                 235                 240
Asn Asn Lys Thr Phe Asn Gly Thr Gly Pro Cys Asn Asn Val Ser Thr
                245                 250                 255
Val Gln Cys Thr His Gly Ile Lys Pro Val Val Ser Thr Gln Leu Leu
            260                 265                 270
Leu Asn Gly Ser Leu Ala Glu Glu Asp Ile Ile Ile Arg Ser Glu Asn
            275                 280                 285
Leu Thr Asn Asn Ala Lys Thr Ile Ile Val His Leu Asn Glu Ser Val
    290                 295                 300
Glu Ile Val Cys Thr Arg Pro Asn Asn Asn Thr Arg Lys Ser Ile Arg
305                 310                 315                 320
Ile Gly Pro Gly Gln Thr Phe Tyr Ala Asn Asn Asp Ile Ile Gly Asp
                325                 330                 335
Ile Arg Gln Ala His Cys Asn Ile Ser Glu Glu Lys Trp Asn Asn Thr
            340                 345                 350
Leu His Arg Val Trp Lys Lys Leu Val Glu His Phe Pro Asn Lys Thr
            355                 360                 365
Thr Ile Arg Phe Asp Arg His Ser Gly Gly Asp Leu Glu Ile Thr Thr
    370                 375                 380
His Ser Phe Asn Cys Gly Gly Glu Phe Phe Tyr Cys Asn Thr Ser Gly
385                 390                 395                 400
Leu Phe Asn Ile Thr Tyr Asn Ser Asn Tyr Tyr Asn Asp Thr Lys
                405                 410                 415
```

```
His Asn Gly Thr Lys Val Ile Thr Leu Pro Cys Arg Ile Lys Gln Ile
                420                 425                 430

Ile Asn Met Trp Gln Glu Val Gly Arg Ala Met Tyr Ala Pro Pro Ile
            435                 440                 445

Ala Gly Asn Ile Thr Cys Thr Ser Asn Ile Thr Gly Leu Leu Leu Thr
        450                 455                 460

Arg Asp Gly Gly Asn Asn Ser Thr Glu Thr Glu Thr Phe Arg Pro Gly
465                 470                 475                 480

Gly Gly Asp Met Arg Asp Asn Trp Arg Ser Glu Leu Tyr Lys Tyr Lys
                485                 490                 495

Val Val Glu Ile Lys Pro Leu Gly Ile Ala Pro Thr Gly Ala Lys Arg
            500                 505                 510

Arg Val Val Glu Arg Glu Lys Arg Ala Val Gly Ile Gly Ala Val Phe
        515                 520                 525

Leu Gly Phe Leu Gly Ala Ala Gly Ser Thr Met Gly Ala Ala Ser Ile
        530                 535                 540

Thr Leu Thr Val Gln Ala Arg Gln Leu Leu Ser Gly Ile Val Gln Gln
545                 550                 555                 560

Gln Ser Asn Leu Leu Lys Ala Ile Glu Ala Gln Gln His Leu Leu Gln
                565                 570                 575

Leu Thr Val Trp Gly Ile Lys Gln Leu Gln Thr Arg Val Leu Ala Ile
            580                 585                 590

Glu Arg Tyr Leu Lys Asp Gln Gln Leu Leu Gly Leu Trp Gly Cys Ser
        595                 600                 605

Ala Lys Leu Ile Cys Thr Thr Ala Val Pro Trp Asn Ser Ser Trp Ser
        610                 615                 620

Asn Lys Ser Glu Thr Glu Ile Trp Asn Asn Met Thr Trp Met Gln Trp
625                 630                 635                 640

Asp Arg Glu Ile Asn Asn Tyr Thr Asn Thr Ile Tyr Arg Leu Leu Glu
                645                 650                 655

Glu Ser Gln Asn Gln Gln Glu Lys Asn Glu Asn Asp Leu Leu Ala Leu
            660                 665                 670

Asp Lys Trp Asn Ser Leu Trp Asp Trp Phe Gly Ile Ser Asn Trp Leu
        675                 680                 685

Trp Tyr Ile Arg Ser Arg Ile Glu Gly Arg Gly Ser Gly Gly Tyr Ile
        690                 695                 700

Pro Glu Ala Pro Arg Asp Gly Gln Ala Tyr Val Arg Lys Asp Gly Glu
705                 710                 715                 720

Trp Val Leu Leu Ser Thr Phe Leu
                725

<210> SEQ ID NO 2
<211> LENGTH: 707
<212> TYPE: PRT
<213> ORGANISM: Artificial Sequence
<220> FEATURE:
<223> OTHER INFORMATION: Synthetic Construct

<400> SEQUENCE: 2

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Val Gly Asn
            20                  25                  30

Met Trp Val Thr Val Tyr Tyr Gly Val Pro Val Trp Thr Glu Ala Lys
        35                  40                  45
```

```
Ala Thr Leu Phe Cys Ala Ser Asp Ala Lys Ala Tyr Glu Lys Glu Val
 50                  55                  60

His Asn Val Trp Ala Thr His Ala Cys Val Pro Thr Asp Pro Asn Pro
 65                  70                  75                  80

Gln Glu Ile Ile Leu Glu Asn Val Thr Glu Asn Phe Asn Met Trp Lys
                 85                  90                  95

Asn Asp Met Val Asp Gln Met His Glu Asp Ile Ile Ser Ile Trp Asp
                100                 105                 110

Gln Ser Leu Lys Pro Cys Val Lys Leu Thr Pro Leu Cys Val Thr Leu
                115                 120                 125

Thr Cys Lys Asn Ile Thr Asn Asn Val Thr Asn Ile Phe Asn Ser Ser
130                 135                 140

Glu Gly Ile Asn Met Lys Glu Glu Ile Lys Asn Cys Ser Phe Asn Thr
145                 150                 155                 160

Thr Thr Glu Ile Arg Asp Lys Glu Lys Lys Glu Tyr Ala Leu Phe Tyr
                165                 170                 175

Lys Pro Asp Ile Val Gln Leu Gly Glu Arg Asn Ser Ser Arg Tyr Ile
                180                 185                 190

Leu Ile Asn Cys Asn Ser Ser Thr Ile Thr Gln Ala Cys Pro Lys Val
                195                 200                 205

Thr Phe Asp Pro Ile Pro Ile His Tyr Cys Ala Pro Ala Gly Tyr Ala
210                 215                 220

Ile Leu Lys Cys Asn Asn Lys Thr Phe Asn Gly Thr Gly Pro Cys Ser
225                 230                 235                 240

Asn Ile Ser Thr Val Gln Cys Thr His Gly Ile Lys Pro Val Val Ser
                245                 250                 255

Thr Gln Leu Leu Leu Asn Gly Ser Leu Ser Glu Gly Glu Ile Met Ile
                260                 265                 270

Arg Ser Glu Asn Leu Thr Asp Asn Thr Lys Thr Ile Ile Val His Leu
                275                 280                 285

Asn Glu Ser Val Glu Ile Val Cys Ile Arg Pro Gly Asn Asn Thr Arg
                290                 295                 300

Lys Gly Ile Arg Ile Gly Pro Gly Gln Val Phe Tyr Ala Thr Gly Asp
305                 310                 315                 320

Ile Ile Gly Asp Ile Arg Gln Ala Tyr Cys Asn Ile Ser Gly Lys Trp
                325                 330                 335

Asn Thr Thr Leu Glu Lys Val Lys Lys Leu Lys Glu His Phe Pro
                340                 345                 350

Asn Lys Thr Ile Asn Phe Asn Ser Ser Gly Gly Asp Leu Glu Ile
                355                 360                 365

Thr Thr His Ser Phe Asn Cys Arg Gly Glu Phe Phe Tyr Cys Asn Thr
                370                 375                 380

Thr Lys Leu Phe Thr Asn Thr Thr Asn Thr Thr Ile Leu Ile Pro
385                 390                 395                 400

Cys Arg Ile Lys Gln Phe Val Asn Met Trp Gln Glu Val Gly Arg Ala
                405                 410                 415

Met Tyr Ala Pro Pro Ile Ala Gly Asn Ile Thr Cys Asn Ser Ser Ile
                420                 425                 430

Thr Gly Leu Leu Leu Val Arg Asp Gly Gly Ile Ser Asn Asp Thr Asn
                435                 440                 445

Asn Thr Thr Glu Thr Phe Arg Pro Gly Gly Asn Met Lys Asp Asn
                450                 455                 460

Trp Arg Ser Glu Leu Tyr Ser Tyr Lys Val Val Glu Leu Lys Pro Leu
```

```
            465                 470                 475                 480
Gly Val Ala Pro Thr Gly Ala Lys Arg Arg Val Val Glu Met Glu Arg
                485                 490                 495

Ser Lys Arg Ala Val Gly Ile Gly Ala Ala Leu Leu Gly Phe Leu Gly
                500                 505                 510

Ala Ala Gly Ser Thr Met Gly Ala Ser Met Ala Leu Thr Val Gln
                515                 520                 525

Ala Arg Gln Leu Leu Ser Gly Ile Val Gln Gln Ser Asn Leu Leu
530                 535                 540

Arg Ala Ile Glu Ala Gln Gln His Met Leu Gln Leu Thr Val Trp Gly
545                 550                 555                 560

Ile Lys Gln Leu Gln Thr Arg Val Leu Ala Ile Glu Arg Tyr Leu Lys
                565                 570                 575

Asp Gln Gln Leu Leu Gly Leu Trp Gly Cys Ser Gly Lys Ile Ile Cys
                580                 585                 590

Thr Thr Asn Val Pro Trp Asn Ser Ser Trp Ser Asn Lys Ser Lys Glu
                595                 600                 605

Asp Ile Trp Asp Asn Met Thr Trp Met Gln Trp Asp Arg Glu Val Ser
610                 615                 620

Asn Tyr Thr Glu Thr Ile Tyr Arg Leu Leu Glu Ser Gln Thr Gln
625                 630                 635                 640

Gln Glu Lys Asn Glu Lys Glu Leu Leu Glu Leu Ser Lys Trp Asp Ser
                645                 650                 655

Leu Trp Ser Trp Phe Asn Ile Thr Asn Trp Leu Trp Tyr Thr Lys Ser
                660                 665                 670

Arg Ile Glu Gly Arg Gly Ser Gly Gly Tyr Ile Pro Glu Ala Pro Arg
                675                 680                 685

Asp Gly Gln Ala Tyr Val Arg Lys Asp Gly Glu Trp Val Leu Leu Ser
                690                 695                 700

Thr Phe Leu
705

<210> SEQ ID NO 3
<211> LENGTH: 716
<212> TYPE: PRT
<213> ORGANISM: Artificial Sequence
<220> FEATURE:
<223> OTHER INFORMATION: Synthetic Construct

<400> SEQUENCE: 3

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Met Gly Asn
                20                  25                  30

Met Trp Val Thr Val Tyr Tyr Gly Val Pro Val Trp Lys Glu Ala Lys
                35                  40                  45

Thr Thr Leu Phe Cys Ala Ser Asp Ala Lys Ala Tyr Val Lys Glu Val
                50                  55                  60

His Asn Ile Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Ser Ile Trp Asp
                100                 105                 110

Glu Ser Leu Lys Pro Cys Val Lys Leu Thr Pro Leu Cys Val Thr Leu
```

-continued

```
            115                 120                 125
Asp Cys Cys Ser Thr Phe Asn Cys Ser Asn Asn Ala Gly Thr Ile Glu
130                 135                 140
Glu Gln Glu Leu Lys Asn Cys Ser Phe Asn Ala Thr Thr Val Val Arg
145                 150                 155                 160
Asp Lys Lys Gln Thr Val Ser Ala Leu Phe Tyr Lys Leu Asp Val Val
                165                 170                 175
Pro Leu Gly Gly Asp Asn Asn Asn Asn Lys Ser Tyr Arg Leu Ile
                180                 185                 190
Asn Cys Asn Thr Ser Thr Ile Thr Gln Ala Cys Pro Lys Val Thr Phe
                195                 200                 205
Asp Pro Ile Pro Ile His Tyr Cys Ala Pro Ala Gly Tyr Ala Ile Leu
210                 215                 220
Lys Cys Asn Asn Lys Thr Phe Asn Gly Thr Gly Pro Cys Asn Asn Val
225                 230                 235                 240
Ser Thr Val Gln Cys Thr His Gly Ile Lys Pro Val Val Ser Thr Gln
                245                 250                 255
Leu Leu Leu Asn Gly Ser Leu Ala Glu Glu Glu Ile Ile Lys Ser
                260                 265                 270
Glu Asn Leu Thr Asn Asn Val Lys Thr Ile Ile Val His Leu Asn Asp
                275                 280                 285
Ser Val Glu Ile Val Cys Thr Arg Pro Asn Asn Asn Thr Arg Lys Ser
290                 295                 300
Val Arg Ile Gly Pro Gly Gln Thr Phe Tyr Ala Thr Gly Glu Ile Ile
305                 310                 315                 320
Gly Asn Ile Arg Gln Ala Tyr Cys Asn Ile Asn Lys Asp Lys Trp Asn
                325                 330                 335
Lys Thr Leu Gln Gln Val Gly Lys Arg Leu Ala Glu His Phe Pro Asn
                340                 345                 350
Lys Glu Ile Ile Lys Phe Ser Pro Ser Ser Gly Gly Asp Leu Glu Ile
                355                 360                 365
Thr Thr His Ser Phe Asn Cys Arg Gly Glu Phe Phe Tyr Cys Asn Thr
                370                 375                 380
Ser Gly Leu Phe Asn Gly Thr Tyr Asn Asn Gly Thr Tyr Asn Asp Gly
385                 390                 395                 400
Thr Asp Asn Ser Asn Asp Thr Ile Thr Leu Leu Cys Arg Ile Lys Gln
                405                 410                 415
Ile Ile Asn Met Trp Gln Gly Val Gly Lys Ala Ile Tyr Ala Pro Pro
                420                 425                 430
Ile Lys Gly Asn Ile Thr Cys Asn Ser Ser Ile Thr Gly Leu Leu Leu
                435                 440                 445
Thr Arg Asp Gly Gly Lys Gly Asp Asn Asn Thr Asn Asn Thr Glu Thr
                450                 455                 460
Phe Arg Pro Gly Gly Gly Asp Met Arg Asp Asn Trp Arg Asn Glu Leu
465                 470                 475                 480
Tyr Lys Tyr Lys Val Val Glu Ile Lys Pro Leu Gly Val Ala Pro Thr
                485                 490                 495
Thr Ala Lys Arg Arg Val Val Glu Arg Glu Lys Arg Ala Val Gly Ile
                500                 505                 510
Gly Ala Val Phe Leu Gly Phe Leu Gly Ala Ala Gly Ser Thr Met Gly
                515                 520                 525
Ala Ala Ser Ile Thr Leu Thr Val Gln Ala Arg Gln Leu Leu Ser Gly
                530                 535                 540
```

-continued

Ile Val Gln Gln Gln Ser Asn Leu Leu Arg Ala Ile Glu Ala Gln Gln
545                 550                 555                 560

His Met Leu Gln Leu Thr Val Trp Gly Ile Lys Gln Leu Gln Ala Arg
                565                 570                 575

Val Leu Ala Ile Glu Arg Tyr Leu Lys Asp Gln Gln Leu Leu Gly Ile
            580                 585                 590

Trp Gly Cys Ser Gly Lys Leu Ile Cys Thr Thr Asn Val Pro Trp Asn
        595                 600                 605

Ser Ser Trp Ser Asn Arg Ser Gln Glu Glu Ile Trp Arg Asn Met Thr
    610                 615                 620

Trp Met Gln Trp Asp Arg Glu Ile Asn Asn Tyr Thr Asn Thr Ile Tyr
625                 630                 635                 640

Thr Leu Leu Glu Ala Ser Gln Ile Gln Gln Glu Gln Asn Glu Lys Asp
                645                 650                 655

Leu Leu Ala Leu Asp Lys Trp Gln Asn Leu Trp Asn Trp Phe Asp Ile
            660                 665                 670

Thr Arg Trp Leu Trp Tyr Ile Lys Ser Arg Ile Glu Gly Arg Gly Ser
        675                 680                 685

Gly Gly Tyr Ile Pro Glu Ala Pro Arg Asp Gly Gln Ala Tyr Val Arg
    690                 695                 700

Lys Asp Gly Glu Trp Val Leu Leu Ser Thr Phe Leu
705                 710                 715

<210> SEQ ID NO 4
<211> LENGTH: 872
<212> TYPE: PRT
<213> ORGANISM: Artificial Sequence
<220> FEATURE:
<223> OTHER INFORMATION: Synthetic Construct

<400> SEQUENCE: 4

Met Arg Val Thr Gly Lys Trp Arg Asn Tyr Gln Gln Trp Trp Ile Trp
1               5                   10                  15

Gly Ile Leu Gly Phe Trp Met Leu Met Ile Cys Ser Val Val Gly Asn
            20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Asp Arg Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Val Thr Ser Ser Ala Ala Asn Val Thr Ser Asn Val
    130                 135                 140

Thr Asn Asp Ala Asn Asn Ala Ser Asn Ala Asn Gly Arg Asn Val Ile
145                 150                 155                 160

Asn Glu Asp Met Gln Asn Cys Ser Phe Asn Ala Thr Thr Glu Ile Arg
                165                 170                 175

Asp Arg Lys Lys Glu Met Tyr Ala Leu Phe Tyr Lys Leu Asp Ile Val
            180                 185                 190

```
Pro Leu Asp Gly Glu Lys Ser Asp Asn Arg Tyr Arg Leu Ile Asn Cys
        195                 200                 205

Asn Thr Ser Thr Leu Thr Gln Ala Cys Pro Lys Val Ser Phe Asp Pro
210                 215                 220

Ile Pro Ile His Tyr Cys Thr Pro Ala Gly Phe Ala Ile Leu Lys Cys
225                 230                 235                 240

Asn Asn Lys Thr Phe Asn Gly Thr Gly Pro Cys Asn Asn Val Ser Thr
                245                 250                 255

Val Gln Cys Thr His Gly Ile Lys Pro Val Val Ser Thr Gln Leu Leu
                260                 265                 270

Leu Asn Gly Ser Leu Ala Glu Glu Asp Ile Ile Arg Ser Glu Asn
                275                 280                 285

Leu Thr Asn Asn Ala Lys Thr Ile Ile Val His Leu Asn Glu Ser Val
290                 295                 300

Glu Ile Val Cys Thr Arg Pro Asn Asn Asn Thr Arg Lys Ser Ile Arg
305                 310                 315                 320

Ile Gly Pro Gly Gln Thr Phe Tyr Ala Asn Asn Asp Ile Ile Gly Asp
                325                 330                 335

Ile Arg Gln Ala His Cys Asn Ile Ser Glu Gly Lys Trp Asn Asn Thr
                340                 345                 350

Leu His Arg Val Trp Lys Lys Leu Val Glu His Phe Pro Asn Lys Thr
                355                 360                 365

Thr Ile Arg Phe Asp Arg His Ser Gly Gly Asp Leu Glu Ile Thr Thr
370                 375                 380

His Ser Phe Asn Cys Gly Gly Glu Phe Phe Tyr Cys Asn Thr Ser Gly
385                 390                 395                 400

Leu Phe Asn Ile Thr Tyr Asn Ser Asn Tyr Thr Tyr Asn Asp Thr Lys
                405                 410                 415

His Asn Gly Thr Lys Val Ile Thr Leu Pro Cys Arg Ile Lys Gln Ile
                420                 425                 430

Ile Asn Met Trp Gln Glu Val Gly Arg Ala Met Tyr Ala Pro Pro Ile
                435                 440                 445

Ala Gly Asn Ile Thr Cys Thr Ser Asn Ile Thr Gly Leu Leu Leu Thr
                450                 455                 460

Arg Asp Gly Gly Asn Asn Ser Thr Glu Thr Glu Thr Phe Arg Pro Gly
465                 470                 475                 480

Gly Gly Asp Met Arg Asp Asn Trp Arg Ser Glu Leu Tyr Lys Tyr Lys
                485                 490                 495

Val Val Glu Ile Lys Pro Leu Gly Ile Ala Pro Thr Gly Ala Lys Arg
                500                 505                 510

Arg Val Val Glu Arg Glu Lys Arg Ala Val Gly Ile Gly Ala Val Phe
                515                 520                 525

Leu Gly Phe Leu Gly Ala Ala Gly Ser Thr Met Gly Ala Ala Ser Ile
530                 535                 540

Thr Leu Thr Val Gln Ala Arg Gln Leu Leu Ser Gly Ile Val Gln Gln
545                 550                 555                 560

Gln Ser Asn Leu Leu Lys Ala Ile Glu Ala Gln Gln His Leu Leu Gln
                565                 570                 575

Leu Thr Val Trp Gly Ile Lys Gln Leu Gln Thr Arg Val Leu Ala Ile
                580                 585                 590

Glu Arg Tyr Leu Lys Asp Gln Gln Leu Leu Gly Leu Trp Gly Cys Ser
                595                 600                 605
```

```
Ala Lys Leu Ile Cys Thr Thr Ala Val Pro Trp Asn Ser Ser Trp Ser
    610                 615                 620
Asn Lys Ser Glu Thr Glu Ile Trp Asn Met Thr Trp Met Gln Trp
625                 630                 635                 640
Asp Arg Glu Ile Asn Asn Tyr Thr Asn Thr Ile Tyr Arg Leu Leu Glu
                645                 650                 655
Glu Ser Gln Asn Gln Gln Glu Lys Asn Glu Asn Asp Leu Leu Ala Leu
            660                 665                 670
Asp Lys Trp Asn Ser Leu Trp Asp Trp Phe Gly Ile Ser Asn Trp Leu
        675                 680                 685
Trp Tyr Ile Arg Ile Phe Ile Met Ile Val Gly Gly Leu Ile Gly Leu
    690                 695                 700
Arg Ile Ile Phe Ala Val Leu Ser Ile Val Asn Arg Val Arg Gln Gly
705                 710                 715                 720
Tyr Ser Pro Leu Ser Phe Gln Thr Leu Ile Pro Ser Pro Arg Gly Pro
                725                 730                 735
Asp Arg Pro Gly Gly Ile Glu Glu Gly Gly Glu Asn Asp Arg Asp
            740                 745                 750
Arg Ser Val Arg Leu Val Asn Gly Phe Leu Ala Leu Ala Trp Glu Asp
        755                 760                 765
Leu Arg Asn Leu Cys Leu Phe Cys Tyr His Arg Leu Arg Asp Phe Ile
    770                 775                 780
Leu Ile Ala Val Arg Val Val Glu Leu Leu Gly Arg Asn Ser Leu Arg
785                 790                 795                 800
Gly Leu Gln Arg Val Trp Glu Ala Leu Lys Val Leu Gly Asn Leu Val
                805                 810                 815
Gln Tyr Trp Gly Leu Glu Leu Lys Lys Ser Ala Ile Ser Leu Leu Asp
            820                 825                 830
Thr Ile Ala Ile Ala Val Ala Glu Gly Thr Asp Arg Ile Ile Glu Leu
        835                 840                 845
Leu Gln Arg Ile Cys Arg Ala Ile Tyr Asn Ile Pro Thr Arg Ile Arg
    850                 855                 860
Gln Gly Phe Glu Ala Ala Leu Gln
865                 870
```

<210> SEQ ID NO 5
<211> LENGTH: 844
<212> TYPE: PRT
<213> ORGANISM: Artificial Sequence
<220> FEATURE:
<223> OTHER INFORMATION: Synthetic Construct

<400> SEQUENCE: 5

```
Met Arg Val Arg Gly Ile Gln Arg Asn Trp Pro Gln Trp Trp Ile Trp
1                   5                   10                  15
Gly Ile Leu Gly Leu Leu Met Ile Ile Ile Cys Arg Gly Val Gly Asn
                20                  25                  30
Met Trp Val Thr Val Tyr Tyr Gly Val Pro Val Trp Thr Glu Ala Lys
            35                  40                  45
Ala Thr Leu Phe Cys Ala Ser Asp Ala Lys Ala Tyr Glu Lys Glu Val
        50                  55                  60
His Asn Val Trp Ala Thr His Ala Cys Val Pro Thr Asp Pro Asn Pro
65                  70                  75                  80
Gln Glu Ile Ile Leu Glu Asn Val Thr Glu Asn Phe Asn Met Trp Lys
                85                  90                  95
```

-continued

```
Asn Asp Met Val Asp Gln Met His Glu Asp Ile Ile Ser Ile Trp Asp
                100                 105                 110
Gln Ser Leu Lys Pro Cys Val Lys Leu Thr Pro Leu Cys Val Thr Leu
            115                 120                 125
Thr Cys Lys Asn Ile Thr Asn Asn Val Thr Asn Ile Phe Asn Ser Ser
    130                 135                 140
Glu Gly Ile Asn Met Lys Glu Glu Ile Lys Asn Cys Ser Phe Asn Thr
145                 150                 155                 160
Thr Thr Glu Ile Arg Asp Lys Glu Lys Lys Glu Tyr Ala Leu Phe Tyr
                165                 170                 175
Lys Pro Asp Ile Val Gln Leu Gly Glu Arg Asn Ser Ser Arg Tyr Ile
            180                 185                 190
Leu Ile Asn Cys Asn Ser Ser Thr Ile Thr Gln Ala Cys Pro Lys Val
    195                 200                 205
Thr Phe Asp Pro Ile Pro Ile His Tyr Cys Ala Pro Ala Gly Tyr Ala
210                 215                 220
Ile Leu Lys Cys Asn Asn Lys Thr Phe Asn Gly Thr Gly Pro Cys Ser
225                 230                 235                 240
Asn Ile Ser Thr Val Gln Cys Thr His Gly Ile Lys Pro Val Val Ser
                245                 250                 255
Thr Gln Leu Leu Leu Asn Gly Ser Leu Ser Glu Gly Glu Ile Met Ile
            260                 265                 270
Arg Ser Glu Asn Leu Thr Asp Asn Thr Lys Thr Ile Ile Val His Leu
    275                 280                 285
Asn Glu Ser Val Glu Ile Val Cys Ile Arg Pro Gly Asn Asn Thr Arg
290                 295                 300
Lys Gly Ile Arg Ile Gly Pro Gly Gln Val Phe Tyr Ala Thr Gly Asp
305                 310                 315                 320
Ile Ile Gly Asp Ile Arg Gln Ala Tyr Cys Asn Ile Ser Gly Lys Trp
                325                 330                 335
Asn Thr Thr Leu Glu Lys Val Lys Lys Lys Leu Lys Glu His Phe Pro
            340                 345                 350
Asn Lys Thr Ile Asn Phe Asn Ser Ser Ser Gly Gly Asp Leu Glu Ile
    355                 360                 365
Thr Thr His Ser Phe Asn Cys Arg Gly Glu Phe Phe Tyr Cys Asn Thr
370                 375                 380
Thr Lys Leu Phe Thr Asn Thr Thr Asn Thr Thr Ile Leu Ile Pro
385                 390                 395                 400
Cys Arg Ile Lys Gln Phe Val Asn Met Trp Gln Glu Val Gly Arg Ala
                405                 410                 415
Met Tyr Ala Pro Pro Ile Ala Gly Asn Ile Thr Cys Asn Ser Ser Ile
            420                 425                 430
Thr Gly Leu Leu Leu Val Arg Asp Gly Gly Ile Ser Asn Asp Thr Asn
    435                 440                 445
Asn Thr Thr Glu Thr Phe Arg Pro Gly Gly Gly Asn Met Lys Asp Asn
450                 455                 460
Trp Arg Ser Glu Leu Tyr Ser Tyr Lys Val Val Glu Leu Lys Pro Leu
465                 470                 475                 480
Gly Val Ala Pro Thr Gly Ala Lys Arg Arg Val Val Glu Met Glu Arg
                485                 490                 495
Ser Lys Arg Ala Val Gly Ile Gly Ala Ala Leu Leu Gly Phe Leu Gly
            500                 505                 510
Ala Ala Gly Ser Thr Met Gly Ala Ala Ser Met Ala Leu Thr Val Gln
```

```
            515                 520                 525
Ala Arg Gln Leu Leu Ser Gly Ile Val Gln Gln Ser Asn Leu Leu
    530                 535                 540

Arg Ala Ile Glu Ala Gln Gln His Met Leu Gln Leu Thr Val Trp Gly
545                 550                 555                 560

Ile Lys Gln Leu Gln Thr Arg Val Leu Ala Ile Glu Arg Tyr Leu Lys
                565                 570                 575

Asp Gln Gln Leu Leu Gly Leu Trp Gly Cys Ser Gly Lys Ile Ile Cys
            580                 585                 590

Thr Thr Asn Val Pro Trp Asn Ser Trp Ser Asn Lys Ser Lys Glu
        595                 600                 605

Asp Ile Trp Asp Asn Met Thr Trp Met Gln Trp Asp Arg Glu Val Ser
610                 615                 620

Asn Tyr Thr Glu Thr Ile Tyr Arg Leu Leu Glu Ser Gln Thr Gln
625                 630                 635                 640

Gln Glu Lys Asn Glu Lys Glu Leu Leu Glu Leu Ser Lys Trp Asp Ser
                645                 650                 655

Leu Trp Ser Trp Phe Asn Ile Thr Asn Trp Leu Trp Tyr Thr Lys Ile
            660                 665                 670

Phe Ile Met Ile Val Gly Gly Leu Ile Gly Leu Arg Ile Ile Phe Ala
        675                 680                 685

Val Leu Ser Ile Val Arg Arg Val Arg Gln Gly Tyr Ser Pro Leu Ser
690                 695                 700

Phe Gln Thr Leu Ile Pro Asn Pro Arg Gly Pro Asp Arg Pro Gly Gly
705                 710                 715                 720

Ile Glu Glu Glu Gly Gly Glu Gln Asp Arg Gly Lys Ser Ile Arg Leu
                725                 730                 735

Val Asn Gly Phe Leu Ala Leu Phe Trp Asp Asp Leu Arg Asn Leu Cys
            740                 745                 750

Leu Phe Ser Tyr His Leu Leu Arg Asp Phe Ile Leu Val Thr Ala Arg
        755                 760                 765

Ala Val Glu Leu Leu Gly Gln Arg Gly Trp Glu Ala Leu Lys Tyr Leu
770                 775                 780

Gly Ser Leu Val Gln Tyr Trp Gly Leu Glu Leu Lys Lys Ser Ala Ile
785                 790                 795                 800

Ser Leu Leu Asp Thr Leu Ala Ile Ala Val Gly Glu Gly Thr Asp Arg
                805                 810                 815

Ile Ile Arg Ile Val Gln Ser Ile Cys Arg Ala Ile Tyr Asn Thr Pro
            820                 825                 830

Arg Arg Ile Arg Gln Gly Phe Glu Thr Ala Leu Leu
        835                 840
```

<210> SEQ ID NO 6
<211> LENGTH: 860
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (791)..(791)
<223> OTHER INFORMATION: Xaa can be any naturally occurring amino acid

<400> SEQUENCE: 6

```
Met Arg Val Arg Gly Ile Arg Lys Asn Tyr Gln Gln Trp Trp Ile Trp
1               5                   10                  15
```

```
Gly Ile Leu Gly Phe Trp Ile Leu Met Ile Cys Ser Val Met Gly Asn
            20              25                  30

Met Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Val Lys Glu Val
        50              55                  60

His Asn Ile Trp Ala Thr His Ala Cys Val Pro Thr Asp Pro Asn Pro
65              70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Ser Ile Trp Asp
                100                 105                 110

Glu Ser Leu Lys Pro Cys Val Lys Leu Thr Pro Leu Cys Val Thr Leu
        115                 120                 125

Asp Cys Cys Ser Thr Phe Asn Cys Ser Asn Asn Ala Gly Thr Ile Glu
        130                 135                 140

Glu Gln Glu Leu Lys Asn Cys Ser Phe Asn Ala Thr Val Val Arg
145                 150                 155                 160

Asp Lys Lys Gln Thr Val Ser Ala Leu Phe Tyr Lys Leu Asp Val Val
                165                 170                 175

Pro Leu Gly Gly Asp Asn Asn Asn Asn Lys Ser Tyr Arg Leu Ile
                180                 185                 190

Asn Cys Asn Thr Ser Thr Ile Thr Gln Ala Cys Pro Lys Val Thr Phe
        195                 200                 205

Asp Pro Ile Pro Ile His Tyr Cys Ala Pro Ala Gly Tyr Ala Ile Leu
        210                 215                 220

Lys Cys Asn Asn Lys Thr Phe Asn Gly Thr Gly Pro Cys Asn Asn Val
225                 230                 235                 240

Ser Thr Val Gln Cys Thr His Gly Ile Lys Pro Val Val Ser Thr Gln
                245                 250                 255

Leu Leu Leu Asn Gly Ser Leu Ala Glu Glu Ile Ile Lys Ser
                260                 265                 270

Glu Asn Leu Thr Asn Asn Val Lys Thr Ile Ile Val His Leu Asn Asp
        275                 280                 285

Ser Val Glu Ile Val Cys Thr Arg Pro Asn Asn Asn Thr Arg Lys Ser
        290                 295                 300

Val Arg Ile Gly Pro Gly Gln Thr Phe Tyr Ala Thr Gly Glu Ile Ile
305                 310                 315                 320

Gly Asn Ile Arg Gln Ala Tyr Cys Asn Ile Asn Lys Asp Lys Trp Asn
                325                 330                 335

Lys Thr Leu Gln Gln Val Gly Lys Arg Leu Ala Glu His Phe Pro Asn
                340                 345                 350

Lys Glu Ile Ile Lys Phe Ser Pro Ser Ser Gly Gly Asp Leu Glu Ile
            355                 360                 365

Thr Thr His Ser Phe Asn Cys Arg Gly Glu Phe Phe Tyr Cys Asn Thr
        370                 375                 380

Ser Gly Leu Phe Asn Gly Thr Tyr Asn Asn Gly Thr Tyr Asn Asp Gly
385                 390                 395                 400

Thr Asp Asn Ser Asn Asp Thr Ile Thr Leu Leu Cys Arg Ile Lys Gln
                405                 410                 415

Ile Ile Asn Met Trp Gln Gly Val Gly Lys Ala Ile Tyr Ala Pro Pro
            420                 425                 430

Ile Lys Gly Asn Ile Thr Cys Asn Ser Ser Ile Thr Gly Leu Leu Leu
```

```
              435                 440                 445
Thr Arg Asp Gly Gly Lys Gly Asp Asn Asn Thr Asn Asn Thr Glu Thr
450                 455                 460

Phe Arg Pro Gly Gly Gly Asp Met Arg Asp Asn Trp Arg Asn Glu Leu
465                 470                 475                 480

Tyr Lys Tyr Lys Val Val Glu Ile Lys Pro Leu Gly Val Ala Pro Thr
                485                 490                 495

Thr Ala Lys Arg Arg Val Val Glu Arg Glu Lys Arg Ala Val Gly Ile
            500                 505                 510

Gly Ala Val Phe Leu Gly Phe Leu Gly Ala Ala Gly Ser Thr Met Gly
        515                 520                 525

Ala Ala Ser Ile Thr Leu Thr Val Gln Ala Arg Gln Leu Leu Ser Gly
    530                 535                 540

Ile Val Gln Gln Gln Ser Asn Leu Leu Arg Ala Ile Glu Ala Gln Gln
545                 550                 555                 560

His Met Leu Gln Leu Thr Val Trp Gly Ile Lys Gln Leu Gln Ala Arg
                565                 570                 575

Val Leu Ala Ile Glu Arg Tyr Leu Lys Asp Gln Gln Leu Leu Gly Ile
            580                 585                 590

Trp Gly Cys Ser Gly Lys Leu Ile Cys Thr Thr Asn Val Pro Trp Asn
        595                 600                 605

Ser Ser Trp Ser Asn Arg Ser Gln Glu Glu Ile Trp Arg Asn Met Thr
610                 615                 620

Trp Met Gln Trp Asp Arg Glu Ile Asn Asn Tyr Thr Asn Thr Ile Tyr
625                 630                 635                 640

Thr Leu Leu Glu Ala Ser Gln Ile Gln Gln Glu Gln Asn Glu Lys Asp
                645                 650                 655

Leu Leu Ala Leu Asp Lys Trp Gln Asn Leu Trp Asn Trp Phe Asp Ile
            660                 665                 670

Thr Arg Trp Leu Trp Tyr Ile Lys Ile Phe Ile Met Ile Val Gly Gly
        675                 680                 685

Leu Ile Gly Leu Arg Ile Ile Phe Ala Val Leu Ser Ile Val Lys Arg
    690                 695                 700

Val Arg Gln Gly Tyr Ser Pro Leu Pro Leu Gln Thr Leu Thr Pro Asn
705                 710                 715                 720

Gln Arg Ala Pro Asp Arg Leu Gly Arg Ile Glu Glu Gly Gly Gly Glu
                725                 730                 735

Gln Asp Arg Asp Arg Ser Ile Arg Leu Val Asn Gly Phe Leu Ala Leu
            740                 745                 750

Phe Trp Asp Asp Leu Arg Ser Leu Cys Leu Phe Cys Tyr His Arg Leu
        755                 760                 765

Arg Asp Phe Ile Leu Ile Ala Ala Arg Ala Ala Glu Leu Leu Gly Arg
    770                 775                 780

Ser Ser Cys Lys Gly Leu Xaa Arg Gly Trp Glu Ile Leu Lys Tyr Leu
785                 790                 795                 800

Gly Ser Leu Val Gln Tyr Trp Gly Leu Glu Leu Lys Lys Ser Ala Ile
                805                 810                 815

Ser Leu Leu Asp Ile Ile Ala Ile Arg Val Ala Glu Gly Thr Asp Arg
            820                 825                 830

Ile Ile Glu Leu Ile Gln Arg Thr Gly Arg Ala Ile Leu Asn Ile Pro
        835                 840                 845

Thr Arg Ile Arg Gln Gly Phe Glu Ala Ala Leu Leu
    850                 855                 860
```

```
<210> SEQ ID NO 7
<211> LENGTH: 708
<212> TYPE: PRT
<213> ORGANISM: Artificial Sequence
<220> FEATURE:
<223> OTHER INFORMATION: Synthetic Construct

<400> SEQUENCE: 7

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Gly Asn Met Trp Val Thr Val Tyr Tyr Gly Val Pro Val
        35                  40                  45

Trp Thr Asp Ala Lys Thr Thr Leu Phe Cys Ala Ser Asp Thr Lys Ala
    50                  55                  60

Tyr Asp Arg Glu Val His Asn Val Trp Ala Thr His Ala Cys Val Pro
65                  70                  75                  80

Thr Asp Pro Asn Pro Gln Glu Ile Val Leu Glu Asn Val Thr Glu Asn
                85                  90                  95

Phe Asn Met Trp Lys Asn Asp Met Val Asp Gln Met His Glu Asp Ile
            100                 105                 110

Ile Ser Leu Trp Asp Gln Ser Leu Lys Pro Cys Val Lys Leu Thr Pro
        115                 120                 125

Leu Cys Val Thr Leu His Cys Thr Asn Ala Thr Phe Lys Asn Asn Val
    130                 135                 140

Thr Asn Asp Met Asn Lys Glu Ile Arg Asn Cys Ser Phe Asn Thr Thr
145                 150                 155                 160

Thr Glu Ile Arg Asp Lys Lys Gln Gln Gly Tyr Ala Leu Phe Tyr Arg
                165                 170                 175

Pro Asp Ile Val Leu Leu Lys Glu Asn Arg Asn Asn Ser Asn Asn Ser
            180                 185                 190

Glu Tyr Ile Leu Ile Asn Cys Asn Ala Ser Thr Ile Thr Gln Ala Cys
        195                 200                 205

Pro Lys Val Asn Phe Asp Pro Ile Pro Ile His Tyr Cys Ala Pro Ala
    210                 215                 220

Gly Tyr Ala Ile Leu Lys Cys Asn Asn Lys Thr Phe Ser Gly Lys Gly
225                 230                 235                 240

Pro Cys Asn Asn Val Ser Thr Val Gln Cys Thr His Gly Ile Lys Pro
                245                 250                 255

Val Val Ser Thr Gln Leu Leu Leu Asn Gly Ser Leu Ala Glu Lys Glu
            260                 265                 270

Ile Ile Ile Arg Ser Glu Asn Leu Thr Asp Asn Val Lys Thr Ile Ile
        275                 280                 285

Val His Leu Asn Lys Ser Val Glu Ile Val Cys Thr Arg Pro Asn Asn
    290                 295                 300

Asn Thr Arg Lys Ser Met Arg Ile Gly Pro Gly Gln Thr Phe Tyr Ala
305                 310                 315                 320

Thr Gly Asp Ile Ile Gly Asp Ile Arg Gln Ala Tyr Cys Asn Ile Ser
                325                 330                 335

Gly Ser Lys Trp Asn Glu Thr Leu Lys Arg Val Lys Glu Lys Leu Gln
            340                 345                 350

Glu Asn Tyr Asn Asn Lys Thr Ile Lys Phe Ala Pro Ser Ser Gly
        355                 360                 365
```

Gly Asp Leu Glu Ile Thr Thr His Ser Phe Asn Cys Arg Gly Glu Phe
370                 375                 380

Phe Tyr Cys Asn Thr Thr Arg Leu Phe Asn Asn Asn Ala Thr Glu Asp
385                 390                 395                 400

Glu Thr Ile Thr Leu Pro Cys Arg Ile Lys Gln Ile Ile Asn Met Trp
            405                 410                 415

Gln Gly Val Gly Arg Ala Met Tyr Ala Pro Pro Ile Ala Gly Asn Ile
            420                 425                 430

Thr Cys Lys Ser Asn Ile Thr Gly Leu Leu Leu Val Arg Asp Gly Gly
            435                 440                 445

Glu Asp Asn Lys Thr Glu Glu Ile Phe Arg Pro Gly Gly Gly Asn Met
450                 455                 460

Lys Asp Asn Trp Arg Ser Glu Leu Tyr Lys Tyr Lys Val Ile Glu Leu
465                 470                 475                 480

Lys Pro Leu Gly Ile Ala Pro Thr Gly Ala Lys Glu Arg Val Val Glu
            485                 490                 495

Arg Glu Glu Arg Ala Val Gly Ile Gly Ala Val Phe Leu Gly Phe Leu
            500                 505                 510

Gly Ala Ala Gly Ser Thr Met Gly Ala Ala Ser Leu Thr Leu Thr Val
            515                 520                 525

Gln Ala Arg Gln Leu Leu Ser Ser Ile Val Gln Gln Gln Ser Asn Leu
            530                 535                 540

Leu Arg Ala Ile Glu Ala Gln Gln His Met Leu Gln Leu Thr Val Trp
545                 550                 555                 560

Gly Ile Lys Gln Leu Gln Thr Arg Val Leu Ala Ile Glu Arg Tyr Leu
            565                 570                 575

Lys Asp Gln Gln Leu Leu Gly Ile Trp Gly Cys Ser Gly Lys Leu Ile
            580                 585                 590

Cys Thr Thr Asn Val Pro Trp Asn Ser Ser Trp Ser Asn Lys Ser Gln
            595                 600                 605

Thr Asp Ile Trp Asn Asn Met Thr Trp Met Glu Trp Asp Arg Glu Ile
            610                 615                 620

Ser Asn Tyr Thr Asp Thr Ile Tyr Arg Leu Leu Glu Asp Ser Gln Thr
625                 630                 635                 640

Gln Gln Glu Lys Asn Glu Lys Asp Leu Leu Ala Leu Asp Ser Trp Lys
                645                 650                 655

Asn Leu Trp Ser Trp Phe Asp Ile Ser Asn Trp Leu Trp Tyr Ile Lys
            660                 665                 670

Ser Arg Ile Glu Gly Arg Gly Ser Gly Gly Tyr Ile Pro Glu Ala Pro
            675                 680                 685

Arg Asp Gly Gln Ala Tyr Val Arg Lys Asp Gly Glu Trp Val Leu Leu
690                 695                 700

Ser Thr Phe Leu
705

<210> SEQ ID NO 8
<211> LENGTH: 27
<212> TYPE: PRT
<213> ORGANISM: Artificial Sequence
<220> FEATURE:
<223> OTHER INFORMATION: Synthetic Construct

```
-continued

<400> SEQUENCE: 8

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25
```

STABILIZED HUMAN IMMUNODEFICIENCY VIRUS (HIV) CLADE C ENVELOPE (ENV) TRIMER VACCINES AND METHODS OF USING SAME

STATEMENT AS TO FEDERALLY FUNDED RESEARCH

This invention was made with government support under AI084794 and AI096040 awarded by NIH. The government has certain rights in the invention.

BACKGROUND OF THE INVENTION

Vaccines that elicit cellular immune responses against viruses seek to reflect global viral diversity in order to effectively treat or prevent viral infection. For HIV vaccines, the initiation of robust and diverse human immunodeficiency virus (HIV)-specific T cell responses is desirable for an effective HIV vaccine. The highly variable Envelope protein (Env) is the primary target for neutralizing antibodies against HIV, and vaccine antigens may be tailored accordingly to elicit these antibody responses. To this end, immunogens mimicking the trimeric structure of Env on the native HIV virion are actively being pursued as antibody-based HIV vaccines. However, it has proven difficult to produce biochemically stable trimeric Env immunogens that elicit diverse neutralizing antibody responses.

Thus, there is an unmet need in the field for the development of vaccines that include novel, optimized trimeric Env immunogens, which can elicit a broad immune response (e.g., a broadly neutralizing antibody response) in order to allow for more successful HIV vaccination outcomes.

SUMMARY OF THE INVENTION

In a first aspect, the invention features a stabilized trimer having three gp140 polypeptides in which at least one (e.g., two or each) of the gp140 polypeptides (e.g., clade C gp140 polypeptides) includes an amino acid sequence having at least 90% identity (e.g., at least 91%, 92%, 93%, 94%, 95%, 96%, 97%, 98%, or 99% identity) to, or the sequence of, SEQ ID NO: 1 (459C gp140-Foldon (gp140Fd)), SEQ ID NO: 2 (405C gp140Fd), or SEQ ID NO: 3 (939C gp140Fd). In some embodiments, at least one (e.g., two or each) of the gp140 polypeptides (e.g., clade C gp140 polypeptides) includes an amino acid sequence having substantially the sequence of (e.g., 99% or more identity), or the sequence of, SEQ ID NO: 1 (459C gp140Fd), SEQ ID NO: 2 (405C gp140Fd), or SEQ ID NO: 3 (939C gp140Fd). In a specific embodiment, each of the gp140 polypeptides includes an amino acid sequence having substantially the sequence of SEQ ID NO: 1. In an alternate embodiment, each of the gp140 polypeptides includes an amino acid sequence having substantially the sequence of SEQ ID NO: 2. In yet another embodiment, each of the gp140 polypeptides includes an amino acid sequence having substantially the sequence of SEQ ID NO: 3. In some embodiments, the stabilized gp140 trimer of the invention is a stabilized clade C 459C, 405C, and 939C gp140 homotrimer. In other embodiments, the stabilized trimers are heterotrimers, each heterotrimer including at least two different types of gp140 polypeptides.

In a second aspect, the invention features a composition including at least one (e.g., one, two, three, or four or more) stabilized trimer of the first aspect. In one embodiment, the composition of the second aspect includes at least two (e.g., two, three, or four or more) different stabilized trimers of the first aspect. The composition may, for example, include two different stabilized trimers of the first aspect (e.g., a composition including 459C and 405C homotrimers, or variants thereof; a composition including 459C and 939C homotrimers, or variants thereof; a composition including 939C and 405C homotrimers, or variants thereof). In another embodiment, the composition includes at least three (e.g., three, four, or five or more) different stabilized trimers of the first aspect. The composition may, for example, include three different stabilized trimers of the first aspect (e.g., a composition including 459C, 405C, and 939C homotrimers, or variants thereof). In another embodiment, the composition further includes another stabilized trimer, such as a stabilized C97ZA012 gp140 trimer (e.g., a stabilized C97ZA012 gp140 trimer wherein at least one or two of the gp140 polypeptides, and preferably each of the three gp140 polypeptides, includes an amino acid sequence having at least 90% identity (e.g., at least 91%, 92%, 93%, 94%, 95%, 96%, 97%, 98%, or 99% identity) to, or the sequence of, SEQ ID NO: 7). Accordingly, in some embodiments, the composition may include 459C, 405C, and C97ZA012 gp140 trimers (e.g., homotrimers), or variants thereof; 459C, 939C, and C97ZA012 gp140 trimers (e.g., homotrimers), or variants thereof; 939C, 405C, and C97ZA012 gp140 trimers (e.g., homotrimers), or variants thereof; or 459C, 405C, 939C, and C97ZA012 gp140 trimers (e.g., homotrimers), or variants thereof. In some embodiments, the different stabilized trimer(s) may be a homotrimer or a heterotrimer. In some embodiments, the compositions of the second aspect further include a pharmaceutically acceptable carrier, excipient, or diluent, and/or an adjuvant.

In a third aspect, the invention features a vaccine including any one of the compositions of the second aspect. In some embodiments, the vaccine is used for treating or reducing the risk of a human immunodeficiency virus (HIV) infection (e.g., HIV-1 infection) in a subject in need thereof. In some embodiments, the vaccine elicits production of neutralizing anti-HIV antisera (e.g., neutralizing anti-HIV-1 antisera) after administration to the subject. The anti-HIV antisera can neutralize HIV (e.g., HIV-1), for example, selected from any one or more of clade A, clade B, and clade C.

In a fourth aspect, the invention features a nucleic acid molecule having a nucleotide sequence that encodes at least one (e.g., one, two, or three or more) gp140 polypeptide, wherein the at least one gp140 polypeptide includes: (a) an amino acid sequence having at least 90% identity (e.g., at least 91%, 92%, 93%, 94%, 95%, 96%, 97%, 98%, or 99% identity) to, or the sequence of, SEQ ID NO: 1; (b) an amino acid sequence having at least 90% identity (e.g., at least 91%, 92%, 93%, 94%, 95%, 96%, 97%, 98%, or 99% identity) to, or the sequence of, SEQ ID NO: 2; and/or (c) an amino acid sequence having at least 90% identity (e.g., at least 91%, 92%, 93%, 94%, 95%, 96%, 97%, 98%, or 99% identity) to, or the sequence of SEQ ID NO: 3, or combinations thereof. In some embodiments, the nucleic acid molecule further includes a nucleotide sequence that encodes one or more different (e.g., a second, third, or fourth) gp140 polypeptides (e.g., gp140 polypeptides having at least 90% identity (e.g., at least 91%, 92%, 93%, 94%, 95%, 96%, 97%, 98%, or 99% identity) to, or the sequence of, SEQ ID NO: 1, 2, and/or 3). In some embodiments, the nucleic acid molecule includes one or more internal ribosome entry site (IRES) sequences to allow for the expression of multiple peptide or polypeptide chains from the single nucleic acid molecule transcript.

In a fifth aspect, the invention features a vector including one or more nucleic acid molecules of the fourth aspect. In some embodiments, the vector is an adenovirus vector or a poxvirus vector. The adenovirus vector may be derived, for example, from a recombinant adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof (e.g., adenovirus serotype 5 HVR48 (Ad5HVR48)). The poxvirus vector may be derived, for example, from modified vaccinia virus Ankara (MVA).

In a sixth aspect, the invention provides a method of treating or reducing the risk of an HIV (e.g., HIV-1) infection in a subject in need thereof by administering a therapeutically effective amount of a composition of the invention (e.g., any one of the stabilized trimers of the first aspect, the compositions of the second aspect, the vaccines of the third aspect, the nucleic acid molecules of the fourth aspect, and/or the vectors of the fifth aspect) to the subject, such as a mammal, for example, a human. Treating, according to this sixth aspect of the invention, can be therapeutic or prophylactic.

In a seventh aspect, the invention provides a method of reducing an HIV-mediated activity in a subject infected with HIV (e.g., HIV-1) by administering a therapeutically effective amount of a composition of the invention (e.g., any one of the stabilized trimers of the first aspect, the compositions of the second aspect, the vaccines of the third aspect, the nucleic acid molecules of the fourth aspect, and/or the vectors of the fifth aspect) to the subject. In some embodiments, the HIV-mediated activity is viral spread, infection, or cell fusion. Cell fusion may be, for example, target cell entry or syncytial formation. In some embodiments, the HIV titer in the subject infected with HIV is decreased (e.g., by at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more compared to HIV titer of the subject prior to treatment or a control subject infected with HIV but not treated with the composition(s) of the invention) after administration of the vaccine to the subject, such as a mammal, for example, a human.

In some embodiments, the composition (e.g., a vaccine) is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions. In some embodiments, the subject is administered at least one dose (e.g., 1, 2, 3, 4, 5, 6, 7, 8, 9, 10, or more doses) of the composition or is administered at least one dose (e.g., 1, 2, 3, 4, 5, 6, 7, 8, 9, 10, or more doses) daily, weekly, monthly, or yearly. The administration period may be defined (e.g., 1-4 weeks, 1-12 months, 1-20 years) or may be for the life of the subject. In other embodiments, the subject is administered at least two doses (e.g., 2, 3, 4, 5, 6, 7, 8, 9, 10, or more doses) of the composition. In yet another embodiment, the composition is administered to said subject as a prime or a boost composition or in a prime-boost regimen. In particular embodiments, for example, the composition is administered as a boost (e.g., a 459C, 405C, and 939C multivalent boost composition), following a prime composition including a stabilized C97ZA012 gp140 trimer, such as a C97ZA012 gp140 trimer wherein at least one or two of the gp140 polypeptides, and preferably each of the three gp140 polypeptides, includes an amino acid sequence having at least 90% identity (e.g., at least 91%, 92%, 93%, 94%, 95%, 96%, 97%, 98%, or 99% identity) to, or the sequence of, SEQ ID NO: 7.

In some embodiments, the subject may, for example, be administered polypeptide compositions of the invention (e.g., stabilized clade C gp140 Env trimers of the invention) in a non-vectored composition. The polypeptide composition administered may include between approximately 1 μg and 1 mg of stabilized Env trimers, preferably between 50 μg and 300 μg of stabilized Env trimers, and more preferably around 100 μg of stabilized Env trimers of the invention.

In embodiments in which the delivery vector is a virus, the subject can be administered at least about $1 \times 10^3$ viral particles (vp)/dose or between $1 \times 10^1$ and $1 \times 10^{14}$ vp/dose, preferably between $1 \times 10^3$ and $1 \times 10^{12}$ vp/dose, and more preferably between $1 \times 10^5$ and $1 \times 10^{11}$ vp/dose. The composition may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-exposure or pre-diagnosis, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, 20 years or longer post-diagnosis or post-exposure or to HIV. The subject is administered one or more doses of the composition once daily, weekly, monthly, or yearly. When treating an HIV infection, the composition(s) of the invention (e.g., any one of the stabilized trimers of the first, second, or third aspect, the compositions of the fourth or fifth aspect, the vaccines of the sixth aspect, the nucleic acid molecules of the seventh aspect, and/or the vectors of the eighth aspect) may be administered to the subject either before the occurrence of symptoms of an HIV infection or disease/syndrome (e.g., acquired immune deficiency syndrome (AIDS)) or a definitive diagnosis, or after diagnosis or symptoms become evident. The composition(s) may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

In some embodiments of the sixth and seventh aspects, the method further includes administering at least one additional therapeutic agent. For example, the additional therapeutic agent may be a broadly neutralizing antibody (bnAb), such as, e.g., an N332 glycan-dependent antibody, a CD4 binding site (CD4bs)-specific antibody, or a V2 glycan-dependent antibody. The N332 glycan-dependent antibody can be, for example, selected from the group consisting of PGT121, PGT122, PGT123, PGT124, PGT125, PGT126, PGT127, PGT128, PGT130, PGT131, PGT132, PGT133, PGT134, PGT135, PGT136, PGT137, PGT138, PGT139, PGT141, PGT142, PGT143, PGT144, PGT145, PGT151, PGT152, PGT153, PGT154, PGT155, PGT156, PGT157, PGT158, 10-1074, and a derivative or clonal relative thereof. In preferred embodiments, the N332 glycan-dependent antibody is PGT121 or 10-1074. In additional embodiments, the CD4bs-specific antibody is 3BNC117, VRC07-523, or a derivative or clonal relative thereof. In a further embodiment, the V2 glycan-dependent antibody is CAP256-VRC26 or a derivative or clonal relative thereof.

In an eighth aspect, the invention provides methods of manufacturing a vaccine for treating or reducing the risk of an HIV infection in a subject in need thereof. The method includes the steps of: (a) contacting a nucleic acid of the fourth aspect of the invention (e.g., a vector of the fifth aspect) with a cell; and (b) expressing the nucleic acid/vector in the cell to form a stabilized trimer. In some embodiments, the method is performed in vitro, in vivo, or ex vivo. In some embodiments, the cell is a bacterial, plant, or mammalian cell (e.g., a human or non-human mammalian cell). In a preferred embodiment, the mammalian cell is a 293T cell.

In a ninth aspect, the invention features a kit including: (a) a composition of the invention (e.g., any one of the stabilized trimers of the first aspect, the compositions of the second aspect, the vaccines of the third aspect, the nucleic acid molecules of the fourth aspect, and/or the vectors of the fifth aspect, e.g., a vaccine including 459C, 405C, and/or 939C homotrimers); (b) a pharmaceutically acceptable carrier, excipient, or diluent; and (c) instructions for use thereof. The kit may optionally include an adjuvant.

In a tenth aspect, the invention features an HIV clade C gp140 Env polypeptide including (a) an amino acid sequence having at least 90% identity (e.g., at least 91%, 92%, 93%, 94%, 95%, 96%, 97%, 98%, 99%, or 100% identity) to SEQ ID NO: 1 (459C gp140-foldon (gp140Fd) polypeptide); an amino acid sequence having at least 90% identity (e.g., at least 91%, 92%, 93%, 94%, 95%, 96%, 97%, 98%, 99%, or 100% identity) to SEQ ID NO: 2 (405C gp140Fd polypeptide); or (c) an amino acid sequence having at least 90% identity (e.g., at least 91%, 92%, 93%, 94%, 95%, 96%, 97%, 98%, 99%, or 100% identity) to SEQ ID NO: 3 (939C gp140Fd polypeptide).

In preferred embodiments of all aspects of the invention, the subject is a mammal, preferably a primate, such as a human.

Definitions

As used herein, the term "about" means+/−10% of the recited value.

By "adenovirus" is meant a medium-sized (90-100 nm), non-enveloped icosahedral virus that includes a capsid and a double-stranded linear DNA genome. The adenovirus can be a naturally occurring, but isolated, adenovirus (e.g., sAd4287, sAd4310A, or sAd4312) or a recombinant adenovirus (e.g., replication-defective or replication competent sAd4287, sAd4310A, or sAd4312, or a chimeric variant thereof).

As used herein, "administering" is meant a method of giving a dosage of a pharmaceutical composition (e.g., a composition of the invention, such as any one of the vaccines of the third aspect, the compositions of the second aspect, the nucleic acid molecules of the fourth aspect, and/or the vectors of the fifth aspect) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions. The preferred method of administration can vary depending on various factors (e.g., the components of the composition being administered and the severity of the condition being treated).

As used herein, the term "clade" refers to related human immunodeficiency viruses (HIVs) classified according to their degree of genetic similarity. There are currently three groups of HIV-1 isolates: M, N and O. Group M (major strains) consists of at least ten clades, A through J. Group O (outer strains) may consist of a similar number of clades. Group N is a new HIV-1 isolate that has not been categorized in either group M or O. In certain exemplary embodiments, a composition of the invention (e.g., any one of the vaccines of the third aspect, the compositions of the second aspect, the nucleic acid molecules of the fourth aspect, and/or the vectors of the fifth aspect) as described herein will recognize and raise an immune response (e.g., neutralizing anti-HIV antisera) against two, three, four, five, six, seven, eight, nine, ten or more clades and/or two or more groups of HIV.

Throughout this specification and claims, the word "comprise," or variations such as "comprises" or "comprising," will be understood to imply the inclusion of a stated integer or group of integers but not the exclusion of any other integer or group of integers.

As used herein, the term "envelope glycoprotein" refers, but is not limited to, the glycoprotein that is expressed on the surface of the envelope of HIV virions and the surface of the plasma membrane of HIV infected cells. The env gene encodes gp160, which is proteolytically cleaved into the gp120 and gp41 Envelope (Env) proteins. Gp120 binds to the CD4 receptor on a target cell that has such a receptor, such as, e.g., a T-helper cell. Gp41 is non-covalently bound to gp120, and provides the second step by which HIV enters the cell. It is originally buried within the viral envelope, but when gp120 binds to a CD4 receptor, gp120 changes its conformation causing gp41 to become exposed, where it can assist in fusion with the host cell. Gp140 is a soluble form of gp160, wherein the transmembrane and C-terminal regions are absent.

By "gene product" is meant to include mRNAs transcribed from a gene as well as polypeptides translated from those mRNAs.

By "heterologous nucleic acid molecule" or "heterologous gene" is meant any exogenous nucleic acid molecule (e.g., a nucleic acid molecule encoding an optimized gp140 Env polypeptide of the invention) that can be inserted into a vector of the invention (e.g., an adenovirus or poxvirus vector) for transfer into a cell, tissue, or organism, for subsequent expression of a gene product of interest or fragment thereof encoded by the heterologous nucleic acid molecule or gene. In a preferred embodiment, the heterologous nucleic acid molecule, which can be administered to a cell or subject as part of the present invention, can include, but is not limited to, a nucleic acid molecule encoding at least one optimized clade C Env polypeptide (e.g., an optimized 459C, 405C, or 939C gp140 polypeptide).

By "human immunodeficiency virus" or "HIV" is meant a virus of the genus Lentivirus, part of the family of Retroviridae, and includes, but is not limited to, HIV type 1 (HIV-1) and HIV type 2 (HIV-2), two species of HIV that infect humans.

By "immune response" is meant any response to an antigen or antigenic determinant by the immune system of a subject (e.g., a human). Exemplary immune responses include humoral immune responses (e.g., production of antigen-specific antibodies, e.g., neutralizing antibodies (NAbs)) and cell-mediated immune responses (e.g., lymphocyte proliferation).

As used herein, the term "reducing" with respect to HIV refers to a reduction or decrease of an HIV-mediated activity (e.g., infection, fusion (e.g., target cell entry and/or syncytia formation), viral spread, etc.) and/or a decrease in viral titer. HIV-mediated activity and/or HIV titer may be decreased by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control subject (e.g., an untreated subject or a subject treated with a placebo).

By "neutralizing antibody" or "NAb" is meant an antibody which either is purified from, or is present in, serum and which recognizes a specific antigen (e.g., HIV Env glycoprotein, such as a gp140 polypeptide or a gp120 polypeptide) and inhibits the effect(s) of the antigen in the host (e.g., a human). As used herein, the antibody can be a single antibody or a plurality of antibodies.

"Nucleic acid" or "polynucleotide," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semisolid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

By "optimized" is meant an immunogenic polypeptide that is not a naturally-occurring peptide, polypeptide, or protein, such as a non-naturally occurring viral polypeptide (e.g., a clade C gp140 polypeptide of the invention). Optimized viral polypeptide sequences are initially generated by modifying the amino acid sequence of one or more naturally-occurring viral gene products (e.g., peptides, polypeptides, and proteins) to increase the breadth, intensity, depth, or longevity of the antiviral immune response (e.g., cellular or humoral immune responses) generated upon immunization (e.g., when incorporated into a composition of the invention, e.g., vaccine of the invention) of a subject (e.g., a human). Thus, the optimized viral polypeptide may correspond to a "parent" viral gene sequence; alternatively, the optimized viral polypeptide may not correspond to a specific "parent" viral gene sequence but may correspond to analogous sequences from various strains or quasi-species of a virus. Modifications to the viral gene sequence that can be included in an optimized viral polypeptide include amino acid additions, substitutions, and deletions. In one embodiment of the invention, the optimized polypeptide is a 459C, 405C, or 939C gp140 polypeptide, or an optimized version thereof, which has been further altered to include a leader/signal sequence for maximal protein expression, a factor Xa site, and/or a foldon trimerization domain (see, e.g., SEQ ID NO: 8). An optimized polypeptide of the invention may, but need not, also include a cleavage site mutation(s). Methods of generating an optimized viral polypeptide are described in, e.g., Fisher et al. "Polyvalent Vaccine for Optimal Coverage of Potential T-Cell Epitopes in Global HIV-1 Variants," Nat. Med. 13(1):100-106 (2007) and International Patent Application Publication WO 2007/024941, herein incorporated by reference. Once the optimized viral polypeptide sequence is generated, the corresponding polypeptide can be produced or administered by standard techniques (e.g., recombinant viral vectors, such as the adenoviral vectors disclosed in International Patent Application Publications WO 2006/040330 and WO 2007/104792, herein incorporated by reference) and optionally assembled to form a stabilized polypeptide trimer.

By "pharmaceutically acceptable diluent, excipient, carrier, or adjuvant" is meant a diluent, excipient, carrier, or adjuvant which is physiologically acceptable to the subject while retaining the therapeutic properties of the pharmaceutical composition with which it is administered. One exemplary pharmaceutically acceptable carrier is physiological saline. Other physiologically acceptable diluents, excipients, carriers, or adjuvants and their formulations are known to one skilled in the art (see, e.g., U.S. Pub. No. 2012/0076812).

By "recombinant," with respect to a composition (e.g., a vector of the invention, such as an adenovirus or poxvirus vector), is meant a composition that has been manipulated in vitro (e.g., using standard cloning techniques) to introduce changes (e.g., changes to the composition, e.g., adenovirus or poxvirus genome of an adenovirus or poxvirus vector, respectively) that enable binding to or containment of a therapeutic agent and/or that promote the introduction of a therapeutic agent into a subject (e.g., a human) or a host cell. The recombinant composition of the invention may therefore be an adenoviral or poxviral transport vector (e.g., a replication-defective adenoviral or poxviral vector) for delivery of one or more of the stabilized clade C gp140 polypeptide trimers of the invention.

By "sequence identity" or "sequence similarity" is meant that the identity or similarity between two or more amino acid sequences, or two or more nucleotide sequences, is expressed in terms of the identity or similarity between the sequences. Sequence identity can be measured in terms of "percentage (%) identity," wherein the higher the percentage, the more identity shared between the sequences. Sequence similarity can be measured in terms of percentage similarity (which takes into account conservative amino acid substitutions); the higher the percentage, the more similarity shared between the sequences. Homologs or orthologs of nucleic acid or amino acid sequences possess a relatively high degree of sequence identity/similarity when aligned using standard methods. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

As used herein, the term "stabilized polypeptide trimer" or "stabilized trimer" refers, but is not limited to, an oligomer that includes a protein and/or polypeptide sequence that increases the stability (e.g., via the presence of one or more oligomerization domains) of the trimeric structure (e.g., reduces dissociation of a trimer into monomeric units). The stabilized polypeptide trimer, for example, may be a homotrimer composed of three optimized clade C gp140 polypeptides, for example, a trimer of three optimized 459C polypeptides each having an amino acid sequence of SEQ ID NO: 1; a trimer of three optimized 405C polypeptides each having an amino acid sequence of SEQ ID NO: 2; a trimer of three optimized 939C polypeptides each having an amino acid sequence of SEQ ID NO: 3; or variants thereof composed of three clade C gp140 polypeptides each having at least 90% identity (e.g., at least 91%, 92%, 93%, 94%, 95%, 96%, 97%, 98%, or 99% identity) to SEQ ID NO: 1, 2, or 3, wherein at least one gp140 protein includes an oligomerization domain. An "oligomerization domain" refers, but is not limited to, a polypeptide sequence that can be used to increase the stability of an oligomeric envelope protein such as, e.g., to increase the stability of a HIV gp140 trimer. Oligomerization domains can be used to increase the stability of homooligomeric polypeptides as well as heterooligomeric polypeptides. Oligomerization domains are well known in the art, and include "trimerization domains." A trimerization domain refers to an oligomerization domain that stabilizes trimeric polypeptides (e.g., trimers consisting of one or more of the gp140 polypeptides of the invention). Examples of trimerization domains include, but are not limited to, the T4-fibritin "foldon" trimerization domain; the coiled-coil trimerization domain derived from GCN4 (Yang et al. (2002) J. Virol. 76:4634); and the catalytic subunit of *E. coli* aspartate transcarbamoylase as a trimer tag (Chen et al. (2004) J. Virol. 78:4508).

A "subject" is a vertebrate, such as a mammal (e.g., a human). Mammals also include, but are not limited to, farm animals (such as cows), sport animals (e.g., horses), pets (such as cats and dogs), guinea pigs, rabbits, mice, and rats.

A subject to be treated according to the methods described herein (e.g., a subject having an HIV infection or a subject at risk of an HIV infection, e.g., a fetus of an HIV-1-infected pregnant female, a newborn having an HIV-1-infected mother, a person who has or has had a needlestick injury or sexual exposure to an HIV-1-infected individual) may be one who has been diagnosed by a medical practitioner as having such a condition. Diagnosis may be performed by any suitable means. A subject in whom the risk of an HIV infection is to be reduced or prevented may or may not have received such a diagnosis. One skilled in the art will understand that a subject to be treated according to the present invention may have been subjected to standard tests or may have been identified, without examination, as one at high risk due to the presence of one or more risk factors (e.g., a needle stick or known exposure to HIV or an HIV infected individual).

By "having substantially the sequence of" with respect to constructs of the invention is meant having at least 99% sequence identity to a recited reference sequence (e.g., having no more than 7 amino acid residue differences, e.g., 1, 2, 3, 4, 5, or 6 amino acid residue differences (e.g., additions, deletions, or conservative amino acid substitutions), relative to a recited reference sequence).

By "therapeutically effective amount" is meant an amount of a therapeutic agent that alone, or together with one or more additional (optional) therapeutic agents, produces beneficial or desired results upon administration to a mammal, such as a human. The therapeutically effective amount depends upon the context in which the therapeutic agent is applied. For example, in the context of administering a vaccine composition including a therapeutic agent such as a stabilized clade C gp140 trimer of the invention, the therapeutically effective amount of the vaccine composition is an amount sufficient to achieve a reduction in the level of HIV (e.g., as measured by a stabilization or decrease in HIV titer compared to a non-treated control), and/or an increase in the level of neutralizing anti-HIV antisera (e.g., as measured by an increase in serum neutralizing antibody levels relative to a non-treated control in a luciferase-based virus neutralization assay) as compared to a response obtained without administration of a composition of the invention (e.g., a vaccine composition), and/or to prevent the propagation of an infectious virus (e.g., HIV) in a subject (e.g., a human) having an increased risk of viral infection. Ideally, a therapeutically effective amount provides a therapeutic effect without causing a substantial cytotoxic effect in the subject. In general, a therapeutically effective amount of a composition administered to a subject (e.g., a human) will vary depending upon a number of factors associated with that subject, for example the overall health of the subject, the condition to be treated, or the severity of the condition. A therapeutically effective amount of a composition can be determined by varying the dosage of the product and measuring the resulting therapeutic response.

As used herein, and as well understood in the art, "treatment" is an approach for obtaining beneficial or desired results, such as clinical results. Beneficial or desired results can include, but are not limited to, alleviation or amelioration of one or more symptoms or conditions associated with a viral (e.g., retroviral, e.g., HIV, e.g., HIV-1) infection, including, without limitation, fever, muscle aches, coughing, sneezing, runny nose, sore throat, headache, chills, diarrhea, vomiting, rash, weakness, dizziness, bleeding under the skin, in internal organs, or from body orifices like the mouth, eyes, or ears, shock, nervous system malfunction, delirium, seizures, renal (kidney) failure, personality changes, neck stiffness, dehydration, seizures, lethargy, paralysis of the limbs, confusion, back pain, loss of sensation, impaired bladder and bowel function, and sleepiness that can progress into coma or death; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "vaccine," as used herein, is defined as material used to provoke an immune response (e.g., the production of neutralizing anti-HIV antisera). Administration of the vaccine to a subject may confer at least partial immunity against HIV infection.

The term "variant," as used herein, is meant a polypeptide having at least 90% identity (e.g., at least 91%, 92%, 93%, 94%, 95%, 96%, 97%, 98%, or 99% identity) to a reference polypeptide.

As used herein, the term "vector" is meant to include, but is not limited to, a virus (e.g., adenovirus or poxvirus), naked DNA, oligonucleotide, cationic lipid (e.g., liposome), cationic polymer (e.g., polysome), virosome, nanoparticle, or dentrimer. By "adenovirus vector" is meant a composition that includes one or more genes (non-structural or structural), or fragments thereof, from an adenoviral species (e.g., adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof (e.g., adenovirus serotype 5 HVR48 (Ad5HVR48))) that may be used to transmit one or more heterologous genes (e.g., one or more of the optimized clade C gp140 polypeptides of the invention) from a viral or non-viral source to a subject or a host. The nucleic acid material of the viral vector may be encapsulated, e.g., in a lipid membrane or by structural proteins (e.g., capsid proteins), that may include one or more viral polypeptides (e.g., an envelope glycoprotein). The viral vector can be used to infect cells of a subject, which, in turn, promotes the translation of the heterologous gene(s) of the viral vector into a protein product (e.g., one or more of the optimized clade C gp140 polypeptides described herein, such that a stabilized trimer of the invention is formed).

The term "virus," as used herein, is defined as an infectious agent that is unable to grow or reproduce outside a host cell and that infects mammals (e.g., humans) or birds.

Other features and advantages of the invention will be apparent from the following Detailed Description, the drawings, and the claims.

BRIEF DESCRIPTION OF THE DRAWINGS

The application file contains at least one drawing executed in color. Copies of this patent or patent application with color drawings will be provided by the Office upon request and payment of the necessary fee.

FIGS. 14A-14C are gel images and graphs showing acute clade C HIV-1 Env gp140 trimer expression, stability and homogeneity. FIG. 14A shows expression levels of novel, acute gp140 envelope protein sequences. Supernatant collected from 293T cells transiently transfected with HIV-1 Env gp140 sequences was assessed for protein expression by western blot. FIG. 14B shows Coomassie stained SDS-PAGE gel of pooled peaks of acute, clade C trimers after a single freeze/thaw cycle or incubation at 4° C. for two weeks. Trimers are as follows for both SDS-PAGE gels: (1) C97ZA012, (2) 405C, (3) 459C, (4) 939C gp140. FIG. 14C shows gel filtration chromatography traces of 459C, 405C, and 939C gp140 trimers as run on a Superose 6 column. Molecular weight standards for traces include thyoglobin (670 kDa), ferritin (440 kDa), and γ-globin (158 kDa).

FIG. 15A shows a phylogenetic tree comparing each of the four, clade C vaccine envelope (Env) sequences to 489 clade C sequences sampled starting from the year 2004. Country of origin for each sequence shaded according to the key provided containing two letter abbreviations for each country. FIG. 15B shows a phylogenetic tree comparing each of the four clade C vaccine Env sequences to 506 clade C sequences from South Africa starting from the year 2000. Year of origin is shaded according to the key provided. For FIGS. 15A and 15B, vaccine Env strains, consensus clade C Env sequence, and HXB2 (out group) are indicated. FIG. 15C shows an alignment of CD4 binding site contact residues for clade C immunogens, FIG. 15D shows an alignment of PG9 contact residues for clade C immunogens. FIG. 15E shows an alignment of V3 loop and C-terminal glycan contact residues for clade C immunogens. For FIGS. 15C-15E, sequence alignments compared to a consensus C sequence and aligned using HXB2 numbering, ranking of sequence centrality denoted by numbers to the right, 1 being most central and 4 being least central.

FIG. 16A shows that soluble two-domain CD4 was irreversibly coupled to a CM5 chip, 459C, 405C, or 939C gp140 was flowed over the chip at concentrations of 62.5-1000 nM. FIGS. 16B-16D show that Protein A was irreversibly coupled to a CM5 chip; FIG. 16B further shows that 17b IgG was captured. HIV-1 Env 459C, 405C, or 939C gp140 was flowed over the bound IgG at a concentration of 1000 nM in the presence or absence of CD4 bound to the immunogen. 17b binding alone in red, CD4 coupled to trimer binding to 17b IgG in blue. FIGS. 16C and 16D show that VRCO1 and 3BNC117 IgG, respectively, were captured; HIV-1 Env 459C, 405C, and 939C gp140 trimer were flowed over the bound IgG at concentrations of 62.5-1000 nM. Sensorgrams are presented in black, kinetic fits in gray. RU, response units.

In FIG. 17A, HIV-1 Env 459C, 405C, and 939C gp140 trimers were flowed over bound PGT126 IgG at concentrations of 62.5-1000 nM. In FIG. 17B, HIV-1 Env 459C, 405C, and 939C gp140 trimers were flowed over bound PGT121 IgG at concentrations of 62.5-1000 nM. In FIG. 17C, HIV-1 Env 459C, 405C, and 939C gp140 trimers were flowed over bound 10-1074 IgG at concentrations of 62.5-1000 nM. Sensorgrams presented in black, kinetic fits in gray. RU, response units.

FIG. 19A shows the vaccination scheme for all vaccinated guinea pigs. Animals vaccinated at weeks 0, 4, and 8 and bled at weeks 0, 4, 8, and 12. FIG. 19B shows binding antibody titers from guinea pig sera against gp140 antigens after vaccination with clade C trimeric immunogen. Sera were tested in endpoint ELISAs against a panel of trimeric antigens in guinea pigs vaccinated with HIV-1 Env C97ZA012, 459C, 405C, and 939C gp140 trimeric protein immunogens. 2C Mixture–C97ZA012+459C gp140; 3C Mixture–C97ZA012+459C+405C gp140; 4C 423" Mixture–C97ZA012+405C+459C+939C gp140. Shades correspond to coating proteins as listed in figure. Dotted line indicates background.

FIG. 20A shows the results for clade C in the TZM.bl neutralization assay. FIG. 20B shows the results for clade B in the TZM.bl neutralization assay. FIG. 20C shows the results for clade A in the TZM.bl neutralization assay. Horizontal bars indicate median titers, dotted line indicates limit of detection for the assay. X-axis immunogen names refer to vaccination regimen. 'C97' is HIV-1 Env C97ZA012 gp140, '2C' includes HIV-1 Env C97ZA012+459C gp140, '3C' includes HIV-1 Env C97ZA012+459C+405C gp140, '4C' includes HIV-1 Env C97ZA012+459C+405C+939C gp140 trimeric immunogens. *P<0.05 Mann-Whitney U pairwise comparisons to the 4C mixture.

FIGS. 21A-21C are graphs showing statistical comparison of titers of neutralizing antibodies elicited by vaccination regimens including clade C trimers as measured by the TZM.bl neutralization assay. FIG. 21A shows the geometric mean titer of neutralizing antibodies against pseudovirions grouped by vaccination regimen. Pseudovirions denoted by different shades as shown in the included key. FIG. 21B shows the geometric mean titer of neutralizing antibodies against pseudovirions grouped by clade of pseudovirion neutralized and by vaccination regimen. Cutoffs for positivity is post-3*pre. FIG. 21C shows a heat map illustration of the clustering of responses from guinea pigs vaccinated with clade C trimers. Responses for cutoff defined as (Post-Pre*3). Clade of pseudovirion and vaccination regimen denoted by shades in key.

DETAILED DESCRIPTION OF THE INVENTION

Figure 1:
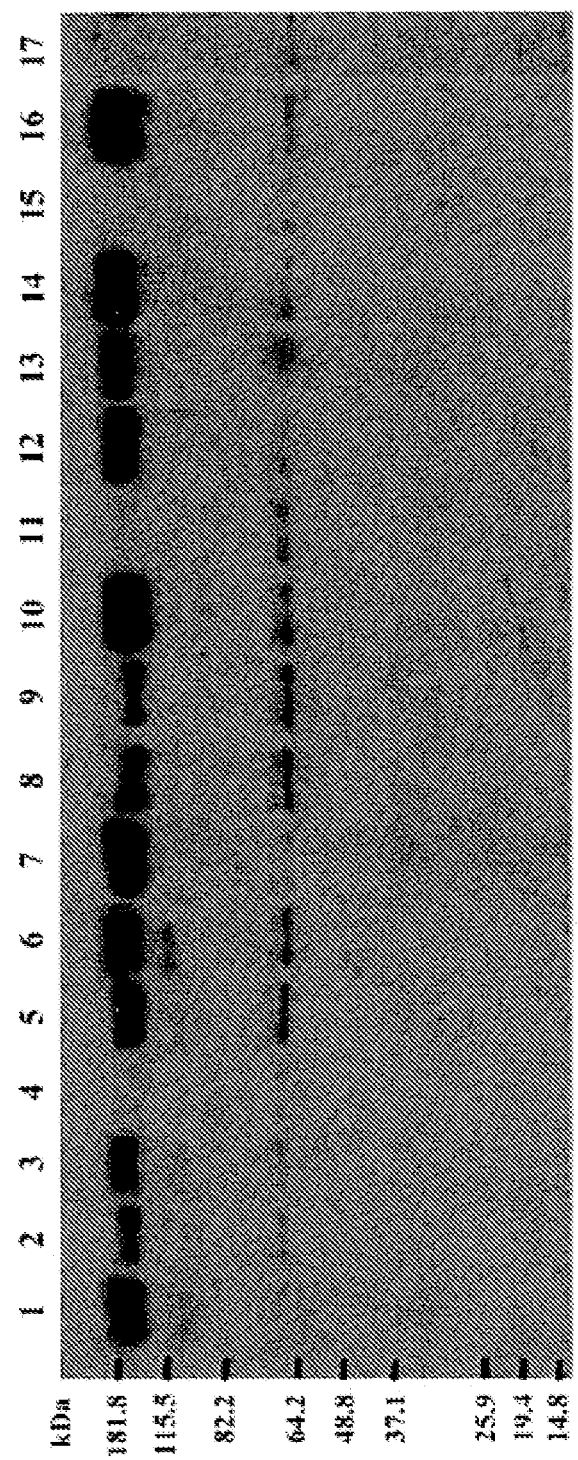
FIG. 1 is a Western blot showing the relative expression levels of novel, acute gp140-foldon (gp140Fd) envelope protein sequences. Supernatant collected from 293T cells transiently transfected with lipofectamine and a pCMV vector containing each of the gp140Fd sequences was assessed for protein expression. Lanes are of each sample's expression levels are as follows: (1) 939C, (2) 426C, (3) 756C, (4) 590C, (5) 349C, (6) 823C, (7) 823cD6, (8) 072C, (9) 327C, (10) 405C, (11) 431C, (12) 459C, (13) 885C, (14) 706C, (15) 140C, (16) C97ZA012 (C97), and (17) pCMV vector only.

Most antibodies induced by human immunodeficiency virus (HIV) (e.g., HIV type 1 (HIV-1)) are ineffective at preventing initiation or spread of infection, as they are either non-neutralizing or narrowly isolate-specific. One of the biggest challenges in HIV vaccine development is to design a HIV envelope immunogen that can induce protective, neutralizing antibodies effective against the diverse HIV strains that characterize the global pandemic. Indeed, the generation of "broadly neutralizing" antibodies that recognize relatively conserved regions on the envelope glycoprotein are rare. For example, difficulties in generating broadly neutralizing antibodies (bNAbs) arise from the extensive sequence diversity of circulating strains of HIV-1 (Gaschen, *Science* 296:2354-2360, 2002). As the HIV-1 Env protein is the sole viral antigen on the surface of the virus, it is the target for NAbs. HIV-1 Env is a trimer (gp160). Each trimer includes a gp120 surface subunit, which is responsible for interacting with the primary receptor, CD4, and the secondary receptors, CCR5 and/or CXCR4, as well as a gp41 transmembrane subunit, which is responsible for membrane fusion. The present invention is based in part on the discovery of stabilized trimeric HIV clade C envelope (Env) proteins and combinations thereof that elicit a surprisingly broad neutralizing antibody response in vivo.

Clade C Gp140 Env Polypeptides and Stabilized Trimers of the Invention

The invention features novel HIV clade C gp140 Env polypeptides. Soluble Env gp140 trimers, as compared to Env gp120 monomers, more closely mimic the antigenic properties of circulating virions, and generate more robust neutralizing antibody responses. Polypeptides of the invention include, for example, an optimized polypeptide including (a) an amino acid sequence having at least 90% identity (e.g., at least 91%, 92%, 93%, 94%, 95%, 96%, 97%, 98%, 99%, or 100% identity) to SEQ ID NO: 1 (459C gp140-foldon (gp140Fd) polypeptide); an amino acid sequence having at least 90% identity (e.g., at least 91%, 92%, 93%, 94%, 95%, 96%, 97%, 98%, 99%, or 100% identity) to SEQ ID NO: 2 (405C gp140Fd polypeptide); or (c) an amino acid sequence having at least 90% identity (e.g., at least 91%, 92%, 93%, 94%, 95%, 96%, 97%, 98%, 99%, or 100% identity) to SEQ ID NO: 3 (939C gp140Fd polypeptide).

The invention also features stabilized HIV clade C gp140 Env polypeptide trimers. Stabilized trimers of the invention feature optimized clade C gp140 Env polypeptides, such as the novel clade C gp140 polypeptides of the invention described above. These polypeptides may have, or may be modified to include, one or more of the following domains and/or mutations. A clade C gp140 Env polypeptide constituent of a stabilized trimer of the invention may include a T4-fibritin "foldon" trimerization domain sequence to support stable trimer formation. Such optimized clade C gp140 Env polypeptides include the 459C gp140-foldon (gp140Fd) polypeptide (SEQ ID NO: 1), 405C gp140Fd polypeptide (SEQ ID NO: 2), 939C gp140Fd polypeptide (SEQ ID NO: 3), and variants thereof, which each include a C-terminal trimerization domain. The optimized gp140 Env polypeptides may also include cleavage site mutations to enhance stability, for example, by eliminating cleavage by a peptidase. The optimized gp140 Env polypeptides may additionally have a signal/leader sequence to maximize protein expression. Further, the optimized gp140 Env polypeptides may include a Factor Xa cleavage site (SRIEGR), which may, for example, be incorporated upstream of (N-terminal to) the trimerization domain. As discussed herein below, the stabilized trimers of the invention are preferably homotrimers (e.g., trimers composed of three identical polypeptides). Heterotrimers (e.g., trimers composed of three polypeptides that are not all identical) of the invention are also envisioned.

The stabilized trimers of the invention are preferably stabilized homotrimers that include, for example, three gp140 polypeptides, wherein each of the gp140 polypeptides includes an amino acid sequence having at least 90% identity (e.g., at least 91%, 92%, 93%, 94%, 95%, 96%, 97%, 98%, or 99% identity) to, or the sequence of, SEQ ID NO: 1 (459C gp140Fd), SEQ ID NO: 2 (405C gp140Fd), or SEQ ID NO: 3 (939C gp140Fd). The invention also features stabilized homotrimers including three gp140 polypeptides, wherein each of said gp140 polypeptides includes an amino acid sequence having substantially the sequence of (e.g., 99% or more identity), or the sequence of, SEQ ID NO: 1 (459C gp140Fd), SEQ ID NO: 2 (405C gp140Fd), or SEQ ID NO: 3 (939C gp140Fd). Exemplary homotrimers of the invention include Trimers 1, 2, and 3 in Table 1 below.

Alternatively, the stabilized trimer of the invention may be a stabilized heterotrimer. For example, the stabilized trimer may be a stabilized heterotrimer that includes a combination of two different clade C gp140 sequences (e.g., SEQ ID NO: 1 and SEQ ID NO: 2; SEQ ID NO: 1 and SEQ ID NO: 3; SEQ ID NO: 2 and SEQ ID NO: 3), such as Trimers 4-9 in Table 1 below. In some instances, the stabilized trimer may be a stabilized heterotrimer that includes a combination of three different clade C gp140 sequences (e.g., SEQ ID NO: 1, SEQ ID NO: 2, and SEQ ID NO: 3), such as Trimer 10 in Table 1 below.

TABLE 1

Optimized Clade C gp140 Trimers of the Invention

| Exemplary Trimer | Constituent Polypeptides | | |
|---|---|---|---|
| | Polypeptide 1 | Polypeptide 2 | Polypeptide 3 |
| Trimer 1 | SEQ ID NO: 1 | SEQ ID NO: 1 | SEQ ID NO: 1 |
| Trimer 2 | SEQ ID NO: 2 | SEQ ID NO: 2 | SEQ ID NO: 2 |
| Trimer 3 | SEQ ID NO: 3 | SEQ ID NO: 3 | SEQ ID NO: 3 |
| Trimer 4 | SEQ ID NO: 1 | SEQ ID NO: 2 | SEQ ID NO: 2 |
| Trimer 5 | SEQ ID NO: 1 | SEQ ID NO: 1 | SEQ ID NO: 2 |
| Trimer 6 | SEQ ID NO: 1 | SEQ ID NO: 3 | SEQ ID NO: 3 |
| Trimer 7 | SEQ ID NO: 1 | SEQ ID NO: 1 | SEQ ID NO: 3 |
| Trimer 8 | SEQ ID NO: 2 | SEQ ID NO: 3 | SEQ ID NO: 3 |
| Trimer 9 | SEQ ID NO: 2 | SEQ ID NO: 2 | SEQ ID NO: 3 |
| Trimer 10 | SEQ ID NO: 1 | SEQ ID NO: 2 | SEQ ID NO: 3 |

Stabilized Clade C Gp140 Env Trimer Compositions of the Invention

Any one of the stabilized clade C gp140 Env trimers of the invention, such as those described above, can be included in compositions (e.g., pharmaceutical compositions). Accordingly, the invention features a composition including at least one of the optimized clade C gp140 Env trimers described above (e.g., at least 1, 2, 3, 4, or more different types of optimized clade C gp140 Env trimers may be included in a single composition or vaccine). For example, the composition may be a monovalent composition including only optimized clade C 459C trimers (e.g., stabilized 459C homotrimers of the invention having three polypeptides each including the amino acid sequence of SEQ ID NO: 1, or a variant thereof having at least 90% identity (e.g., at least 91%, 92%, 93%, 94%, 95%, 96%, 97%, 98%, or 99% identity) to SEQ ID NO: 1), only optimized clade C 405C trimers (e.g., stabilized 405C homotrimers of the invention having three polypeptides each including the amino acid sequence of SEQ ID NO: 2, or a variant thereof having at least 90% identity (e.g., at least 91%, 92%, 93%, 94%, 95%, 96%, 97%, 98%, or 99% identity) to SEQ ID NO: 2), or only optimized clade C 939C trimers (e.g., stabilized 939C homotrimers of the invention having three polypeptides each including the amino acid sequence of SEQ ID NO: 3, or a variant thereof having at least 90% identity (e.g., at least 91%, 92%, 93%, 94%, 95%, 96%, 97%, 98%, or 99% identity) to SEQ ID NO: 3).

In other examples, the composition may be a multivalent composition (e.g., a bivalent, trivalent, or quadrivalent composition) including two or more different types of optimized clade C trimers. For example, the composition may be a bivalent composition including two different types of optimized clade C gp140 trimers of the invention (e.g., a 459C homotrimer and a 405C homotrimer; a 459C homotrimer and a 939C homotrimer; or a 405C homotrimer and a 939C homotrimer). Alternatively, the bivalent composition may include one optimized clade C gp140 trimer of the invention (e.g., a 459C homotrimer, a 405C homotrimer, or a 939C homotrimer) and another optimized gp140 trimer (e.g., a stabilized C97ZA012 (C97) trimer, such as a C97 gp140 trimer wherein at least one or two of the gp140 polypeptides, and preferably each of the three gp140 polypeptides, includes an amino acid sequence having at least 90% identity (e.g., at least 91%, 92%, 93%, 94%, 95%, 96%, 97%, 98%, or 99% identity) to, or the sequence of, SEQ ID NO: 7). The composition can also include a homotrimer or a heterotrimer described in U.S. provisional application Ser. No. 61/749,737, incorporated herein by reference.

In some examples, the multivalent composition is a trivalent composition including three different types of optimized clade C gp140 trimers of the invention (e.g., 459C, 405C, and 939C homotrimers). Alternatively, the trivalent composition may include one or two optimized clade C gp140 trimers of the invention and two or one other optimized gp140 trimers (including, e.g., a stabilized C97 trimer, such as a C97 gp140 trimer wherein at least one or two of the gp140 polypeptides, and preferably each of the three gp140 polypeptides, includes an amino acid sequence having at least 90% identity (e.g., at least 91%, 92%, 93%, 94%, 95%, 96%, 97%, 98%, or 99% identity) to, or the sequence of, SEQ ID NO: 7), respectively. The composition can also include a homotrimer or a heterotrimer described in U.S. provisional application Ser. No. 61/749,737, incorporated herein by reference.

In some examples, the multivalent composition is a quadrivalent composition including four different types of optimized clade C gp140 trimers, such as a composition which includes 459C, 405C, and 939C homotrimers of the invention in combination with another optimized gp140 trimer, such as a stabilized C97 trimer, e.g., a C97 gp140 trimer wherein at least one or two of the gp140 polypeptides, and preferably each of the three gp140 polypeptides, includes an amino acid sequence having at least 90% identity (e.g., at least 91%, 92%, 93%, 94%, 95%, 96%, 97%, 98%, or 99% identity) to, or the sequence of, SEQ ID NO: 7) ("QuadC mixture"). The composition can also include a homotrimer or a heterotrimer described in U.S. provisional application Ser. No. 61/749,737, incorporated herein by reference.

In yet other examples, the composition may be a monovalent or multivalent composition including one or more heterotrimers (e.g., Trimers 4-10 in Table 1 above) of the invention.

Any one of the compositions of the invention may further include a pharmaceutically acceptable carrier, excipient, or diluent, and/or an adjuvant.

Stabilized Clade C Gp140 Env Trimer Vaccines of the Invention

The invention features vaccines including at least one of the compositions of the invention described herein. The vaccine may be used for treating or reducing the risk of a human immunodeficiency virus (HIV) infection in a subject in need thereof. For example, the vaccine may elicit production of neutralizing anti-HIV antisera (e.g., neutralizing anti-HIV-1 antisera) after administration to the subject. The anti-HIV antisera may also be able to neutralize HIV (e.g., HIV-1), for example, selected from any one or more of clade A, clade B, and clade C.

Nucleic Acid Molecules of the Invention

In some embodiments, the vaccines of the invention include one or more nucleic acid molecules of the invention, such as a nucleic acid molecule having a nucleotide sequence that encodes a clade C gp140 polypeptide, in which the clade C gp140 polypeptide includes: (a) an amino acid sequence having at least 90% identity (e.g., at least 91%, 92%, 93%, 94%, 95%, 96%, 97%, 98%, 99%, or 100% identity) to SEQ ID NO: 1; (b) an amino acid sequence having at least 90% identity (e.g., at least 91%, 92%, 93%, 94%, 95%, 96%, 97%, 98%, 99%, or 100% identity) to SEQ ID NO: 2; (c) an amino acid sequence having at least 90% identity (e.g., at least 91%, 92%, 93%, 94%, 95%, 96%, 97%, 98%, 99%, or 100% identity) to SEQ ID NO: 3, and/or combinations thereof. As discussed below, vectors (e.g., viral vectors, such as an adenovirus or poxvirus vector) of the invention can include one or more of these nucleic acid molecules. Accordingly, vaccines of the invention may include one or more of these vectors. The stabilized clade C gp140 Env trimer polypeptides of the invention, as well as vaccines, nucleic acids, and vectors that incorporate one or more optimized clade C gp140 Env polypeptides, can be recombinantly expressed in a cell or organism, or can be directly administered to a subject (e.g., a human) infected with, or at risk of becoming infected with, HIV (e.g., HIV-1).

Vectors of the Invention

As noted above, the invention features vectors including one or more of the nucleic acid molecules of the invention. The vector can be, for example, a carrier (e.g., a liposome), a plasmid, a cosmid, a yeast artificial chromosome, or a virus (e.g., an adenovirus vector or a poxvirus vector) that includes one or more of the nucleic acid molecules of the invention.

An adenovirus vector of the invention can be derived from a recombinant adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof (e.g., adenovirus serotype 5 HVR48 (Ad5HVR48)). A poxvirus vector of the invention may be derived, for example, from modified vaccinia virus Ankara (MVA). These vectors can include additional nucleic acid sequences from several sources.

Vectors of the invention can be constructed using any recombinant molecular biology technique known in the art. The vector, upon transfection or transduction of a target cell or organism, can be extrachromosomal or integrated into the host cell chromosome. The nucleic acid component of a vector can be in single or multiple copy number per target cell, and can be linear, circular, or concatamerized. The vectors can also include internal ribosome entry site (IRES) sequences to allow for the expression of multiple peptide or polypeptide chains from a single nucleic acid transcript (e.g., a polycistronic vector, e.g., a bi- or tri-cistronic vector).

Vectors of the invention can also include gene expression elements that facilitate the expression of the encoded polypeptide(s) of the invention (e.g., SEQ ID NOs: 1 (459C gp140Fd), 2 (405C gp140Fd), and/or 3 (939C gp140Fd) or polypeptides having amino acids sequences with at least 90%, 91%, 92%, 93%, 94%, 95%, 96%, 97%, 98%, or 99% sequence identity to SEQ ID NO: 1, 2, or 3). Gene expression elements include, but are not limited to, (a) regulatory sequences, such as viral transcription promoters and their enhancer elements, such as the SV40 early promoter, Rous sarcoma virus LTR, and Moloney murine leukemia virus LTR; (b) splice regions and polyadenylation sites such as those derived from the SV40 late region; and (c) polyadenylation sites such as in SV40. Also included are plasmid origins of replication, antibiotic resistance or selection genes, multiple cloning sites (e.g., restriction enzyme cleavage loci), and other viral gene sequences (e.g., sequences encoding viral structural, functional, or regulatory elements, such as the HIV long terminal repeat (LTR)).

Exemplary vectors are described below.

Adenovirus Vectors

Recombinant adenoviruses offer several significant advantages for use as vectors for the expression of, for example, one or more of the optimized clade C gp140 Env polypeptides of the invention. The viruses can be prepared to high titer, can infect non-replicating cells, and can confer high-efficiency transduction of target cells following contact with a target cell population, tissue, or organ (e.g., in vivo, ex vivo, or in vitro). Furthermore, adenoviruses do not integrate their DNA into the host genome. Thus, their use as an expression vector has a reduced risk of inducing spontaneous proliferative disorders. In animal models, adenoviral vectors have generally been found to mediate high-level expression for approximately one week. The duration of transgene expression (e.g., expression of a nucleic acid molecule of the invention) from an adenovirus vector can be prolonged by using, for example, cell or tissue-specific promoters. Other improvements in the molecular engineering of the adenovirus vector itself have produced more sustained transgene expression and less inflammation. This is seen with so-called "second generation" vectors harboring specific mutations in additional early adenoviral genes and "gutless" vectors in which virtually all the viral genes are deleted utilizing a Cre-Lox strategy (Engelhardt et al., *Proc. Natl. Acad. Sci. USA* 91:6196 (1994) and Kochanek et al., *Proc. Natl. Acad. Sci. USA* 93:5731 (1996), each herein incorporated by reference).

The rare serotype and chimeric adenoviral vectors disclosed in International Patent Application Publications WO 2006/040330 and WO 2007/104792, each incorporated by reference herein, are particularly useful as vectors of the invention. For example, recombinant adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof (e.g., adenovirus serotype 5 HVR48 (Ad5HVR48) can encode and/or deliver one or more of the optimized clade C gp140 Env polypeptides of the invention to facilitate formation and presentation of gp140 Env trimer formation. In some embodiments, one or more recombinant adenovirus vectors can be administered to the subject in order to express the clade C gp140 Env polypeptides for formation of stabilized trimers of the invention.

Adeno-Associated Virus (AAV) Vectors

Adeno-associated viruses (AAV), derived from non-pathogenic parvoviruses, can also be used to facilitate delivery and/or expression of one or more of the optimized clade C gp140 Env polypeptides of the invention. These vectors evoke almost no anti-vector cellular immune response and produce transgene expression lasting months in most experimental systems.

Stabilized trimers of the invention may be produced upon expression of the clade C gp140 Env polypeptides described herein using an AAV vector that includes a nucleic acid molecule of the invention that encodes one or more (e.g., 1, 2, or 3 or more) clade C gp140 Env polypeptide(s).

Retrovirus Vectors

Retroviruses are useful for the expression of optimized clade C gp140 Env polypeptides of the invention. Unlike adenoviruses, the retroviral genome is based in RNA. When a retrovirus infects a cell, it will introduce its RNA together with several enzymes into the cell. The viral RNA molecules from the retrovirus will produce a double-stranded DNA copy, called a provirus, through a process called reverse transcription. Following transport into the cell nucleus, the proviral DNA is integrated in a host cell chromosome, permanently altering the genome of the transduced cell and any progeny cells that may derive from this cell. The ability to permanently introduce a gene into a cell or organism is the defining characteristic of retroviruses used for gene therapy. Retroviruses, which include lentiviruses, are a family of viruses including human immunodeficiency virus (HIV) that includes several accessory proteins to facilitate viral infection and proviral integration. Current "third-generation" lentiviral vectors feature total replication incompetence, broad tropism, and increased gene transfer capacity for mammalian cells (see, e.g., Mangeat and Trono, *Human Gene Therapy* 16(8):913 (2005) and Wiznerowicz and Trono, *Trends Biotechnol.* 23(1):42 (2005), each herein incorporated by reference).

Stabilized trimers of the invention may be produced upon expression of the clade C gp140 Env polypeptides described herein using a retrovirus vector that includes a nucleic acid molecule of the invention that encodes one or more (e.g., 1, 2, or 3 or more) clade C gp140 Env polypeptide(s).

Other Viral Vectors

Besides adenoviral and retroviral vectors, other viral vectors and techniques are known in the art that can be used to facilitate delivery and/or expression of one or more of the optimized clade C gp140 Env polypeptides of the invention in a cell (e.g., a blood cell, such as a lymphocyte) or subject (e.g., a human) in order to promote formation of the trimers of the invention. These viruses include poxviruses (e.g., vaccinia virus and modified vaccinia virus Ankara (MVA); see, e.g., U.S. Pat. Nos. 4,603,112 and 5,762,938, each incorporated by reference herein), herpesviruses, togaviruses (e.g., Venezuelan Equine Encephalitis virus; see, e.g., U.S. Pat. No. 5,643,576, incorporated by reference herein), picornaviruses (e.g., poliovirus; see, e.g., U.S. Pat. No. 5,639,649, incorporated by reference herein), baculoviruses, and others described by Wattanapitayakul and Bauer (Biomed. Pharmacother. 54:487 (2000), incorporated by reference herein).

Naked DNA and Oligonucleotides Naked DNA or oligonucleotides encoding one or more of the optimized clade C gp140 Env polypeptides of the invention can also be used to express these polypeptides in a cell or a subject (e.g., a human) in order to promote formation of the trimers of the invention. See, e.g., Cohen, *Science* 259:1691-1692 (1993); Fynan et al., *Proc. Natl. Acad. Sci. USA,* 90:11478 (1993); and Wolff et al., Bio Techniques 11:474485 (1991), each herein incorporated by reference. This is the simplest method of non-viral transfection. Efficient methods for delivery of naked DNA exist, such as electroporation and the use of a "gene gun," which shoots DNA-coated gold particles into a cell using high pressure gas and carrier particles (e.g., gold).

Lipoplexes and Polyplexes

To improve the delivery of a nucleic acid encoding one or more of the optimized clade C gp140 Env polypeptides of the invention into a cell or subject in order to promote formation of the trimers of the invention, lipoplexes (e.g., liposomes) and polyplexes can be used to protect the nucleic acid from undesirable degradation during the transfection process. The nucleic acid molecules can be covered with lipids in an organized structure like a micelle or a liposome. When the organized structure is complexed with the nucleic acid molecule it is called a lipoplex. There are three types of lipids: anionic (negatively-charged), neutral, or cationic (positively-charged). Lipoplexes that utilize cationic lipids have proven utility for gene transfer. Cationic lipids, due to their positive charge, naturally complex with the negatively-charged nucleic acid. Also as a result of their charge they interact with the cell membrane, endocytosis of the lipoplex occurs, and the nucleic acid is released into the cytoplasm. The cationic lipids also protect against degradation of the nucleic acid by the cell.

Complexes of polymers with nucleic acids are called polyplexes. Most polyplexes consist of cationic polymers and their production is regulated by ionic interactions. One large difference between the methods of action of polyplexes and lipoplexes is that polyplexes cannot release their nucleic acid load into the cytoplasm, so, to this end, co-transfection with endosome-lytic agents (to lyse the endosome that is made during endocytosis), such as inactivated adenovirus, must occur. However, this is not always the case; polymers, such as polyethylenimine, have their own method of endosome disruption, as does chitosan and trimethylchitosan.

Exemplary cationic lipids and polymers that can be used in combination with one or more of the nucleic acid molecules encoding one or more of the optimized clade C gp140 Env polypeptides of the invention to form lipoplexes or polyplexes include, but are not limited to, polyethylenimine, lipofectin, lipofectamine, polylysine, chitosan, trimethylchitosan, and alginate.

Hybrid Methods

Several hybrid methods of gene transfer combine two or more techniques. Virosomes, for example, combine lipoplexes (e.g., liposomes) with an inactivated virus. This approach has been shown to result in more efficient gene transfer in respiratory epithelial cells compared to either viral or liposomal methods alone. Other methods involve mixing other viral vectors with cationic lipids or hybridizing viruses. Each of these methods can be used to facilitate transfer of one or more of the nucleic acid molecules of the invention encoding one or more of the optimized clade C gp140 Env polypeptides of the invention into a cell or subject in order to promote formation of the trimers of the invention.

Dendrimers

Dendrimers may be also be used to transfer one or more of the nucleic acid molecules of the invention encoding one or more of the optimized clade C gp140 Env polypeptide(s) of the invention into a cell or subject in order to promote formation of the trimers of the invention. A dendrimer is a highly branched macromolecule with a spherical shape. The surface of the particle may be functionalized in many ways, and many of the properties of the resulting construct are determined by its surface. In particular, it is possible to construct a cationic dendrimer (i.e., one with a positive surface charge). When in the presence of genetic material (e.g., a nucleic acid molecule of the invention), charge complimentarity leads to a temporary association of the nucleic acid with the cationic dendrimer. On reaching its destination the dendrimer-nucleic acid complex is then taken into the cell via endocytosis, resulting in the subsequent expression of one or more of the optimized clade C gp140 Env polypeptide(s) of the invention.

Methods of Treatment Using the Compositions of the Invention

In Vivo Administration

The invention features methods for the in vivo administration of a therapeutically effective amount of one or more of the compositions (e.g., vaccines, vectors, stabilized trimer(s), nucleic acids, or other composition thereof described herein) of the invention to a subject (e.g., a human, e.g., a human infected with HIV or a human at risk of an HIV infection) in need thereof. Upon administering one or more of the compositions of the invention to the subject, the stabilized trimers of the invention can elicit protective or therapeutic immune responses (e.g., cellular or humoral immune responses, e.g., neutralizing anti-HIV antisera production, e.g., anti-HIV antisera that neutralizes HIV selected from clade A, clade B, and/or clade C HIV) directed against the viral immunogens.

The method may be used to treat or reduce the risk of an HIV infection (e.g., an HIV-1 infection) in a subject in need thereof. The subject may be infected with HIV (e.g., HIV-1) or may be at risk of exposure to HIV (e.g., HIV-1). The compositions of the invention can be administered to a subject infected with HIV to treat AIDS. Examples of symptoms of diseases caused by a viral infection, such as AIDS, that can be treated using the compositions of the invention include, for example, fever, muscle aches, coughing, sneezing, runny nose, sore throat, headache, chills, diarrhea, vomiting, rash, weakness, dizziness, bleeding under the skin, in internal organs, or from body orifices like the mouth, eyes, or ears, shock, nervous system malfunction, delirium, seizures, renal (kidney) failure, personality changes, neck stiffness, dehydration, seizures, lethargy, paralysis of the limbs, confusion, back pain, loss of sensation, impaired bladder and bowel function, and sleepiness that can progress into coma or death. These symptoms, and their resolution during treatment, may be measured by, for example, a physician during a physical examination or by other tests and methods known in the art.

In cases in which the subject is infected with HIV, the method may be used to reduce an HIV-mediated activity (e.g., infection, fusion (e.g., target cell entry and/or syncytia formation), viral spread, etc.) and/or to decrease HIV titer in the subject. HIV-mediated activity and/or HIV titer may be decreased, for example, by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control subject (e.g., an untreated subject or a subject treated with a placebo). In some instances, the method can result in a reduced HIV titer as measured by a reduction of proviral DNA level in tissue of the subject relative to an amount of proviral DNA level in tissue of the subject before treatment, an untreated subject, or a subject treated with a placebo. For example, the proviral DNA level in tissue (e.g., lymph node tissue, gastrointestinal tissue, and/or peripheral blood) may be reduced to below about 1,000 DNA copies/$10^6$ cells (e.g., below about 100 DNA copies/$10^6$ cells, e.g., below about 10 DNA copies/$10^6$ cells, e.g., below about 1 DNA copy/$10^6$ cells). In some instances, the method can result in a reduced HIV titer as measured by a reduction of plasma viral load of the subject relative to an amount of plasma viral load of the subject before treatment, an untreated subject, or a subject treated with a placebo. For example, plasma viral load may be reduced to less than 3,500 RNA copies/ml (e.g., less than 2,000 RNA copies/ml, e.g., less than 400 RNA copies/ml, e.g., less than 50 RNA copies/ml, e.g., less than 1 RNA copy/ml).

One or more of the compositions of the invention may also be administered in the form of a vaccine for prophylactic treatment of a subject (e.g., a human) at risk of an HIV infection.

The compositions utilized in the methods described herein can be formulated, for example, for administration intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions.

The preferred method of administration can vary depending on various factors (e.g., the components of the composition being administered and the severity of the condition being treated). Formulations suitable for oral or nasal administration may consist of liquid solutions, such as an effective amount of the composition dissolved in a diluent (e.g., water, saline, or PEG-400), capsules, sachets, tablets, or gels, each containing a predetermined amount of the chimeric Ad5 vector composition of the invention. The pharmaceutical composition may also be an aerosol formulation for inhalation, for example, to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, for example, an aerosol containing sorbitan trioleate or oleic acid, for example, together with trichlorofluoromethane, dichlorofluoromethane, dichlorotetrafluoroethane, or any other biologically compatible propellant gas.

Immunogenicity of the composition of the invention may be significantly improved if it is co-administered with an immunostimulatory agent or adjuvant. Suitable adjuvants well-known to those skilled in the art include, for example, aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

Compositions according to the invention described herein may be formulated to release the composition immediately upon administration (e.g., targeted delivery) or at any predetermined time period after administration using controlled or extended release formulations. Administration of the composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release (e.g., the gastrointestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, for example, appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The compositions of the invention may be administered to provide pre-infection prophylaxis or after a subject has been diagnosed with an HIV infection or a disease with an etiology traceable to an HIV infection (e.g., AIDS). The composition may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-infection or pre-diagnosis, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, or 20 years or longer post-diagnosis or post-infection to HIV. The subject can be administered a single dose of the composition(s) (or, e.g., 2, 3, 4, 5, 6, 7, 8, 9, 10, or more doses) or the subject can be administered at least one dose (e.g., 1, 2, 3, 4, 5, 6, 7, 8, 9, 10, or more doses) daily, weekly, monthly, or yearly. The administration period may be defined (e.g., 1-4 weeks, 1-12 months, 1-20 years) or may be for the life of the subject. The composition(s) may also be administered to said subject as a prime or a boost composition or in a prime-boost regimen. In a preferred embodiment, the composition (e.g., vaccine) of the invention is administered as a boost following administration of an additional composition (e.g., vaccine) as a prime. The prime and/or the boost in this regimen may include one or more of the composition(s) of the invention (e.g., any one of the stabilized trimers, the compositions, the vaccines, the nucleic acid molecules, and/or the vectors of the invention).

When treating disease (e.g., AIDS), the compositions of the invention may be administered to the subject either before the occurrence of symptoms or a definitive diagnosis or after diagnosis or symptoms become evident. For example, the composition may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of any one or more of the optimized clade C gp140 Env nucleic acids required to support formation of one or more of the stabilized trimers of the invention and/or one or more of the stabilized clade C trimers of the invention and, if desired, one or more immunomodulatory agents, such as in a sealed package of tablets or capsules, or in a suitable dry powder inhaler (DPI) capable of administering one or more doses.

The compositions (e.g., vaccines, vectors, stabilized trimer(s), nucleic acids, or other composition thereof described herein) of the invention can be administered in combination with one or more additional therapeutic agents, for example, for treating an HIV infection (e.g., an HIV-1 infection) in a subject. Such additional therapeutic agents can include, for example, a broadly neutralizing antibody (bnAb), e.g., those described in PCT Application No. PCT/US14/58383, WO 2012/030904, and WO 2013/055908, each of which is incorporated by reference herein in its entirety.

Exemplary bnAbs that can be administered in combination with the compositions of the invention include PGT121, PGT122, PGT123, PGT124, PGT125, PGT126, PGT127, PGT128, PGT130, PGT131, PGT132, PGT133, PGT134, PGT135, PGT136, PGT137, PGT138, PGT139, PGT141, PGT142, PGT143, PGT144, PGT145, PGT151, PGT152, PGT153, PGT154, PGT155, PGT156, PGT157, PGT158, 10-1074, a derivative or clonal relative thereof, or a combination thereof. Preferably, the N332 glycan-dependent antibody can be PGT121, or a derivative or clonal relative thereof (e.g., 10-1074). Further bnAbs that can administered in combination with the compositions of the present invention include, for example, a CD4 binding site (CD4bs)-specific antibody (e.g., 3BNC117 or VRC07-523) or a V2 glycan-dependent antibody (e.g., CAP256-VRC26).

The additional therapeutic agent can also be an antiretroviral therapy (ART), which may, e.g., be selected from any one or more of the following, or combinations thereof: efavirenz, emtricitabine, and tenofovir disoproxil fumarate (Atripla); emtricitabine, rilpivirine, and tenofovir disoproxil fumarate (Complera); elvitegravir, cobicistat, emtricitabine, and tenofovir disoproxil fumarate (Stribild); lamivudine and zidovudine (Combivir); emtricitabine, FTC (Emtriva); lamivudine, 3TC (Epivir); abacavir and lamivudine (Ebzicom); zalcitabine, dideoxycytidine, ddC (Hivid); zidovudine, azidothymidine, AZT, ZDV (Retrovir); abacavir, zidovudine, and lamivudine (Trizivir); tenofovir disoproxil fumarate and emtricitabine (Truvada); enteric coated didanosine, ddI EC (Videx EC); didanosine, dideoxyinosine, ddI (Videx); tenofovir disoproxil fumarate, TDF (Viread); stavudine, d4T (Zerit); abacavir sulfate, ABC (Ziagen); Rilpivirine (Edurant); Etravirine (Intelence); delavirdine, DLV (Rescriptor); efavirenz, EFV (Sustiva); nevirapine, NVP (Viramune or Viramune XR); amprenavir, APV (Agenerase); tipranavir, TPV (Aptivus); indinavir, IDV (Crixivan); saquinavir (Fortovase); saquinavir mesylate, SQV (Invirase); lopinavir and ritonavir, LPV/RTV (Kaletra); Fosamprenavir Calcium, FOS-APV (Lexiva); ritonavir, RTV (Norvir); Darunavir (Prezista); atazanavir sulfate, ATV (Reyataz); nelfinavir mesylate, NFV (Viracept); enfuvirtide, T-20 (Fuzeon); maraviroc (Selzentry); raltegravir, RAL (Isentress); and dolutegravir (Tivicay).

The additional therapeutic agent can also be an immunomodulator. The immunomodulator may, e.g., be selected from any one or more of the following, or combinations thereof: AS-101, Bropirimine, Acemannan, CL246,738, EL10, FP-21399, Gamma Interferon, Granulocyte Macrophage Colony Stimulating Factor, HIV Core Particle Immunostimulant, IL-2, Immune Globulin Intravenous, IMREG-1, IMREG-2, Imuthiol Diethyl Dithio Carbamate, Alpha-2 Interferon, Methionine-Enkephalin, MTP-PE Muramyl-Tripeptide, Granulocyte Colony Stimulating Factor, Remune, CD4 (e.g., recombinant soluble CD4), rCD4-IgG hybrids, SK&F106528 Soluble T4, Thymopentin, Tumor Necrosis Factor, and Infliximab.

The additional therapeutic agent can also be a reservoir activator. The reservoir activator may, e.g., be selected from any one or more of the following, or combinations thereof: histone deacytelase (HDAC) inhibitors (e.g., romidepsin, vorinostat, and panobinostat), immunologic activators (e.g., cytokines and TLR agonists), and dedicated small molecule drugs.

Dosages

The dose of a composition of the invention (e.g., a vaccine including one or more of the stabilized clade C gp140 Env trimers of the invention) or the number of treatments using a composition of the invention may be increased or decreased based on the severity of, occurrence of, or progression of, the HIV infection and/or disease related to the HIV infection (e.g., AIDS) in the subject (e.g., based on the severity of one or more symptoms of HIV infection/AIDS described above).

The stabilized clade C gp140 Env trimer compositions of the invention can be administered in a therapeutically effective amount that provides an immunogenic and/or protective effect against HIV or target protein(s) of HIV (e.g., gp160 and/or gp140). The subject may, for example, be administered a polypeptide composition of the invention (e.g., stabilized clade C gp140 Env trimers of the invention) in a non-vectored form. The polypeptide composition administered may include between approximately 1 µg and 1 mg of stabilized Env trimers, e.g., between 50 µg and 300 µg of stabilized Env trimers, e.g., 100 µg of stabilized Env trimers of the invention.

Alternatively, the subject may be administered, in the form of a viral vector, at least about $1 \times 10^3$ viral particles (vp)/dose or between $1 \times 10^1$ and $1 \times 10^{14}$ vp/dose, preferably between $1 \times 10^3$ and $1 \times 10^{12}$ vp/dose, and more preferably between $1 \times 10^5$ and $1 \times 10^{11}$ vp/dose.

Viral particles include nucleic acid molecules encoding one or more of the optimized clade C gp140 Env polypeptides of the invention and are surrounded by a protective coat (a protein-based capsid with hexon and fiber proteins). Viral particle number can be measured based on, for example, lysis of vector particles, followed by measurement of the absorbance at 260 nm (see, e.g., Steel, Curr. Opin. Biotech., 1999).

The dosage administered depends on the subject to be treated (e.g., the age, body weight, capacity of the immune system, and general health of the subject being treated), the form of administration (e.g., as a solid or liquid), the manner of administration (e.g., by injection, inhalation, dry powder propellant), and the cells targeted (e.g., epithelial cells, such as blood vessel epithelial cells, nasal epithelial cells, or pulmonary epithelial cells). The composition is preferably administered in an amount that provides a sufficient level of the stabilized clade C gp140 Env trimer gene product (e.g., a level of stabilized clade C gp140 Env trimer that elicits an immune response without undue adverse physiological effects in the subject caused by the immunogenic trimer).

In addition, single or multiple administrations of the compositions of the present invention may be given (pre- or post-infection and/or pre- or post-diagnosis) to a subject (e.g., one administration or administration two or more times). For example, subjects who are particularly susceptible to, for example, HIV infection may require multiple treatments to establish and/or maintain protection against the virus.

Levels of induced immunity provided by the pharmaceutical compositions described herein can be monitored by, for example, measuring amounts of neutralizing anti-HIV secretory and serum antibodies. The dosages may then be adjusted or repeated as necessary to trigger the desired level of immune response. For example, the immune response triggered by a single administration (prime) of a composition of the invention may not be sufficiently potent and/or persistent to provide effective protection. Accordingly, in some embodiments, repeated administration (boost), such that a prime-boost regimen is established, may significantly enhance humoral and cellular responses to the antigen of the composition.

Alternatively, as applies to recombinant therapy, the efficacy of treatment can be determined by monitoring the level of the one or more optimized clade C gp140 Env trimers expressed by or present in a subject (e.g., a human) following administration of the compositions of the invention. For example, the blood or lymph of a subject can be tested for the immunogenic trimer(s) using, for example, standard assays known in the art (see, e.g., Human Interferon-Alpha Multi-Species ELISA kit (Product No. 41105) and the Human Interferon-Alpha Serum Sample kit (Product No. 41110) from Pestka Biomedical Laboratories (PBL), Piscataway, N.J.).

A single dose of one or more of the compositions of the invention may achieve protection, pre-infection or pre-diagnosis. In addition, a single dose administered post-infection or post-diagnosis can function as a treatment according to the present invention.

A single dose of one or more of the compositions of the invention can also be used to achieve therapy in subjects being treated for a disease. Multiple doses (e.g., 2, 3, 4, 5, or more doses) can also be administered, in necessary, to these subjects.

Carriers, Excipients, Diluents

Therapeutic formulations of the compositions of the invention (e.g., vaccines, vectors, stabilized trimer(s), nucleic acid molecules, etc.) may be prepared using standard methods known in the art by mixing the active ingredient having the desired degree of purity with optional physiologically acceptable carriers, excipients, or stabilizers (Remington's Pharmaceutical Sciences ($20^{th}$ edition), ed. A. Gennaro, 2000, Lippincott, Williams & Wilkins, Philadelphia, Pa.). Acceptable carriers include saline or buffers, such as phosphate, citrate, and other organic acids; antioxidants, including ascorbic acid; low molecular weight (less than about 10 residues) polypeptides; proteins, such as serum albumin, gelatin or immunoglobulins; hydrophilic polymers, such as polyvinylpyrrolidone, amino acids, such as glycine, glutamine, asparagines, arginine, or lysine; monosaccharides, disaccharides, and other carbohydrates including, e.g., glucose, mannose, or dextrins; chelating agents, such as EDTA; sugar alcohols, such as mannitol or sorbitol; salt-forming counterions, such as sodium; and/or nonionic surfactants, such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of about 0.005 to about 0.02%.

Adjuvants

Any one of the compositions of the invention (e.g., vaccines, vectors, stabilized trimer(s), nucleic acid molecules, etc.) can be formulated to include, be administered concurrently with, and/or be administered in series with, one or more pharmaceutically acceptable adjuvants to increase the immunogenicity of the composition (e.g., upon administration to a subject in need thereof, e.g., a subject infected with HIV or at risk of an HIV infection). Adjuvants approved for human use include aluminum salts (alum). These adjuvants have been useful for some vaccines including, e.g., hepatitis B, diphtheria, polio, rabies, and influenza. Other useful adjuvants include Complete Freund's Adjuvant (CFA), Incomplete Freund's Adjuvant (IFA), muramyl dipeptide (MDP), synthetic analogues of MDP, N-acetylmuramyl-L-alanyl-D-isoglutamyl-L-alanine-2-[1,2-dipalmitoyl-s-gly-cero-3-(hydroxyphosphoryloxy)]ethylamide (MTP-PE) and compositions containing a metabolizable oil and an emulsifying agent, wherein the oil and emulsifying agent are present in the form of an oil-in-water emulsion having oil droplets substantially all of which are less than one micron in diameter.

Ex Vivo Transfection and Transduction

The present invention also provides for the ex vivo transfection or transduction of cells, tissue, or organs, followed by administration of these cells, tissues, or organs into a subject (e.g., human) to allow for the expression of one or more of the optimized clade C gp140 Env polypeptides of the invention that have immunogenic properties. In one embodiment, the cells, tissue(s), or organ(s) are autologous to the treated subject. Cells can be transfected or transduced ex vivo with, for example, one or more vectors of the invention to allow for the temporal or permanent expression of one or more of the optimized clade C gp140 Env polypeptides in the treated subject. Upon administering these modified cells to the subject, the one or more vectors of the invention will be expressed, eliciting protective or therapeutic immune responses (e.g., cellular or humoral immune responses, e.g., production of neutralizing anti-HIV antisera) directed against the clade C gp140 immunogenic trimer or trimers that form.

Cells that can be isolated and transfected or transduced ex vivo according to the methods of invention include, but are not limited to, blood cells, skin cells, fibroblasts, endothelial cells, skeletal muscle cells, hepatocytes, prostate epithelial cells, and vascular endothelial cells. Stem cells are also appropriate cells for transduction or transfection with a vector of the invention. Totipotent, pluripotent, multipotent, or unipotent stem cells, including bone marrow progenitor cells, hematopoietic stem cells (HSC), and mesenchymal stem cells (MSCs) (e.g., bone marrow (BM) or umbilical cord MSCs) can be isolated and transfected or transduced with, for example, a vector of the invention, and administered to a subject according to the methods of the invention.

The method of transfection or transduction has a strong influence on the strength and longevity of protein expression (e.g., stabilized clade C gp140 trimer expression) in the transfected or transduced cell, and subsequently, in the subject (e.g., human) receiving the cell. The present invention provides vectors that are temporal (e.g., adenoviral vectors) or long-lived (e.g., retroviral vectors) in nature. Regulatory sequences (e.g., promoters and enhancers) are known in the art that can be used to regulate protein expression. The type of cell being transfected or transduced also has a strong bearing on the strength and longevity of protein expression. For example, cell types with high rates of turnover can be expected to have shorter periods of protein expression.

Kits

The invention also provides kits that include a pharmaceutical composition containing a vaccine, vector, stabilized trimer, or optimized viral polypeptide of the invention, and a pharmaceutically-acceptable carrier, in a therapeutically effective amount for preventing or treating a viral infection (e.g., HIV infection). The kits include instructions to allow a clinician (e.g., a physician or nurse) to administer the composition contained therein.

Preferably, the kits include multiple packages of the single-dose pharmaceutical composition(s) containing an effective amount of a vaccine, vector, stabilized trimer, or optimized viral polypeptide of the invention. Optionally, instruments or devices necessary for administering the pharmaceutical composition(s) may be included in the kits. For instance, a kit of this invention may provide one or more pre-filled syringes containing an effective amount of a vaccine, vector, stabilized trimer, or optimized viral polypeptide of the invention. Furthermore, the kits may also include additional components such as instructions or administration schedules for a patient infected with or at risk of being infected with a virus to use the pharmaceutical composition(s) containing a vaccine, vector, stabilized trimer, or optimized viral polypeptide of the invention.

It will be apparent to those skilled in the art that various modifications and variations can be made in the compositions, methods, and kits of the present invention without departing from the spirit or scope of the invention. Thus, it is intended that the present invention cover the modifications and variations of this invention provided they come within the scope of the appended claims and their equivalents.

EXAMPLES

The present invention is illustrated by the following examples, which are in no way intended to be limiting of the invention.

Example 1. Materials and Methods

Plasmids, Cell Lines, Protein Production, and Antibodies

Soluble forms of HIV-1 envelope gp160 were generated by removing the transmembrane and C-terminal regions of gp160 sequences to result in a soluble form of HIV-1 envelope (gp140). The wild type, full-length gp160 envelope sequences for 405C, 459C, and 939C were cloned from acutely infected patients enrolled in the South African HVTN503 (the Phambili) study and were generously provided by Dr. Leonidas Stamatatos (Seattle BioMed) (Gray et al., 2011) (Table 2).

Codon-optimized synthetic genes for the 405C, 459C, 939C, and C97ZA012.1 gp140 trimers were produced by GeneArt (Life Technologies) under our direction. All constructs were optimized to contain a consensus leader signal sequence peptide, as well as a C-terminal foldon trimerization tag followed by a His-tag as described previously (Frey et al., 2008; Nkolola et al., 2010). The codon-optimized synthetic genes for the full-length 405C, 459C, and 939C gp120s were cloned from their respective gp140 construct and a C-terminal His-tag was added.

C97ZA012.1 trimers were generated in 293T cell lines stably transfected with the trimeric construct (Codex Biosolutions). All other trimeric and monomeric constructs were generated in 293T cells utilizing transient transfections with polyethylenimine. Cell lines were grown in DMEM with 10% FBS to confluence and then changed to Freestyle 293 expression medium for protein purification (Invitrogen). Cell supernatants were harvested 5 days after medium change, centrifuged for clarification, and brought to a final concentration of 10 mM imidazole.

All His-tagged proteins were purified by Ni-NTA column (GE Healthcare). Ni-NTA columns were washed with 20-mM imidazole and protein was eluted with 300-mM imidazole. Fractions containing protein were pooled and concentrated. Protein constructs were further purified utilizing gel-filtration chromatography on Superose 6 (GE Healthcare) for gp140 trimeric constructs and Superdex 200 (GE Healthcare) for gp120 monomeric constructs in running buffer containing 25 mM Tris (pH 7.5) and 150-mM NaCl. Purified proteins were concentrated, frozen in liquid nitrogen, and stored at −80° C.

Soluble two-domain CD4 was produced as described previously (Freeman et al., 2010). 17b hybridoma was provided by James Robinson (Tulane University, New Orleans, La.) and purified as described previously (Kovacs et al., 2012). VRC01 was obtained through the NIH AIDS Reagent Program, Division of AIDS, NIAID, NIH: HIV-1 gp120 MAb (VRC01), from John Mascola (Wu et al., 2010). 3BNC117 was kindly provided by Michel Nussenzweig (Rockefeller University, New York, N.Y.). PGT121 and PGT126 were generously provided by Dennis Burton (The Scripps Research Institute, La Jolla, Calif.). 2F5, 4E10, PG9, PG16 were purchased from Polymun Scientific.

TABLE 2

Information on HIV-1 Envelope Sequences Utilized for Immunogen Generation

| Sequence Name | Gen Bank Accession Number | Country of Origin | Clade | Patient Disease Status | Year | Reference(s) |
| --- | --- | --- | --- | --- | --- | --- |
| C97ZA012.1 (C97) | AF286227 | South Africa | C | Chronic | 1997 | Rodenburg et al., 2001 (sequence) Frey et al., 2008 (production) Nkolola et al., 2010 (production and immunogenicity) Kovacs et al., 2012 (antigenicity and immunogenicity) |
| 405C | KC769517 | South Africa | C | Early/Acute | 2008 | Gray et al., 2011 (isolation) |
| 459C | KC769514 | South Africa | C | Early/Acute | 2008 | Gray et al., 2011 (isolation) |
| 939C | N/A | South Africa | C | Early/Acute | 2008 | Gray et al., 2011 (isolation) |

Assessment of Protein Stability

To assess protein stability after freeze/thaw, 105 µg of each protein was thawed at room temperature, 5 µg of protein was run on a denatured, reduced 4-15% SDS-PAGE gel (Bio-Rad). To assess protein stability at 4° C., an identical protocol was conducted as described above, except that thawed samples were incubated at 4° C. for two weeks.

Western Blot and ELISA Detection of gp41 Epitopes

For western blot analysis, 30 ng of each protein was heated to 100° C. in reducing buffer (Pierce) for five minutes. Samples were cooled on ice and then run on denatured, reduced 4-15% SDS-PAGE gel (Bio-Rad). Proteins were then transferred to a PVDF membrane with an iBlot (Invitrogen) using conditions recommended by the manufacturers. Membranes were blocked overnight in 3% BSA (Sigma), 0.5% Tween 20 (Sigma), in 1×PBS at 4° C. Either 2F5 IgG or 4E10 IgG (Polymun Scientific) were utilized as primary antibodies at 1:10,000 dilutions, and peroxidase-conjugated AffiniPure Goat Anti-Human IgG (Jackson ImmunoResearch) was utilized as a secondary antibody at a 1:5,000 dilution. Western blots were developed with Amersham ECL Plus Western Blotting Detection System Kit (GE Healthcare) according to manufacturers recommendations.

For analysis by ELISA binding, 96-well Maxisorp ELISA plates (Thermo Scientific) were coated and incubated overnight at 4° C. with either 2F5 or 4E10 IgG (Polymun Scientific) at 1 µg/ml in PBS. Purified proteins were added to a final concentration of 10 µg/ml and threefold serially dilutions of all samples were conducted. An anti-6×His tag antibody conjugated to HRP at a dilution of 1:5000 was utilized for detection (Abcam). Plates were developed with SureBlue tetramethylbenzidine (TMB) microwell peroxidase (KPL Research Products) for 2.5 minutes and the reaction was quenched with TMB stop solution. Plates were read at 450 nm with a 550 nm background subtraction using the Spectramax Plus ELISA plate reader (Molecular Devices) and Softmax Pro-4.7.1 software. C97ZA012.1 gp140 was utilized as a negative control, as it had previously been shown to not present these gp41 epitopes (Kovacs et al., 2012) and 92UG-gp41-inter (92UGinter) was utilized as a positive control, as it had previously been shown to present both of these epitopes (Frey et al., 2008).

Surface Plasmon Resonance Binding Analysis

SPR experiments were conducted on a Biacore 3000 (GE Healthcare) at 25° C. utilizing HBS-EP (10 mM Hepes (pH 7.4), 150 mM NaCl, 3 mM EDTA, 0.005% P20) (GE Healthcare) as the running buffer. Immobilization of CD4 (1,500 RU) or protein A (ThermoScientific) to CM5 chips was performed following the standard amine coupling procedure as recommended by the manufacturer (GE Healthcare). Immobilized IgGs were captured at 300-750 RU. For PG9 and PG16 binding to 405C, 459C, and 939C trimers and monomers, 3,500 and 4,500 RU of antibody was used for PG9 and PG16, respectively. Binding experiments were conducted with a flow rate of 50 µl/min with a 2-minute associate phase and a 5-minute dissociation phase. Regeneration was conducted with one injection (3 seconds) of 35 mM NaOH and 1.3 M NaCl at 100 µl/min followed by a 3-minute equilibration phase in HBS-EP. Identical injections over blank surfaces were subtracted from the binding data for analysis. Binding kinetics were determined using BIAevaluation software (GE Healthcare) and the Langmuir 1:1 binding model. Binding kinetics for PG16 with the mosaic trimer and monomer were determined using the bivalent analyte model. All samples were run in duplicate and yielded similar kinetic results. Single curves of the duplicates are shown in all figures.

Guinea Pig Vaccinations

Outbred female Hartley guinea pigs (Elm Hill) were used for all vaccination studies. Guinea pigs were immunized with protein trimers intramuscularly in the quadriceps bilaterally at 4-week intervals for a total of 3 injections with five guinea pigs per group. Vaccine formulations for each guinea pig consisted of a total of 100 µg of trimer per injection formulated in 15% Emulsigen (vol/vol) oil-in-water emulsion (MVP Laboratories) and 50 µg CpG (Midland Reagent Company) as adjuvants. In multivalent vaccination regimens, the total amount of injected protein is maintained and divided equally among the total number of trimers present in the formulation. Multivalent mixtures included C97ZA012.1, 405C, 459C, and 939C trimers (QuadC Mixture). Additionally, the vaccination number, timing and adjuvant formulation were maintained as in the monovalent vaccinations. Serum samples were obtained from the vena cava of anesthetized animals 4 weeks after each immunization.

For heterologous prime-boost vaccination regimens, guinea pigs were immunized with protein trimers intramuscularly in the quadriceps bilaterally at 4-week intervals for a total of 4 injections with five guinea pigs per group. Adjuvants added as described above. Regimens include one group that received 4 injections of C97ZA012.1 trimer (C97 only prime-boost) and one group that was primed with C97ZA012.1 trimer followed by boosts with 459C, 405C, and 939C trimers, respectively (QuadC prime-boost). Serum samples were obtained from the vena cava of anesthetized animals 4 weeks after each immunization.

Endpoint ELISAs

Serum binding antibodies against gp140 were measured by endpoint enzyme-linked immunosorbant assays (ELISAs). 96-well Maxisorp ELISA plates (Thermo Scientific) were coated and incubated overnight at 4° C. with 100 µl/well of 1 µg/ml gp140 protein in PBS. Plates were then washed with PBS containing 0.05% Tween 20 (wash buffer) and blocked for 2.5 hours with Blocker™ casein in PBS (Thermo Scientific) with this and all subsequent incubations conducted at room temperature. Guinea pig sera were then added in serial dilutions and incubated for 1 hour. Plates were then washed three times with wash buffer and incubated for 1 hour with a 1/2000 dilution of an HRP-conjugated goat anti-guinea pig secondary antibody (Jackson ImmunoResearch Laboratories). Plates were washed three times with wash buffer and then developed with SureBlue tetramethylbenzidine (TMB) microwell peroxidase (KPL Research Products) for 2.5 minutes and the reaction was quenched with TMB stop solution. Plates were read at 450 nm with a 550 nm background subtraction using the Spectramax Plus ELISA plate reader (Molecular Devices) and Softmax Pro-4.7.1 software. End-point titers were considered positive at the highest dilution that maintained an absorbance >2-fold above background values.

TZM.bl Neutralization Assay

All TZM.bl neutralization assays were conducted in the Seaman Laboratory (BIDMC, Boston, Mass.) under Good Clinical Laboratory Practice (GCLP) conditions. Functional neutralizing antibody responses against HIV-1 Env pseudovirions were measured using a luciferase-based virus neutralization assay in TZM.bl cells as described previously (Montefiori et al., 2005). The assay measures the reduction in a luciferase reporter signal in TZM.bl cells follow a single round of HIV-1 pseudovirion infection. The xTZM.bl cells utilized contain luciferase under a tat-inducible promoter. The $ID_{50}$ was calculated as the serum dilution that resulted in a 50% reduction in relative luminescence units compared to virus-only control wells after the subtraction of cell control relative luminescence units. Briefly, threefold serial dilutions of serum samples were preformed in duplicate (96-well flat-bottomed plate) in 10% DMEM growth medium (100 µl per well). Pseudovirions were added to each well in a volume of 50 µl, and the plates were incubated for 1 hour at 37° C. TZM.bl cells were then added ($1\times10^4$ per well in 100 µl of volume) in 10% DMEM growth medium containing diethylaminoethyldextrane (Sigma) at a final concentration of 11 µg/ml. Murine leukemia virus (MuLV) was included as a negative control in all assays. HIV-1 Env pseudovirions, including tier 1 isolates from clade A (DJ263.8, Q23.17, MS208.A1), clade B (SF162.LS, BaL.26, SS1196.1, 6535.3), and clade C (MW965.26, TV1.21, ZM109F.PB4, ZM197M.PB7), and were prepared as described previously (Montefiori et al., 2005).

Example 2. Generation of Novel, Acute Clade C Immunogens 15 acute clade C envelope sequences were obtained from the HVTN503 study and were optimized as described in the Example 1 above. These sequences were screened for expression levels in 293T cells. C97ZA012 gp140 was utilized as a positive control for expression, as this protein is known to express at high levels in large-scale purifications. Supernatant from transfected cells was harvested and assessed for protein expression by western blot utilizing an anti-penta-histidine HRP antibody (FIG. 1), and these expression data were verified by two separate quantitative binding ELISAs. Western blot results show that eight of the fifteen proteins expressed at a level similar to or greater than that of the C97ZA012 gp140 protein (including 405C, 459C, 939C, 823cD6, 756C, 823C, 349C and 706C), while the remaining sequences (including 426C, 590C, 072C, 327C, 431C, 885C, and 140C) appeared to have expression levels lower than that of the control. Based on initial expression results, the eight sequences with the highest expression levels were screened for expression in a large-scale purification assay.

Figures 2A, 2B:
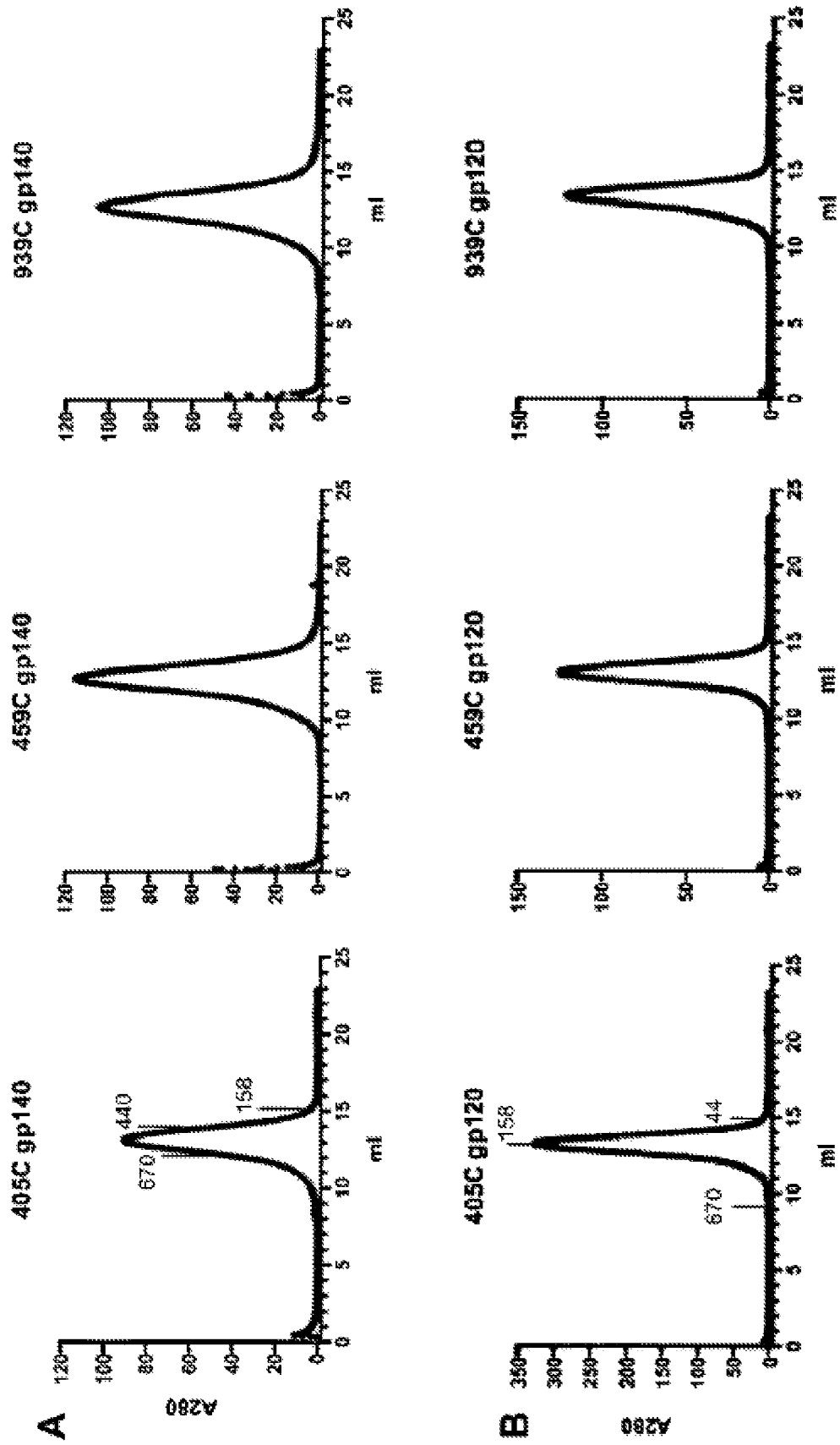
FIG. 2A is a gel filtration chromatography trace of 405C (left), 459C (center), 939C (right) gp140 trimers as run on a Superose 6 column.
FIG. 2B is a gel filtration chromatography trace of 405C (left), 459C (center), 939C (right) gp140 monomers as run on a Superdex 200 column.
Figures 2C, 2D:
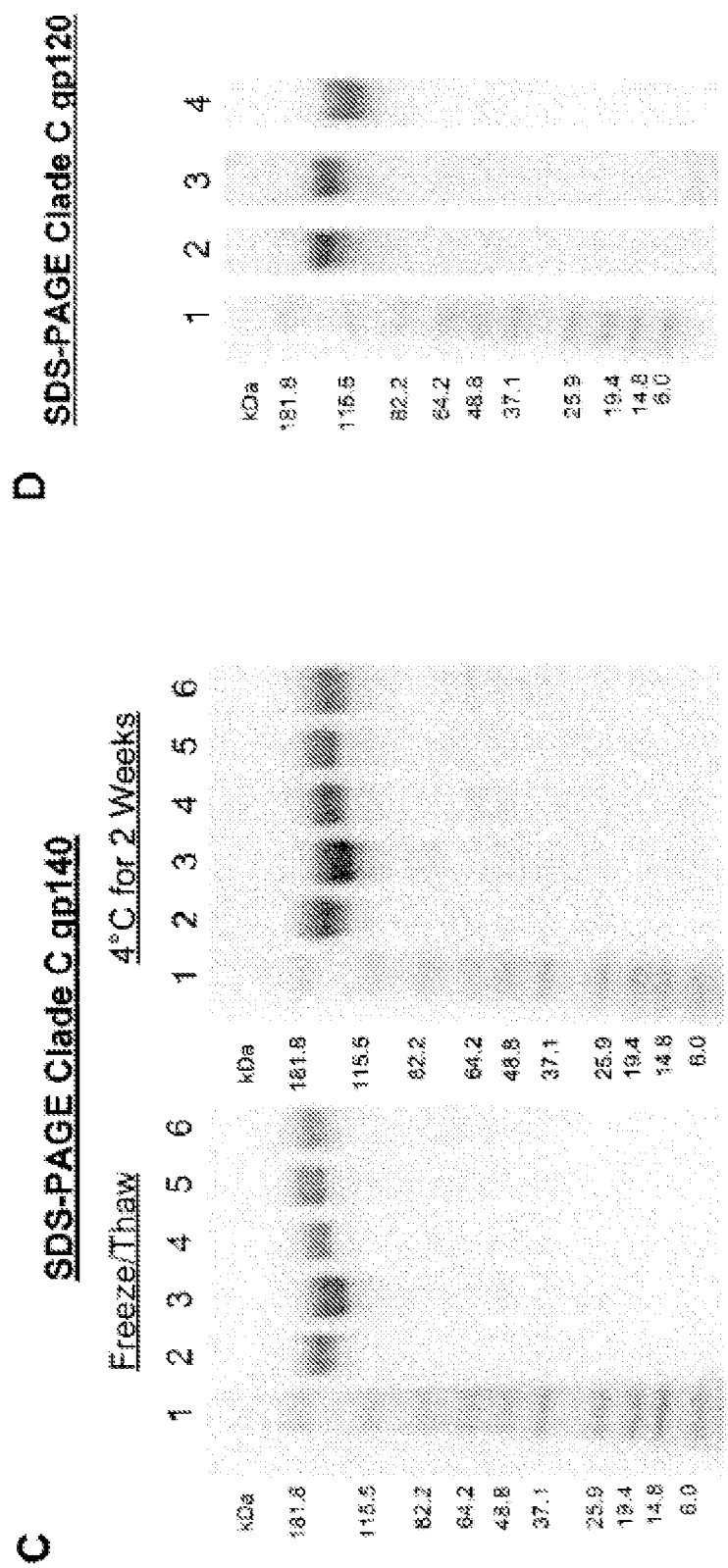
FIG. 2C is a Coomassie-stained SDS-PAGE gel of pooled peaks of trimers after freeze/thaw (left) or incubation at 4° C. (right) for two weeks. Trimers are as follows for both gels: (1) C97ZA012, (2) 1086C, (3) 405C, (4) 459C, (5) 939C gp140.
FIG. 2D is a Coomassie-stained SDS-PAGE gel of pooled peaks of monomers. Monomers are as follows: (1) 405C, (2) 459C, and (3) 939C gp120.

All eight of the highest expressing constructs formed trimeric populations as assessed by gel filtration chromatography, but varied in expression levels from 0.25 to 1.4 milligrams protein per liter of supernatant. The three highest expressing constructs, 405C, 459C, and 939C were chosen for further biochemical and immunological analyses. These three trimers have an average yield of 1.3 mg, 1.4 mg, and 1.0 mg protein per liter of supernatant from transient transfections, respectively. Each of these high expressing trimers represents a homogenous population as measured by gel filtration chromatography (FIG. 2A). Additionally, these trimers are relatively stable populations, as negligible degradation is seen both after freeze/thaw and after incubation at 4° C. for two weeks as compared to C97ZA012 and 1086C trimers, which are known to be stable (FIG. 2C). In addition to the generation of acute clade C trimers, sequence-matched monomers were produced to have as tools for further studies. The monomeric constructs of 405C, 459C, and 939C also represent homogenous populations (FIGS. 2B and 2D) with average yields of 3.4 mg, 2.5 mg, and 0.72 mg per liter of supernatant, respectively.

Example 3. Phylogenetic Characterization of Novel, Acute Clade C Immunogens

Phylogenetic characterization of our four clade C gp140 isolates (C97ZA012, 405C, 459C, and 939) was conducted.

Figures 3A, 3B:
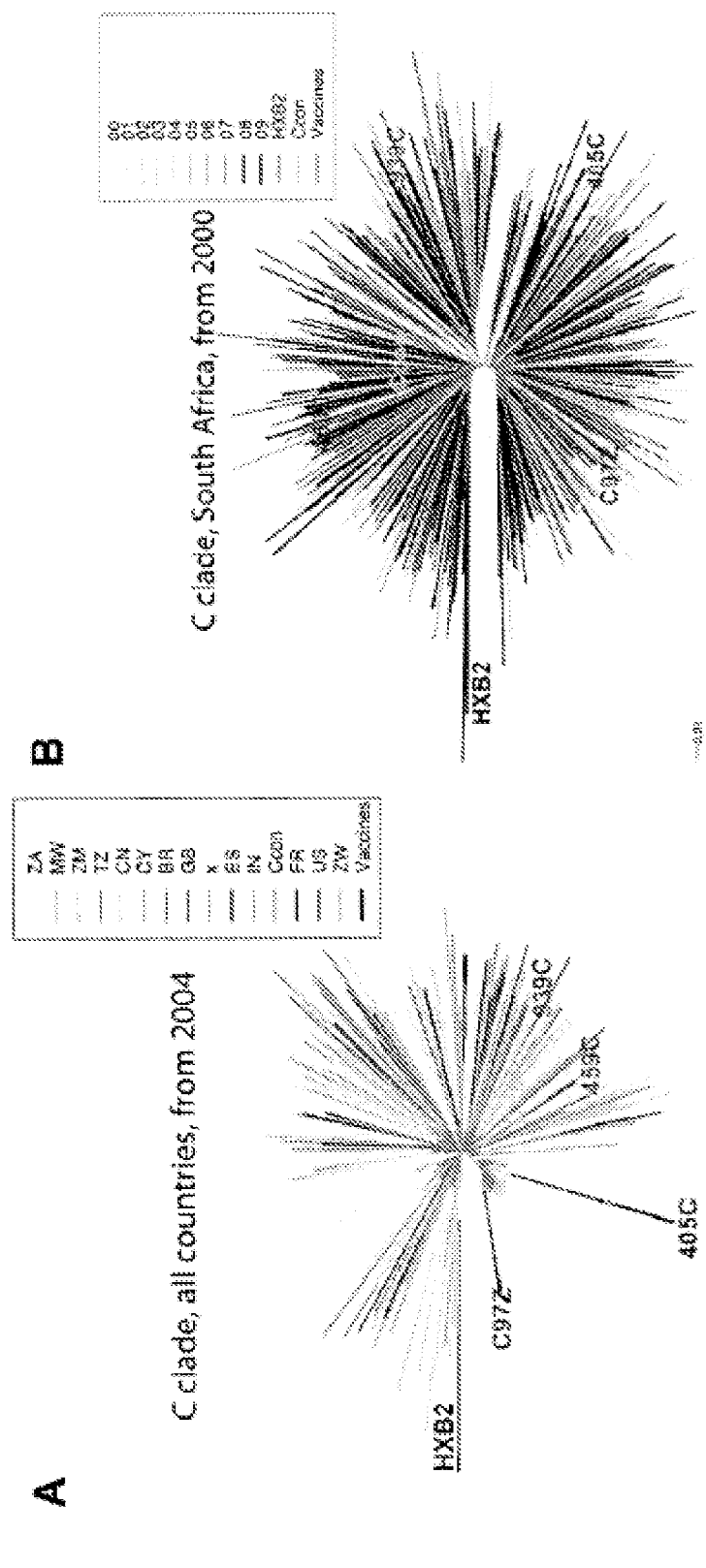
FIG. 3A is a phylogenetic tree comparing each of the four clade C vaccine envelope (Env) sequences (C97, 405C, 459C, and 939C) to 489 clade C sequences sampled starting from the year 2004. Country of origin for each sequence colored according to the key provided containing two letter abbreviations for each country. Vaccine Env strains are highlighted in red, consensus clade C Env sequence in cyan, HXB2 (outgroup) in dark blue.
FIG. 3B is a phylogenetic tree comparing each of the four clade C vaccine Env sequences (C97, 405C, 459C, and 939C) to 506 clade C sequences from South Africa starting from the year 2000. Year of origin colored according to the key provided. Vaccine Env strains are highlighted in red, consensus clade C Env sequence in cyan, HXB2 (outgroup) in dark blue.

Two different maximum likelihood trees were generated: one tree compared the four gp140 sequences to all clade C sequences, from any country, in 2004 (FIG. 3A), and one tree compared the sequences to all clade C sequences from South Africa only from the years 2000 to 2009 (FIG. 3B). These analyses determined that 459C is the most central of the four sequences, while 405C is a sequence outlier. It was also found that 459C and 939C clustered with sequences from a greater number of countries than 405C and C97ZA012. These data suggest that a 459C-based immunogen may allow for the generation of more cross-reactive antibodies than the other three sequences. Sequence analysis was also conducted for each of the trimers to known consensus sequence epitopes for broadly neutralizing antibodies. These analyses revealed that the 939C trimer lacks the N332 glycan, and thus lacks the epitope for PGT-like antibodies. Additionally, C97ZA012 and 405C were found to be closer to the consensus sequence for the PG9 epitope than 459C and 939C. Finally, it was observed that 459C and 939C were closer to the consensus sequence for CD4 binding site antibodies (b12, VRC01) than C97ZA012 or 405C based on protein sequence. These data provide important information about the sequence diversity of these four immunogens and have important implications for choosing which proteins to use in vaccination studies.

Example 4. Neutralization Sensitivity of Acute Clade C Immunogens

Simian/human immunodeficiency viruses (SHIVs) containing the full-length gp160 sequence for 405C (SEQ ID NO: 5) and 459C (SEQ ID NO: 4) were generated. A SHIV containing the full-length gp160 sequence for 939C (SEQ ID NO: 6) has not yet been generated due to difficulties with cloning. These SHIVs were assessed for neutralization sensitivity utilizing the TZM.bl neutralization assay. Overall, these envelope sequences were relatively neutralization resistant (Table 3 below). 405C and 459C had comparable, modest neutralization sensitivities to CD4 binding site antibodies VRCO1 and 3BNC117, while being resistant to soluble CD4 binding and b12 neutralization. These isolates possessed different neutralization phenotypes when considering V1/V2/glycan binding antibodies PG9 and PG16, in that only 405C was sensitive to neutralization by PG9, while PG16 neutralized both isolates in a comparable manner. 459C was found to be more sensitive to PGT128 than 405C, which binds both V3 and glycans in the region. Both isolates were resistant to neutralization by glycan-binding antibody, 2G12, and membrane proximal external region (MPER)-binding antibody, 2F5, which is characteristic of clade C envelope sequences (Li et al., 2006). Finally, 405C exhibited modest neutralization sensitivity to the MPER-binding antibody, 4E10, while 459C was resistant to neutralization by this antibody. These data suggest that these two acute clade C sequences are relatively neutralization resistant and possess unique neutralization profiles.

TABLE 3

IC50 Titers (TZM.bl cells, ug/ml) for Acute Clade C SHIVs

| | 405C SHIV | 459C SHIV |
|---|---|---|
| 4E10 IgG | 18.25 | >50 |
| 2F5 IgG | >50 | >50 |
| 2G12 IgG | >50 | >50 |
| PG9 IgG | 17.41 | >50 |
| PG16 IgG | 2.05 | 6.7 |

TABLE 3-continued

IC50 Titers (TZM.bl cells, ug/ml) for Acute Clade C SHIVs

|  | 405C SHIV | 459C SHIV |
|---|---|---|
| PGT128 IgG | 45.94 | 0.65 |
| sCD4 | >50 | 48.66 |
| 3BNC117 IgG | 4.94 | 5.97 |
| VRC01 IgG | 13.31 | 11.95 |
| b12 IgG | >50 | >50 |

Example 5. Antigenic Properties of Novel, Acute Clade C Immunogens

To ensure that the novel, clade C trimeric immunogens maintained the antigenic properties characteristic of HIV-1 envelope proteins, biochemical analyses were conducted. First we tested the ability of each of the three trimers, as well as their sequence-matched monomers, to bind soluble CD4 by surface plasmon resonance (SPR). As the CD4 binding site is necessary for viral entry, it should be presented in all properly folded envelope proteins. All of the clade C trimers and monomers presented the CD4 binding site and bound to CD4 with relatively high affinities (FIG. 4A; Table 4 below). It is of interest, however, that the 405C monomer appeared to bind to CD4 at a reduced magnitude when compared to the 459C and 939C monomers. Similarities in affinity for CD4 binding to trimer and monomer are likely due to avidity effects as 1,500 RU of CD4 were utilized for capture, resulting in a higher relative affinity for the trimer compared to the monomer. These data illustrate that all of the immunogens possess the CD4 binding site and are likely folded in the correct manner.

Figures 4A, 4B:
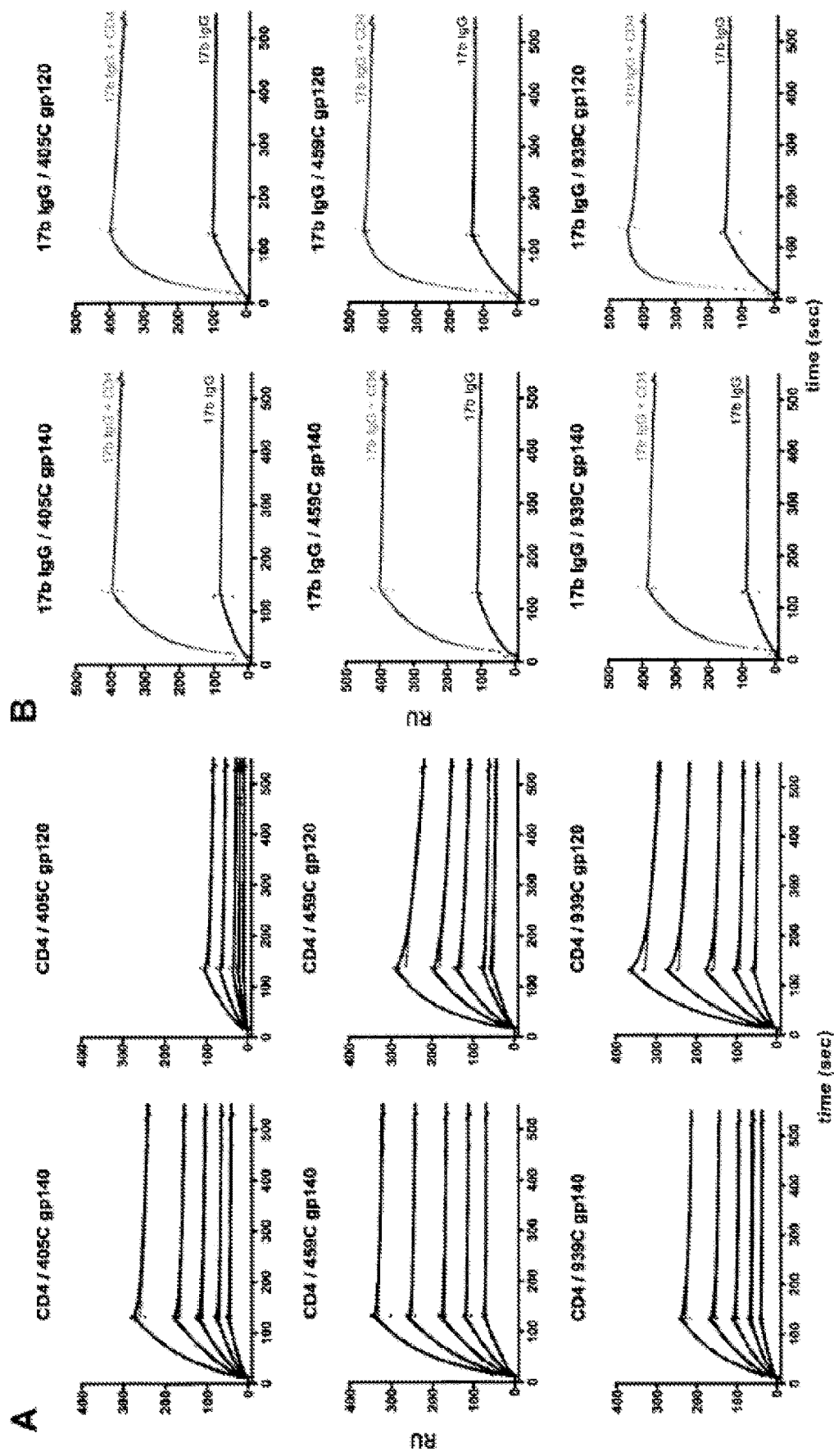
FIG. 4A are surface plasmon resonance (SPR) sensorgrams showing that optimized 405C (top), 459C (middle), and 939C (bottom) gp140 trimers (left) and gp120 monomers (right) bound to CD4. Soluble two-domain CD4 was irreversibly coupled to a CM5 chip, and 405C, 459C, or 939C gp140 or gp120 was flowed over the chip at concentrations of 62.5-1000 nM. Sensorgrams presented in black. Kinetic fits in green. RU, response units.
FIG. 4B are SPR sensorgrams showing that optimized 405C (top), 459C (middle), and 939C (bottom) gp140 trimers (left) and gp120 monomers (right) bound to 17b at a higher magnitude when the bound to CD4. Protein A was irreversibly coupled to a CM5 chip and 17b IgG was captured. 405C, 459C, or 939C gp140 or gp120 was flowed over the bound IgG at a concentration of 1000 nM in the presence or absence of CD4 bound to the immunogen. 17b binding alone in red. CD4 coupled to trimer or monomer binding to 17b IgG in blue. RU, response units.

In addition to CD4 binding, we assessed the intrinsic structural flexibility of the immunogens by measuring 17b binding to the co-receptor binding site. While all three trimers show a modest magnitude of 17b binding in the absence of bound CD4, there is a four-fold increase in the magnitude of binding to 17b when the trimer is bound to CD4 (FIG. 4B). This suggests that while a portion of the trimer population is flexible and presenting the 17b epitope, the majority of the trimer population is held in a structurally rigid state. The sequence-matched monomeric proteins present a similar phenotype, in that they bind to 17b at a higher magnitude when bound to CD4 than in the CD4 unbound state. All of the acute clade C proteins bind to 17b at an increased magnitude when bound to CD4, suggesting that these proteins are capable of undergoing the structural transition necessary to form and stabilize the bridging sheet upon CD4 binding.

TABLE 4

Binding Rate Constants Obtained from Surface Plasmon Resonance (SPR) Analysis

| Immobilized ligand | Flowing analyte | Ka (1/Ms) | Kd (1/s) | Kd (M) |
|---|---|---|---|---|
| CD4 | 405C gp140 | $1.54 \times 10^4$ | $1.96 \times 10^{-4}$ | $1.23 \times 10^{-8}$ |
|  | 405C gp120 | $5.56 \times 10^3$ | $3.27 \times 10^{-4}$ | $9.80 \times 10^{-6}$ |
|  | 459C gp140 | $2.37 \times 10^4$ | $9.89 \times 10^{-6}$ | $4.17 \times 10^{-9}$ |
|  | 459C gp120 | $1.82 \times 10^4$ | $4.90 \times 10^{-4}$ | $2.69 \times 10^{-8}$ |
|  | 939C gp140 | $1.65 \times 10^4$ | $2.06 \times 10^{-4}$ | $1.25 \times 10^{-8}$ |
|  | 939C gp120 | $1.95 \times 10^4$ | $3.10 \times 10^{-4}$ | $1.59 \times 10^{-8}$ |
| VRC01 IgG | 405C gp140 | $6.09 \times 10^3$ | $4.52 \times 10^{-5}$ | $7.42 \times 10^{-3}$ |
|  | 405C gp120 | $7.87 \times 10^3$ | $2.78 \times 10^{-4}$ | $3.53 \times 10^{-8}$ |
|  | 459C gp140 | $6.99 \times 10^3$ | $4.75 \times 10^{-5}$ | $7.50 \times 10^{-9}$ |
|  | 459C gp120 | $3.32 \times 10^3$ | $1.09 \times 10^{-3}$ | $3.28 \times 10^{-7}$ |

TABLE 4-continued

Binding Rate Constants Obtained from Surface Plasmon Resonance (SPR) Analysis

| Immobilized ligand | Flowing analyte | Ka (1/Ms) | Kd (1/s) | Kd (M) |
|---|---|---|---|---|
|  | 939C gp140 | $4.40 \times 10^3$ | $1.55 \times 10^{-5}$ | $3.52 \times 10^{-9}$ |
|  | 939C gp120 | $4.35 \times 10^3$ | $2.49 \times 10^{-4}$ | $5.73 \times 10^{-8}$ |
| 3BNC117 IgG | 405C gp140 | $4.11 \times 10^3$ | $3.22 \times 10^{-4}$ | $7.83 \times 10^{-8}$ |
|  | 405C gp120 | $4.90 \times 10^3$ | $4.20 \times 10^{-4}$ | $8.58 \times 10^{-8}$ |
|  | 459C gp140 | $8.50 \times 10^3$ | $1.04 \times 10^{-5}$ | $1.24 \times 10^{-9}$ |
|  | 459C gp120 | $6.13 \times 10^3$ | $5.00 \times 10^{-5}$ | $9.51 \times 10^{-9}$ |
|  | 939C gp140 | $8.33 \times 10^3$ | $2.24 \times 10^{-4}$ | $2.71 \times 10^{-8}$ |
|  | 939C gp120 | $6.45 \times 10^3$ | $9.61 \times 10^{-4}$ | $1.72 \times 10^{-7}$ |
| PGT121 IgG | 405C gp140 | $9.78 \times 10^3$ | $1.04 \times 10^{-4}$ | $1.06 \times 10^{-8}$ |
|  | 405C gp120 | $7.67 \times 10^3$ | $4.92 \times 10^{-4}$ | $6.42 \times 10^{-8}$ |
|  | 459C gp140 | $1.57 \times 10^4$ | $8.73 \times 10^{-5}$ | $5.56 \times 10^{-9}$ |
|  | 459C gp120 | $6.72 \times 10^3$ | $8.24 \times 10^{-4}$ | $1.23 \times 10^{-7}$ |
|  | 939C gp140 | $1.67 \times 10^4$ | $4.30 \times 10^{-4}$ | $2.57 \times 10^{-8}$ |
|  | 939C gp120 | Nb | Nb | Nb |
| PGT126 IgG | 405C gp140 | $2.87 \times 10^4$ | $2.82 \times 10^{-4}$ | $5.35 \times 10^{-8}$ |
|  | 405C gp120 | $3.14 \times 10^4$ | $1.20 \times 10^{-3}$ | $3.83 \times 10^{-8}$ |
|  | 459C gp140 | $2.95 \times 10^4$ | $2.43 \times 10^{-4}$ | $8.30 \times 10^{-9}$ |
|  | 459C gp120 | $1.48 \times 10^4$ | $5.92 \times 10^{-4}$ | $4.13 \times 10^{-8}$ |
|  | 939C gp140 | $3.50 \times 10^4$ | $2.32 \times 10^{-4}$ | $6.63 \times 10^{-3}$ |
|  | 939C gp120 | Nb | Nb | Nb |
| PG9 IgG | 405C gp140 | $1.97 \times 10^3$ | $6.62 \times 10^{-4}$ | $3.35 \times 10^{-7}$ |
|  | 405C gp120 | Nb | Nb | Nb |
|  | 459C gp140 | $7.15 \times 10^3$ | $3.20 \times 10^{-3}$ | $4.48 \times 10^{-7}$ |
|  | 459C gp120 | Nb | Nb | Nb |
|  | 939C gp140 | $8.01 \times 10^3$ | $1.26 \times 10^{-3}$ | $1.57 \times 10^{-7}$ |
|  | 939C gp120 | Nb | Nb | Nb |
| PG16 IgG | 405C gp140 | $1.04 \times 10^3$ | $1.51 \times 10^{-3}$ | $1.45 \times 10^{-6}$ |
|  | 405C gp120 | Nb | Nb | Nb |
|  | 459C gp140 | Nb | Nb | Nb |
|  | 459C gp120 | Nb | Nb | Nb |
|  | 939C gp140 | $2.41 \times 10^3$ | $2.86 \times 10^{-3}$ | $1.26 \times 10^{-6}$ |
|  | 939C gp120 | Nb | Nb | Nb |
| 2F5 IgG | 405C gp140 | Nb | Nb | Nb |
|  | 459C gp140 | Nb | Nb | Nb |
|  | 939C gp140 | Nb | Nb | Nb |
| 4E10 IgG | 405C gp140 | Nb | Nb | Nb |
|  | 459C gp140 | Nb | Nb | Nb |
|  | 939C gp140 | Nb | Nb | Nb | i. CD4 Binding Site Epitopes

Figures 5A, 5B:
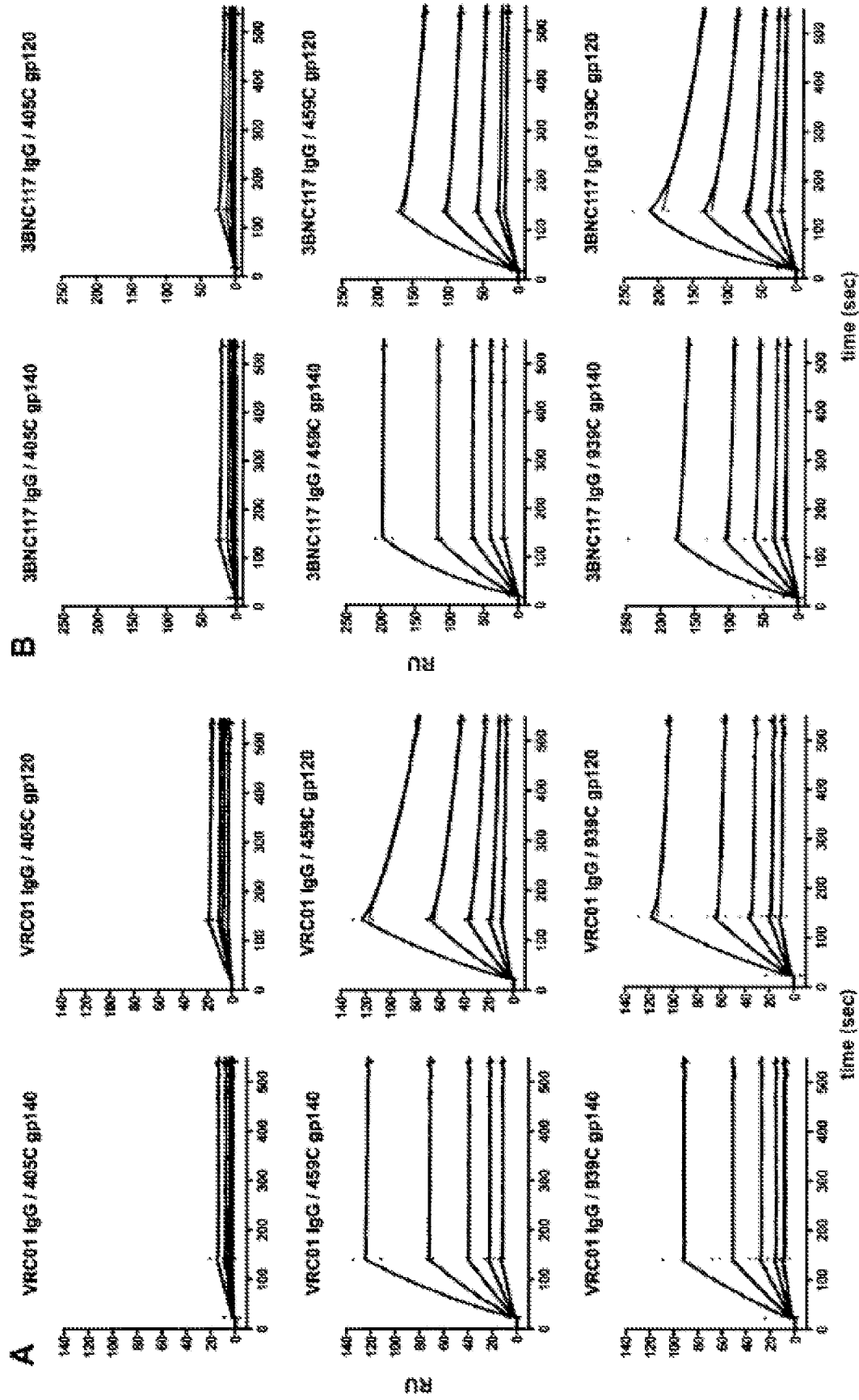
FIG. 5A are SPR sensorgrams showing that of the optimized 405C (top), 459C (middle), and 939C (bottom) gp140 trimers (left) and gp120 monomers (right), the 405C trimers and monomers bound to the CD4 binding site (CD4bs)-specific antibody, VRC01, at a lower magnitude compared to 459C and 939C trimers and monomers. Protein A was irreversibly coupled to a CM5 chip and VRC01 IgG was captured. 405C, 459C, or 939C trimer or monomer was flowed over the bound IgG at concentrations of 62.5-1000 nM. Sensorgrams presented in black. Kinetic fits in green. RU, response units.
FIG. 5B are SPR sensorgrams showing that of the optimized 405C (top), 459C (middle), and 939C (bottom) gp140 trimers (left) and gp120 monomers (right), the 405C trimers and monomers bound to the CD4bs-specific antibody, 3BNC117, at a lower magnitude compared to 459C and 939C trimers and monomers. Protein A was irreversibly coupled to a CM5 chip and 3BNC117 IgG was captured. 405C, 459C, or 939C trimer or monomer was flowed over the bound IgG at concentrations of 62.5-1000 nM. Sensorgrams presented in black. Kinetic fits in green. RU, response units.

We also assessed the ability of broadly neutralizing antibodies to the CD4 binding site, VRC01 and 3BNC117, to bind to our novel clade C trimers and monomers. It is of critical importance for a universal immunogen to present the epitopes for these antibodies, as the CD4 binding site represents a conserved target in all naturally occurring, infectious HIV isolates. These antibodies are of interest as they represent some of the most broadly neutralizing and potent antibodies discovered to date (Wu et al., 2010; Scheid et al., 2011). While all trimers had similar affinities for VRC01 and 3BNC117 (Table 4), the magnitude of binding differs among the different isolates (FIGS. 5A and 5B). The 405C trimer binds to VRCO1 and 3BNC117 at about a five-fold lower magnitude than 459C and 939C trimers, suggesting that these trimeric proteins differentially present the epitopes to these antibodies. The sequence-matched monomers present similar magnitudes of binding with slightly lower affinities for both of these antibodies. These data demonstrate that 405C presents these CD4-binding site epitopes in a unique manner compared to 459C and 939C.

ii. Glycan and V3 Dependent Epitopes

Figures 6A, 6B:
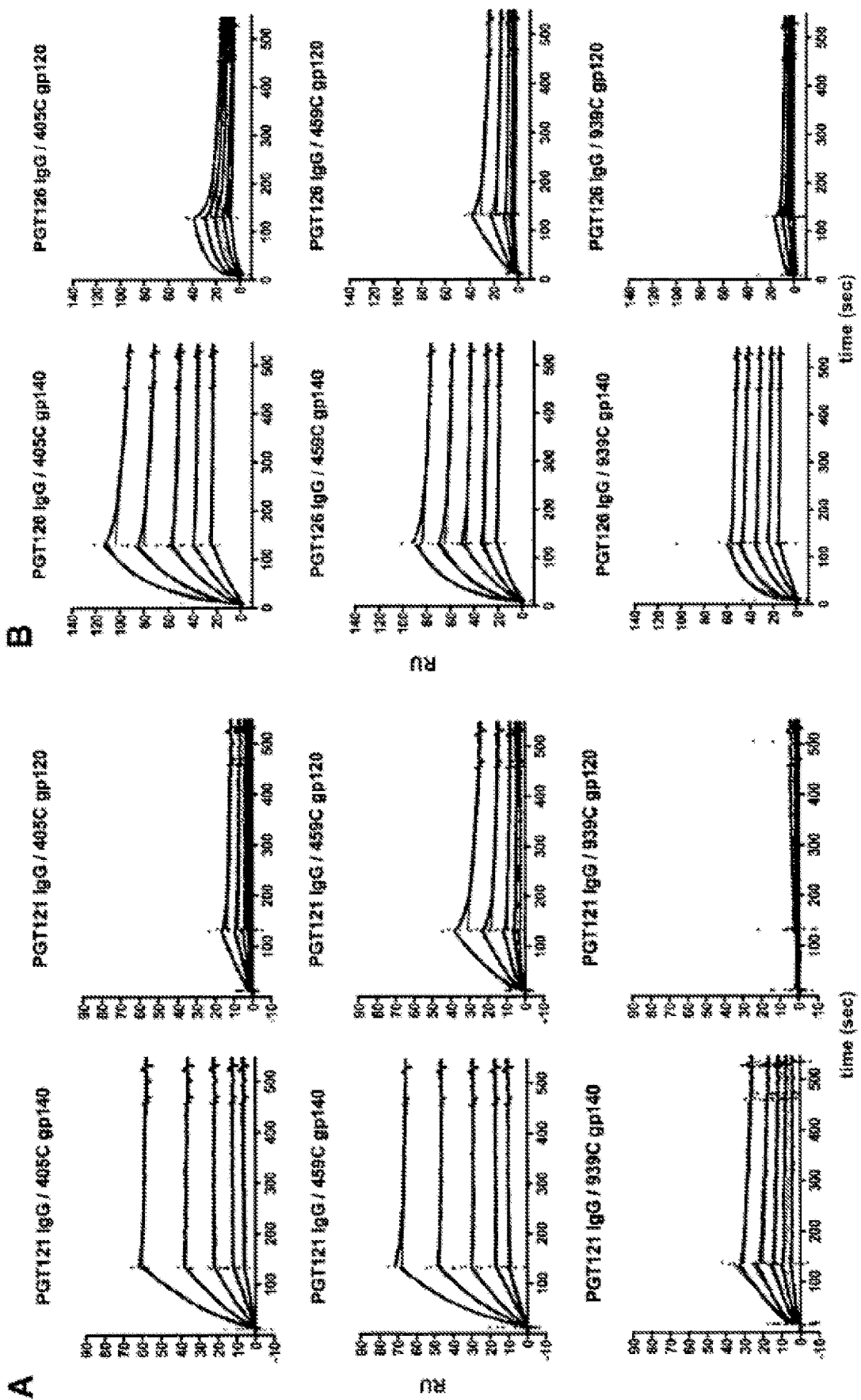
FIG. 6A are SPR sensorgrams showing the presentation of PGT121 epitopes (V3 and glycan-dependent epitopes) by the optimized 405C (top), 459C (middle), and 939C (bottom) gp140 trimers (left) and gp120 monomers (right). For all experiments, protein A was irreversibly coupled to a CM5 chip and PGT121 IgGs were captured. 405C, 459C, and 939C trimers and monomers were flowed over bound PGT121 IgG at concentrations of 62.5-1000 nM. Sensorgrams presented in black. Kinetic fits in green. RU, response units.
FIG. 6B are SPR sensorgrams showing the presentation of PGT126 epitopes (V3 and glycan-dependent epitopes) by the optimized 405C (top), 459C (middle), and 939C (bottom) gp140 trimers (left) and gp120 monomers (right). For all experiments, protein A was irreversibly coupled to a CM5 chip and PGT126 IgGs were captured. 405C, 459C, and 939C trimers and monomers were flowed over bound PGT126 IgG at concentrations of 62.5-1000 nM. Sensorgrams presented in black. Kinetic fits in green. RU, response units.

In addition to assessing the antigenic properties of the receptor and co-receptor binding sites, variable loop and glycan-dependent epitopes were also probed. The PGT family of broadly neutralizing antibodies represents an important family of antibodies to assess the presence of broadly neutralizing epitopes associated with both N-linked glycans and variable loop 3 (V3) (Walker et al., 2011; Pejchal et al., 2011). PGT121, which specifically recognizes N332 and PGT126, which recognizes both N301 and N332, were utilized to probe potential differences in glycosylation patterns. These two antibodies differ in their potency, as PGT121 is known to be 300-times more potent than PGT126 in its neutralization capacity. 405C and 459C trimers bound to PGT121 at a higher magnitude than the 939C trimer, but with similar affinities (FIG. 6A; Table 4). This is expected as 939C is lacking the N-linked glycan at position 332, which the other two isolates contain. A similar pattern was seen for the trimeric constructs binding to PGT126 (FIG. 6B; Table 4). The monomeric constructs presented an unexpected phenotype in that all three clade C monomers bound PGT121 and PGT126 with a lower magnitude and affinity than their sequence-matched trimers, with no binding seen between the 939C monomer and PGT121 (FIG. 6A). The kinetics of the off-rate for these monomers did not accurately fit any of the binding models provided by the BIAevaluation software, and thus, the kinetic rates for the monomers are rough estimates. These data suggest that while the 939C trimer does not present the PGT epitopes, the 405C and 459C trimer do contain this epitope. Additionally, these two antibodies may have trimer-specific binding properties.

iii. Quaternary Epitopes

Figures 7A, 7B:
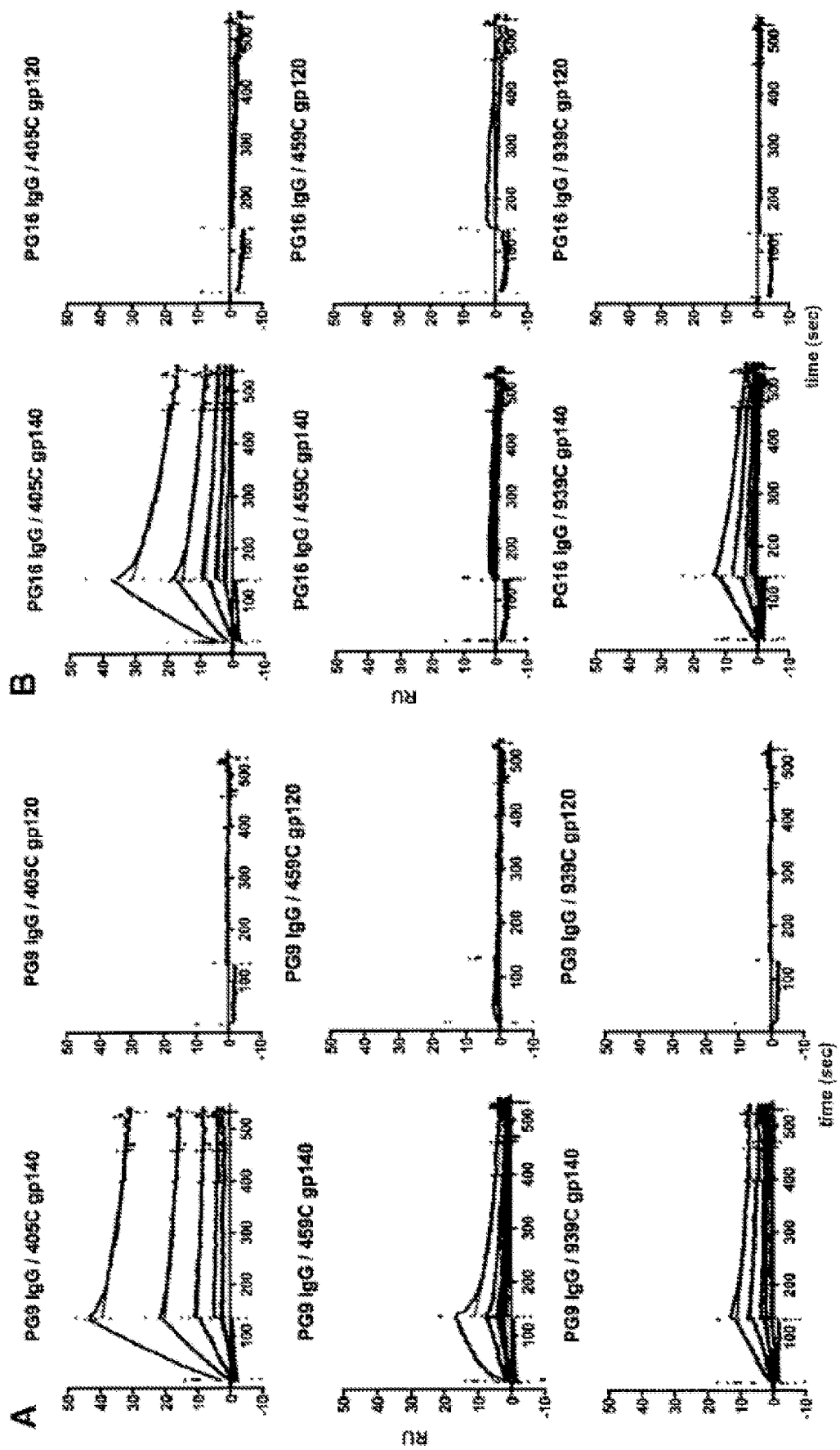
FIG. 7A are SPR sensorgrams showing the presentation of PG9 epitopes (V1/V2, glycan-dependent, quaternary epitopes) by the optimized 405C (top), 459C (middle), and 939C (bottom) gp140 trimers (left) and gp120 monomers (right). For all experiments, protein A was irreversibly coupled to a CM5 chip and PG9 IgGs were captured. 405C, 459C, and 939C trimers and monomers were flowed over bound PG9 IgG at concentrations of 62.5-1000 nM. Sensorgrams presented in black. Kinetic fits in green. RU, response units.
FIG. 7B are SPR sensorgrams showing the presentation of PG16 epitopes (V1/V2, glycan-dependent, quaternary epitopes) by the optimized 405C (top), 459C (middle), and 939C (bottom) gp140 trimers (left) and gp120 monomers (right). For all experiments, protein A was irreversibly coupled to a CM5 chip and PG16 IgGs were captured. 405C, 459C, and 939C trimers and monomers were flowed over bound PG16 IgG at concentrations of 62.5-1000 nM. Sensorgrams presented in black. Kinetic fits in green. RU, response units.

The quaternary structure of the acute, clade C gp140 immunogens was assessed utilizing PG9 and PG16. These antibodies both bind preferentially to envelope proteins with quaternary structure, targeting V1/V2 and N-linked glycans in this region (Walker et al., 2009; McLellan et al., 2011). While some monomeric envelope proteins are known to bind to PG9 (Pejchal et al., 2010; McLellan et al., 2010; Doores et al., 2010; Davenport et al., 2011), none of our acute, clade C monomers bound to PG9 or PG16 (FIGS. 7A and 7B). In contrast, all three trimers bound to PG9 at low levels, suggesting that these trimers may present some degree of quaternary structure. In contrast, PG16 appears to only bind to the 405C and 939C trimers. Binding by PG9 and PG16 to these trimers, however, required a high RU of antibody to see binding (3,500 RU and 4,500 RU, respectively), and PG9 and PG16 are notoriously difficult antibodies to get to bind to proteins immunogens, and seem to preferentially bind surface expressed trimer (Walker et al., 2009).

iv. Membrane Proximal External Region (MPER) Epitopes

Figure 8A:
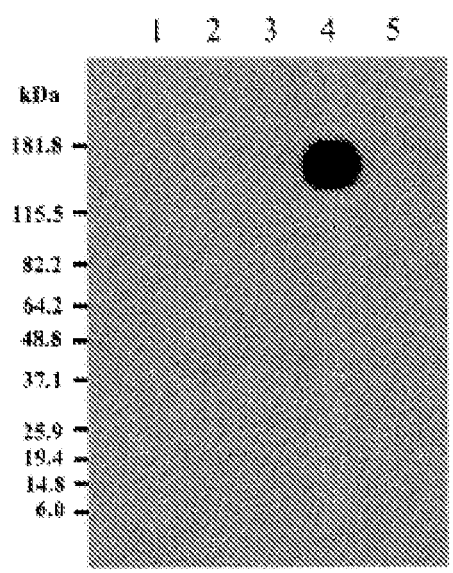
FIG. 8A is a sequence alignment of the 2F5 epitope (membrane-proximal external region epitope) and the 405C, 459C, and 939C trimer sequences from nucleotides 660 to 669.
Figure 8B:
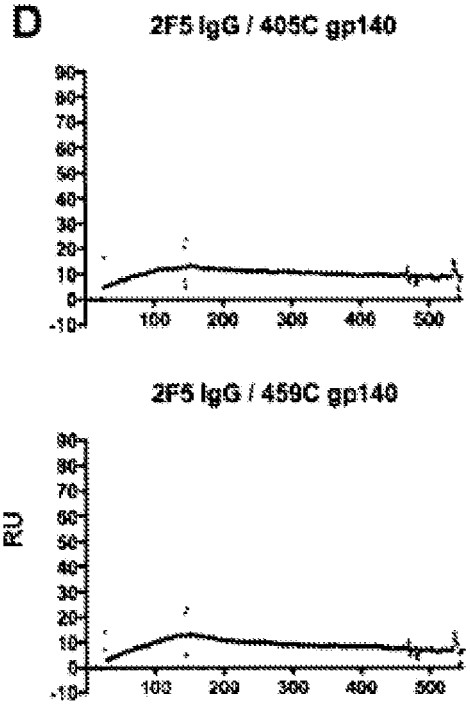
FIG. 8B is a Western blot of 2F5 to (1) 405C, (2) 459C, (3) 939C, (4) positive control 92UG037.8 gp140, and (5) negative control C97ZA012 gp120.
Figure 8C:
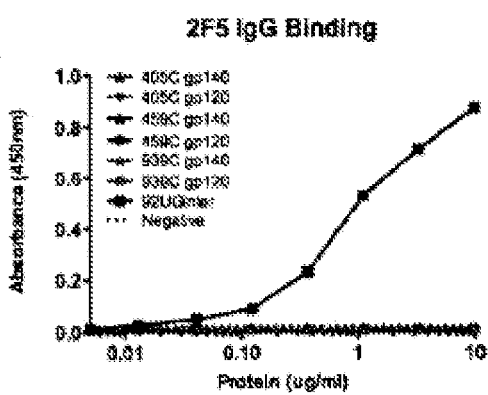
FIG. 8C is a graph showing an ELISA of 405C, 459C, and 939C trimers (gp140) and monomers (gp120) binding to 2F5. Positive control (92UG037.8 inter) presented as squares, gp140s presented as triangles, gp120s as circles, 405C in green, 459C in blue, 939C in red, background cut-off presented as a dotted line.
Figure 8D:
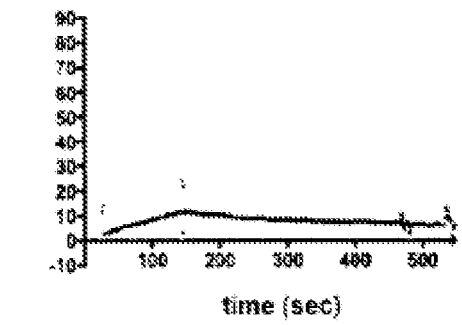
FIG. 8D are SPR sensorgrams showing negligible binding of the 405C (top), 459C (middle), and 939C (bottom) gp140 trimers to 2F5. Protein A was irreversibly coupled to a CM5 chip and 2F5 IgG was captured. 405C, 459C, or 939C was flowed over the bound IgG at a concentration of 1000 nM. Sensorgram in black. RU, response units.
Figures 9A, 9B, 9C, 9D:
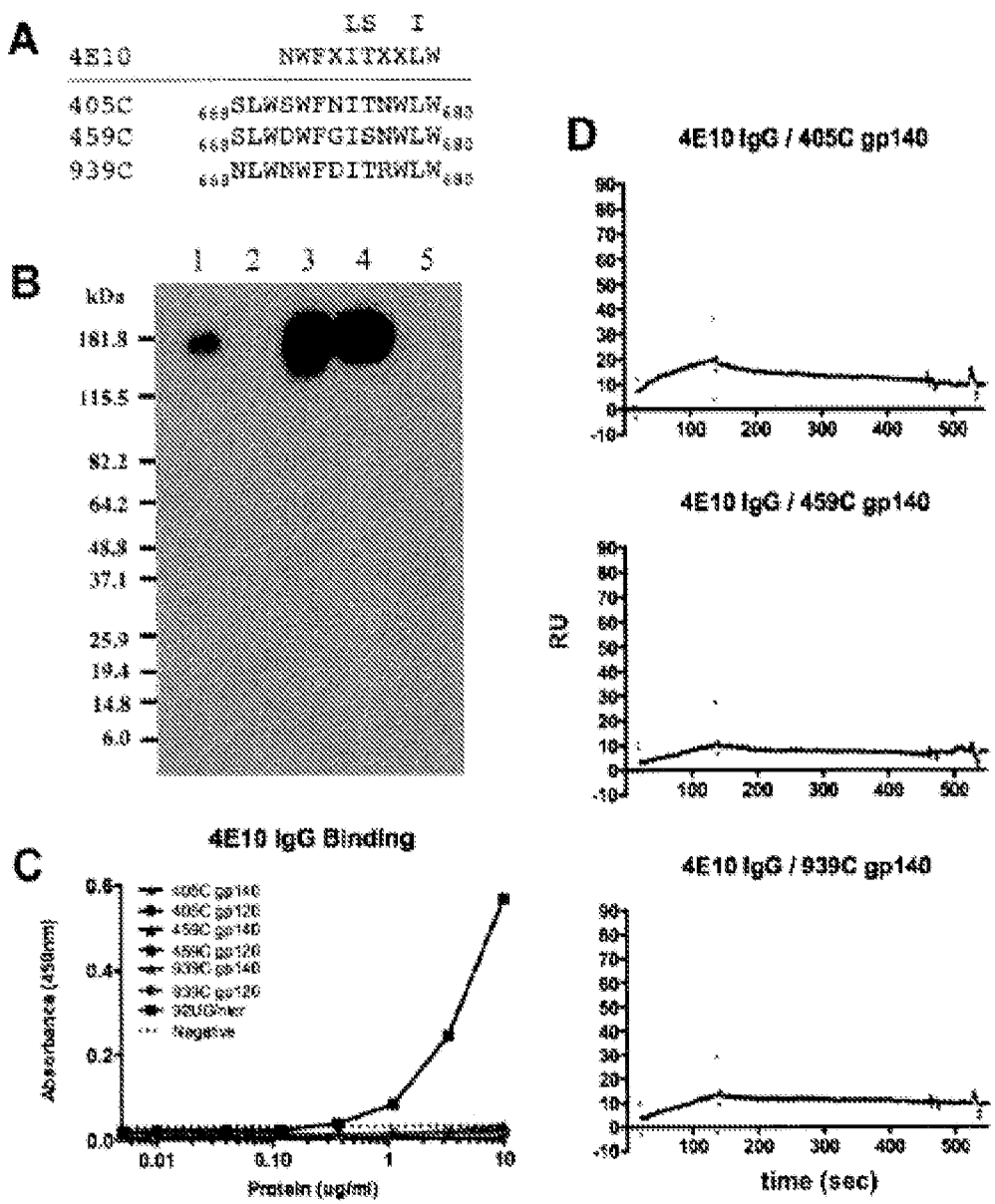
FIG. 9A is a sequence alignment of the 4E10 epitope (membrane-proximal external region epitope) and the 405C, 459C, and 939C trimer sequences from nucleotides 660 to 669.
FIG. 9B is a Western blot of 4E10 to (1) 405C, (2) 459C, (3) 939C, (4) positive control 92UG037.8 gp140, and (5) negative control C97ZA012 gp120.
FIG. 9C is a graph showing an ELISA of 405C, 459C, and 939C trimers (gp140) and monomers (gp120) binding to 4E10. Positive control (92UG037.8 inter) presented as squares, gp140s presented as triangles, gp120s as circles, 405C in green, 459C in blue, 939C in red, background cut-off presented as a dotted line.
FIG. 9D are SPR sensorgrams showing negligible binding of the 405C (top), 459C (middle), and 939C (bottom) gp140 trimers to 4E10. Protein A was irreversibly coupled to a CM5 chip and 4E10 IgG was captured. 405C, 459C, or 939C was flowed over the bound IgG at a concentration of 1000 nM. Sensorgram in black. RU, response units.

As each of the trimers contain the membrane proximal external region (MPER), the presence of known epitopes in this region was assessed. 2F5 and 4E10 broadly neutralizing antibodies are to known linear epitopes, thus we first determined if the sequences corresponding to these antibody's epitopes were present in the acute, clade C immunogens (Ofek et al., 2004; Cardoso et al., 2005; Cardoso et al., 2007). Based on sequence, and confirmed by western blot analysis, none of the clade C trimers contain the 2F5 epitope, which is characteristic of clade C sequences (FIGS. 8A and 8B) (Li et al., 2006). This observation was further confirmed by negligible levels of binding to 2F5 by ELISA and by SPR analysis (FIGS. 8C and 8D; Table 4). Further, the clade C trimers were assessed for their ability to bind 4E10. This epitope allows for more sequence variability for binding than 2F5. While 939C contains the 4E10 epitope, 405C contains one amino acid, which differs from the epitope and 459C does not contain the epitope (FIG. 9A). The presence or absence of these epitopes was confirmed by western blot, ELISA, and SPR analyses (FIGS. 9B, 9C, and 9D; Table 4). Low levels of binding in SPR analysis are likely due to low levels of misfolded trimer that present these epitopes. These analyses confirm that none of the acute clade C sequences possess the 2F5 epitope, and while 405C and 939C contain the 4E10 epitope, this epitope is not presented in the context of the folded trimer.

Example 6. Immunogenicity of Novel, Acute Clade C Immunogens

Figure 10:
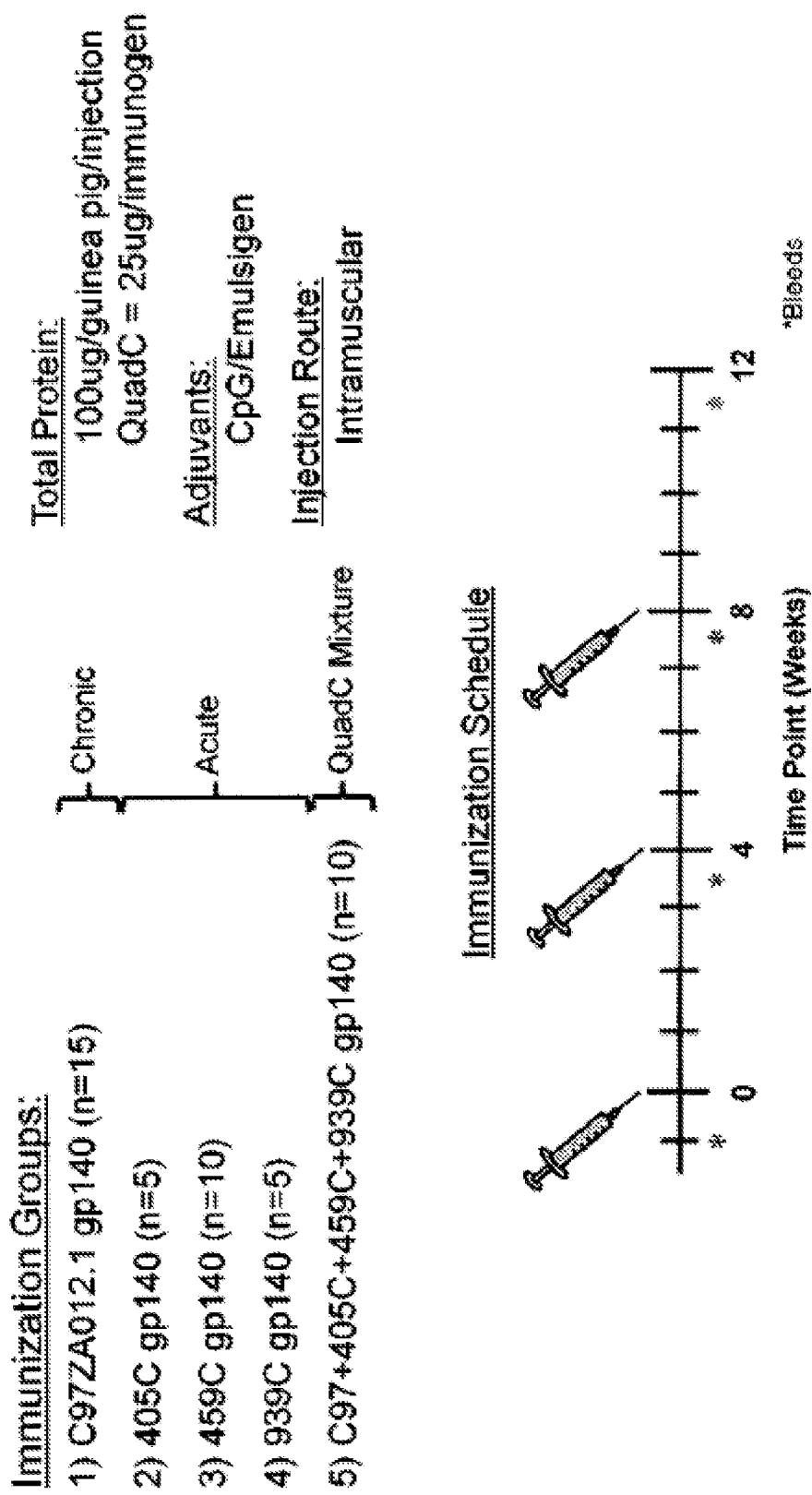
FIG. 10 is a schematic overview of the immunization groups and schedule for assessing the immunogenicity of the novel, acute clade C gp140 trimeric immunogens in monovalent and multivalent regimens.

As 405C, 459C, and 939C are all novel, trimeric immunogens, we assessed the immunogenicity of each of these proteins individually as compared to the C97ZA012.1 trimer, which has been previously characterized and found to be immunogenic in the guinea pig model (Nkolola et al., 2010), as depicted in FIG. 10 (Immunization Groups 1-4). All three proteins were found to be immunogenic, as binding antibody responses were elicited successfully after the first injection, boosted after the second injection, and titering out after the third injection (FIGS. 11A-11D). Binding antibody responses were comparable for all four of the clade C immunogens against all coating proteins, with occasional skewing of responses towards clade C and A coating proteins.

Figures 12A, 12B, 12C, 12D, 12E, 12F, 12G, 12H:
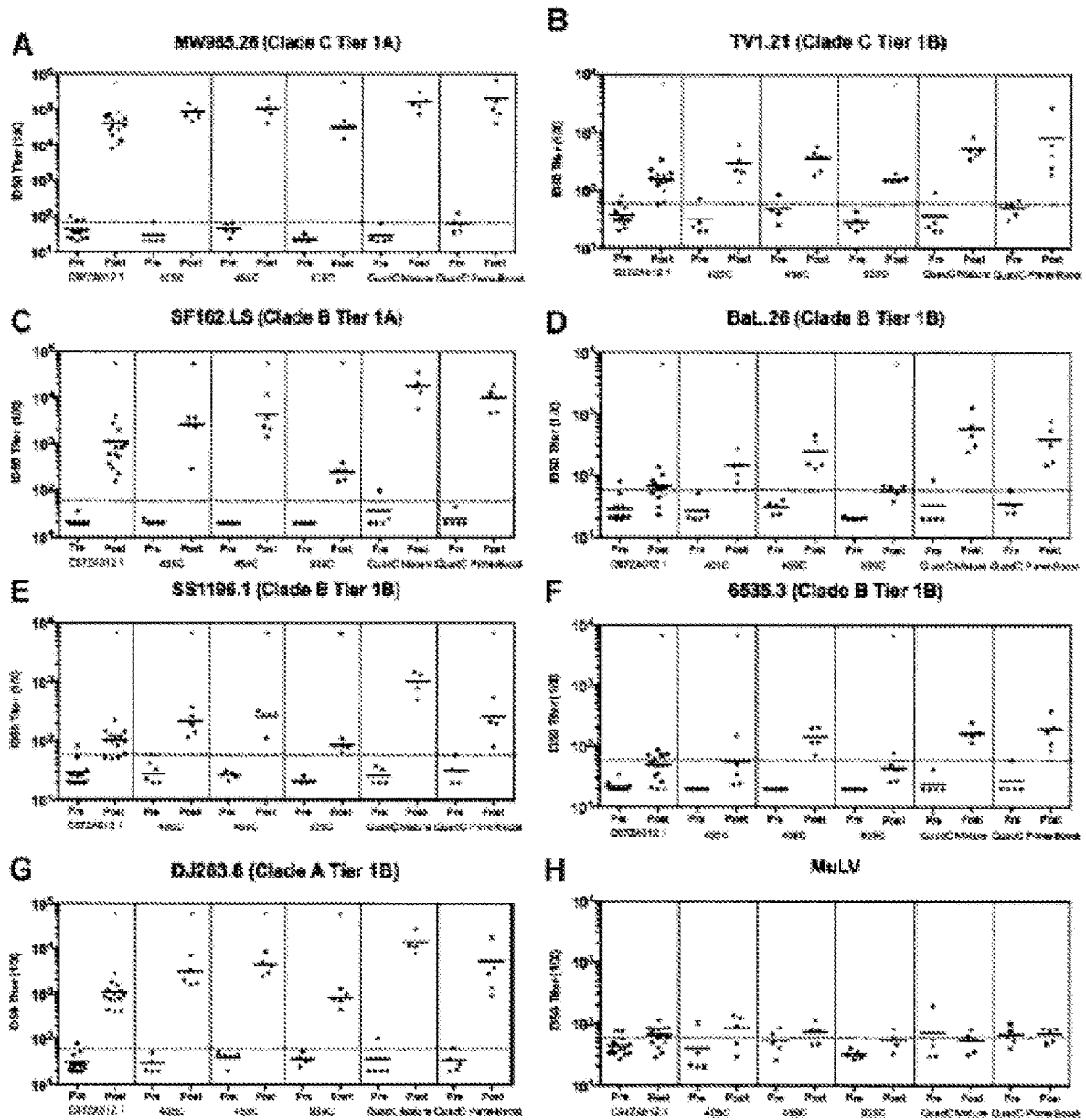
FIG. 12A is a graph showing a quantitative analysis of $ID_{50}$ titer measuring TZM.bl neutralizing antibody responses in guinea pigs pre-vaccination (Pre) and either 4 weeks after the third vaccination (C97ZA012, 405C, 459C, 939C, QuadC) or 4 weeks after the fourth vaccination (QuadC prime-boost) (Post) with optimized C97ZA012, 405C, 459C, 939C, QuadC mixture, or QuadC prime-boost immunogens tested against clade C HIV-1 Env MW965.26 pseudovirions. Horizontal bars indication median titers, dotted black line indicates cut-off for positivity (3× background). *P<0.05 Mann-Whitney U pairwise comparisons to the QuadC mixture. "C97ZA012" represents 14 guinea pigs from three separate experiments.
FIG. 12B is a graph showing a quantitative analysis of $ID_{50}$ titer measuring TZM.bl neutralizing antibody responses in guinea pigs pre-vaccination (Pre) and either 4 weeks after the third vaccination (C97ZA012, 405C, 459C, 939C, QuadC) or 4 weeks after the fourth vaccination (QuadC prime-boost) (Post) with optimized C97ZA012, 405C, 459C, 939C, QuadC mixture, or QuadC prime-boost immunogens tested against clade C HIV-1 Env TV1.21 pseudovirions. Horizontal bars indication median titers, dotted black line indicates cut-off for positivity (3× background). *P<0.05 Mann-Whitney U pairwise comparisons to the QuadC mixture. "C97ZA012" represents 14 guinea pigs from three separate experiments.
FIG. 12C is a graph showing a quantitative analysis of $ID_{50}$ titer measuring TZM.bl neutralizing antibody responses in guinea pigs pre-vaccination (Pre) and either 4 weeks after the third vaccination (C97ZA012, 405C, 459C, 939C, QuadC) or 4 weeks after the fourth vaccination (QuadC prime-boost) (Post) with optimized C97ZA012, 405C, 459C, 939C, QuadC mixture, or QuadC prime-boost immunogens tested against clade B HIV-1 Env SF162.LS pseudovirions. Horizontal bars indication median titers, dotted black line indicates cut-off for positivity (3× background). *P<0.05 Mann-Whitney U pairwise comparisons to the QuadC mixture. "C97ZA012" represents 14 guinea pigs from three separate experiments.
FIG. 12D is a graph showing a quantitative analysis of $ID_{50}$ titer measuring TZM.bl neutralizing antibody responses in guinea pigs pre-vaccination (Pre) and either 4 weeks after the third vaccination (C97ZA012, 405C, 459C, 939C, QuadC) or 4 weeks after the fourth vaccination (QuadC prime-boost) (Post) with optimized C97ZA012, 405C, 459C, 939C, QuadC mixture, or QuadC prime-boost immunogens tested against clade B HIV-1 Env BaL.26 pseudovirions. Horizontal bars indication median titers, dotted black line indicates cut-off for positivity (3× background). *P<0.05 Mann-Whitney U pairwise comparisons to the QuadC mixture. "C97ZA012" represents 14 guinea pigs from three separate experiments.
FIG. 12E is a graph showing a quantitative analysis of $ID_{50}$ titer measuring TZM.bl neutralizing antibody responses in guinea pigs pre-vaccination (Pre) and either 4 weeks after the third vaccination (C97ZA012, 405C, 459C, 939C, QuadC) or 4 weeks after the fourth vaccination (QuadC prime-boost) (Post) with optimized C97ZA012, 405C, 459C, 939C, QuadC mixture, or QuadC prime-boost immunogens tested against clade B HIV-1 Env SS1196.1 pseudovirions. Horizontal bars indication median titers, dotted black line indicates cut-off for positivity (3× background). *P<0.05 Mann-Whitney U pairwise comparisons to the QuadC mixture. "C97ZA012" represents 14 guinea pigs from three separate experiments.
FIG. 12F is a graph showing a quantitative analysis of $ID_{50}$ titer measuring TZM.bl neutralizing antibody responses in guinea pigs pre-vaccination (Pre) and either 4 weeks after the third vaccination (C97ZA012, 405C, 459C, 939C, QuadC) or 4 weeks after the fourth vaccination (QuadC prime-boost) (Post) with optimized C97ZA012, 405C, 459C, 939C, QuadC mixture, or QuadC prime-boost immunogens tested against clade B HIV-1 Env 6535.3 pseudovirions. Horizontal bars indication median titers, dotted black line indicates cut-off for positivity (3× background). *P<0.05 Mann-Whitney U pairwise comparisons to the QuadC mixture. "C97ZA012" represents 14 guinea pigs from three separate experiments.
FIG. 12G is a graph showing a quantitative analysis of $ID_{50}$ titer measuring TZM.bl neutralizing antibody responses in guinea pigs pre-vaccination (Pre) and either 4 weeks after the third vaccination (C97ZA012, 405C, 459C, 939C, QuadC) or 4 weeks after the fourth vaccination (QuadC prime-boost) (Post) with optimized C97ZA012, 405C, 459C, 939C, QuadC mixture, or QuadC prime-boost immunogens tested against clade A HIV-1 Env DJ263.8 pseudovirions. Horizontal bars indication median titers, dotted black line indicates cut-off for positivity (3× background). *P<0.05 Mann-Whitney U pairwise comparisons to the QuadC mixture. "C97ZA012" represents 14 guinea pigs from three separate experiments.
FIG. 12H is a graph showing a quantitative analysis of $ID_{50}$ titer measuring TZM.bl neutralizing antibody responses in guinea pigs pre-vaccination (Pre) and either 4 weeks after the third vaccination (C97ZA012, 405C, 459C, 939C, QuadC) or 4 weeks after the fourth vaccination (QuadC prime-boost) (Post) with optimized C97ZA012, 405C, 459C, 939C, QuadC mixture, or QuadC prime-boost immunogens tested against MuLV (negative control). Horizontal bars indication median titers, dotted black line indicates cut-off for positivity (3× background). *P<0.05 Mann-Whitney U pairwise comparisons to the QuadC mixture. "C97ZA012" represents 14 guinea pigs from three separate experiments.

In addition to assessing binding antibody responses, neutralizing responses were measured. Vaccination with 405C or 459C resulted in a greater magnitude of neutralizing antibodies than C97ZA012 or 939C alone against clade C isolates MW965.26 and TV1.21 (FIGS. 12A and 12B, respectively). Additionally, vaccination with 405C or 459C resulted in a greater magnitude of neutralizing antibodies against clade B isolates SF162.LS (FIG. 12C), BaL.26 (FIG. 12D), SS1196.1 (FIG. 12E), and clade A isolate DJ263.8 (FIG. 12G) than C97ZA012 or 939C alone. The 459C immunogen was unique, in that it resulted in a greater breadth of neutralization than any other clade C immunogen, in that it successfully elicited neutralizing antibodies against the 6535.3 clade B pseudovirion (FIG. 12F). This data suggests that while all of the novel, acute clade C immunogens are immunogenic, 405C and 459C are capable of generating a greater magnitude of neutralizing antibodies than C97ZA012 and 939C when used as single immunogens, and that 459C is capable of generating a greater breadth of neutralization than the other clade C immunogens.

Example 7. Immunogenicity of Multivalent, Clade C Vaccination Regimens

As each of our novel, acute clade C immunogens were immunogenic, and 405C and 459C elicited a greater magnitude and breadth of neutralizing antibody responses than our previously characterized C97ZA012 immunogen, we assessed the magnitude and breadth of neutralizing antibody responses in multivalent vaccination regimens. We conducted different multivalent vaccination regimens. The first multivalent regimen included 405C, 459C, 939C, and C97ZA012 mixed to each constitute one-quarter of the mixture to a total mass of 100 ug of protein, and this mixture was given monthly for three months (QuadC Mixture). The goal of this vaccination regimen was to elicit the greatest number of antibodies to the diversity of epitopes present in the four immunogens. The second multivalent regimen was a heterologous prime-boost regimen in which animals were vaccinated monthly for four months, and were primed with 100 ug C97ZA012, and boosted with 100 ug of 459C, 405C, and 939C, respectively (QuadC Prime-Boost). The goal of this vaccination regimen was to immunofocus neutralizing antibody responses on epitopes that are conserved in four protein immunogens.

Figures 11A, 11B, 11C, 11D, 11E:
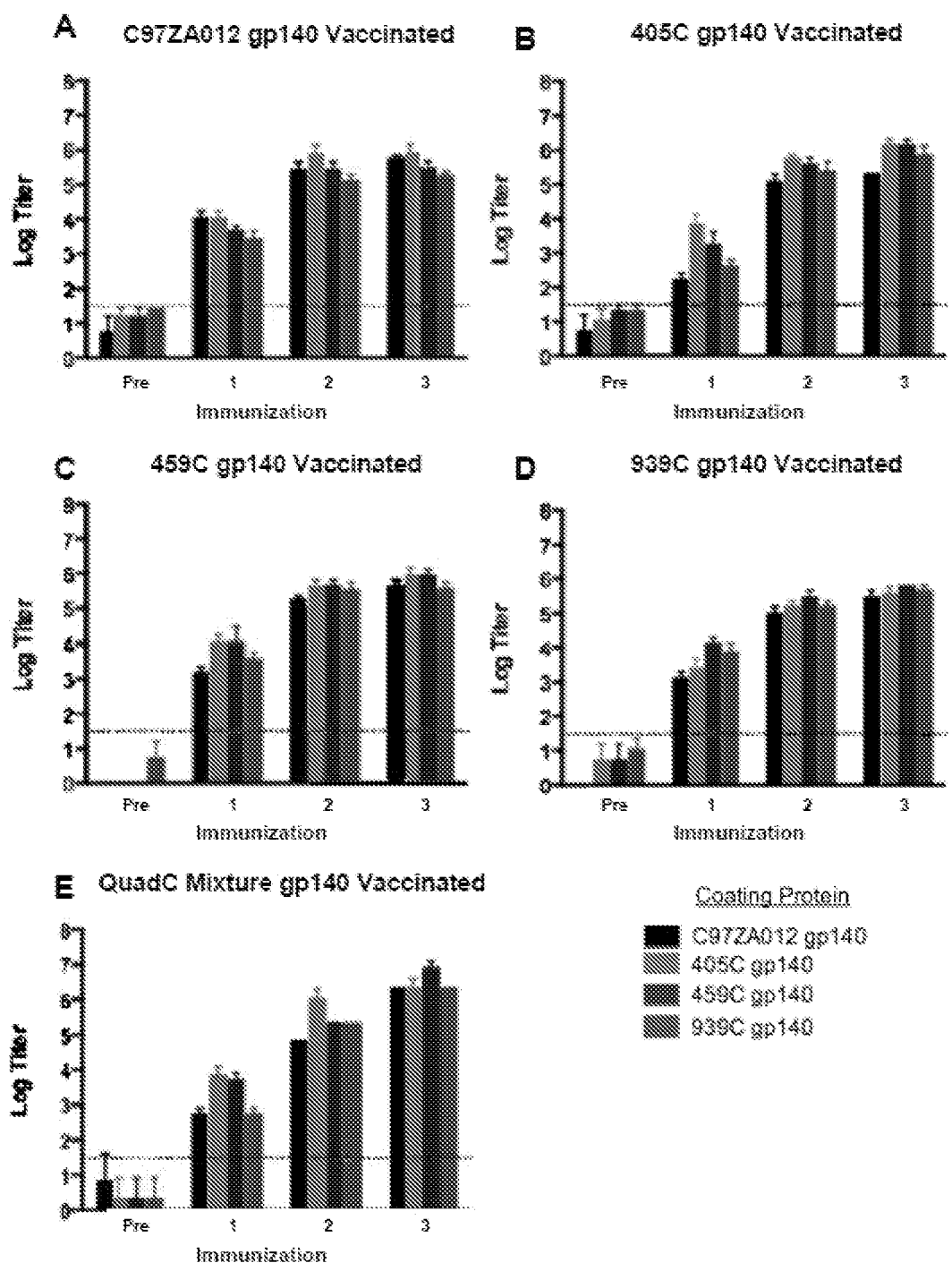
FIG. 11A is a graph of the binding antibody titers from guinea pig sera obtained from guinea pigs pre-immunization (Pre), at 4 weeks post-immunization (1), at 8 weeks post-immunization (2), and at 12 weeks post-immunization (3) with trimeric C97ZA012 gp140 monovalent immunogen. Data are presented as geometric mean titers at each time point+standard deviations. The dotted horizontal line indicates the background threshold.
FIG. 11B is a graph of the binding antibody titers from guinea pig sera obtained from guinea pigs pre-immunization (Pre), at 4 weeks post-immunization (1), at 8 weeks post-immunization (2), and at 12 weeks post-immunization (3) with trimeric 405C gp140 monovalent immunogen. Data are presented as geometric mean titers at each time point+ standard deviations. The dotted horizontal line indicates the background threshold.
FIG. 11C is a graph of the binding antibody titers from guinea pig sera obtained from guinea pigs pre-immunization (Pre), at 4 weeks post-immunization (1), at 8 weeks post-immunization (2), and at 12 weeks post-immunization (3) with trimeric 459C gp140 monovalent immunogen. Data are presented as geometric mean titers at each time point+ standard deviations. The dotted horizontal line indicates the background threshold.
FIG. 11D is a graph of the binding antibody titers from guinea pig sera obtained from guinea pigs pre-immunization (Pre), at 4 weeks post-immunization (1), at 8 weeks post-immunization (2), and at 12 weeks post-immunization (3) with trimeric 939C gp140 monovalent immunogen. Data are presented as geometric mean titers at each time point+ standard deviations. The dotted horizontal line indicates the background threshold.
FIG. 11E is a graph of the binding antibody titers from guinea pig sera obtained from guinea pigs pre-immunization (Pre), at 4 weeks post-immunization (1), at 8 weeks post-immunization (2), and at 12 weeks post-immunization (3) with the multivalent QuadC mixture (C97ZA012+405C+459C+939C) of trimeric gp140 immunogens. Data are presented as geometric mean titers at each time point+standard deviations. The dotted horizontal line indicates the background threshold.
Figure 13A:
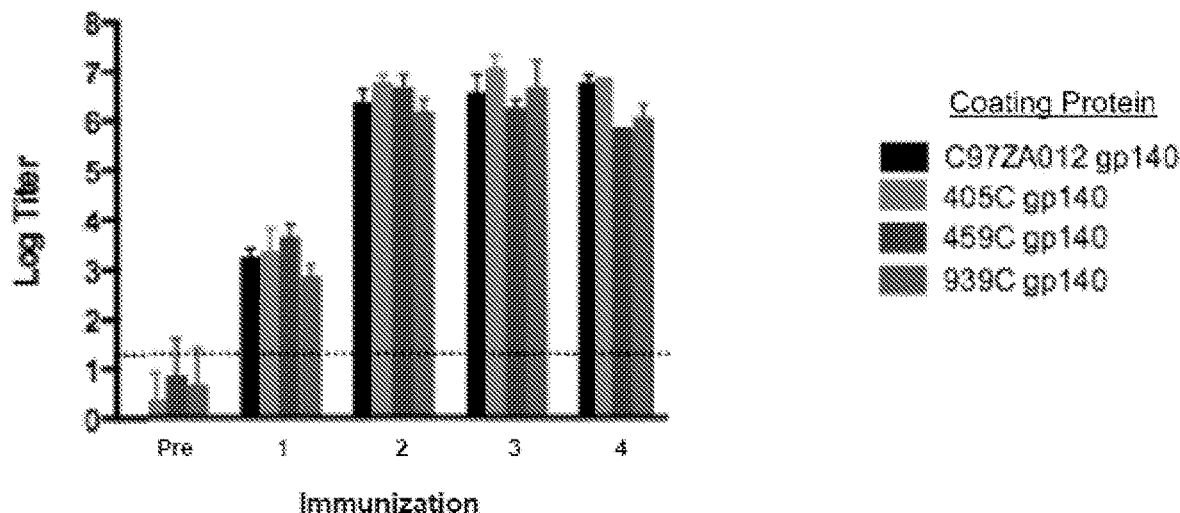
FIG. 13A is a graph of the binding antibody titers from guinea pig sera obtained from guinea pigs pre-immunization (Pre), at 4 weeks post-immunization (1), at 8 weeks post-immunization (2), at 12 weeks post-immunization (3), and at 16 weeks post-immunization in the context of a prime-boost regimen in which animals were primed with 100 µg C97ZA012 and boosted with 100 µg of C97ZA012 trimeric protein immunogen. Data are presented as geometric mean titers at each time point+standard deviations. The dotted horizontal line indicates the background threshold.
Figure 13B:
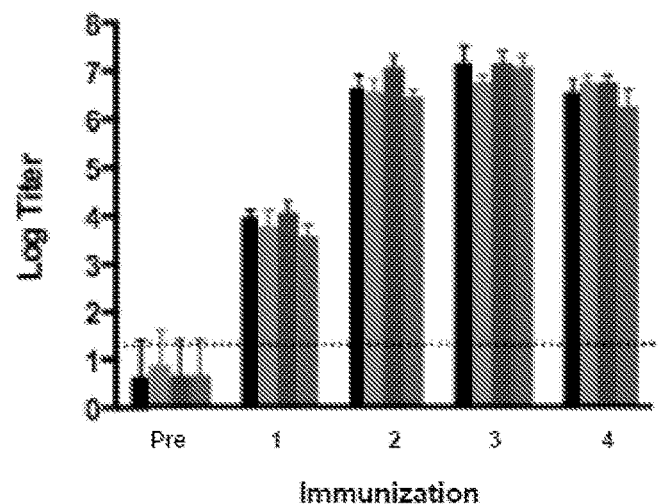
FIG. 13B is a graph of the binding antibody titers from guinea pig sera obtained from guinea pigs pre-immunization (Pre), at 4 weeks post-immunization (1), at 8 weeks post-immunization (2), at 12 weeks post-immunization (3), and at 16 weeks post-immunization in the context of a prime-boost regimen in which animals were primed with 100 µg C97ZA012 and boosted with 100 µg of 405C, 459C, 939C trimeric protein immunogens. Data are presented as geometric mean titers at each time point+standard deviations. The dotted horizontal line indicates the background threshold.

The QuadC mixture was immunogenic, exhibiting similar kinetics and magnitudes of binding antibody responses against each of the coating proteins as any of the single immunogens in the mixture after the first and second vaccination (FIG. 11E). The QuadC mixture had a slight increase in binding magnitude for all coating proteins after the third immunization, which was not seen with any of the single immunogens. In a similar manner, the QuadC prime-boost exhibited similar binding kinetics and titers against all corresponding coating proteins to its corresponding C97ZA012 only control group (FIGS. 13A and 13B). These data suggest that binding antibody responses for the monovalent versus multivalent vaccination groups are comparable.

As we are ultimately interested in obtaining a vaccination regimen that elicits the greatest magnitude and breadth of neutralizing antibody responses, all statistical analyses are conducted in a pairwise fashion (Mann-Whitney U) to the regimen that elicited the greatest magnitude of antibodies for all tested pseudovirions, which in these experiments is the QuadC mixture.

For all tested pseudovirions of clade A, B, and C, except for the clade B isolate SS1196.1, the QuadC mixture and the QuadC prime-boost generated neutralizing antibodies of magnitudes that were not statistically different from each other (FIGS. 12A-12H). This suggests that both multivalent strategies are successful at eliciting neutralizing antibodies and that neither regimen is superior to the other.

Against the clade C pseudovirions MW965.28 and TV1.21, the QuadC mixture elicited a significantly higher magnitude of neutralizing antibodies than either C97ZA012 or 939C alone (FIGS. 12A and 12B). In contrast to this, however, the QuadC mixture did not elicit neutralizing responses that were superior to either 405C or 459C alone against these isolates. This suggests that while the QuadC mixture is superior to C97ZA012 and 939C as individual immunogens, it is likely that 405C and/or 459C are contributing to the increased magnitude of neutralizing antibodies in the QuadC mixture. Additionally, while the QuadC mixture elicits a greater magnitude of neutralizing antibodies against clade B isolates (including BaL.26 and 6535.3) than C97ZA012, 405C, or 939C alone, it does not elicit a magnitude of neutralizing antibodies that are superior to 459C alone (FIGS. 12D and 12F). This suggests that 459C alone is capable of eliciting a greater breadth of neutralizing responses both as a single immunogen and within a mixture of immunogens.

Finally, against clade-mismatched isolates, the QuadC mixture elicited neutralizing antibodies of statistically higher magnitudes against clade B SF162.LS and SS1196.1, as well as clade A DJ263.8, than any single component of the vaccination mixture (FIGS. 12C, 12E, and 12G). This suggests that the mixture of proteins together is capable of eliciting either a greater number of neutralizing antibodies or antibodies to a greater number of epitopes against these isolates, than any single component of the vaccination regimen. Based on our findings, a quadrivalent, clade C mixture of immunogens had superior neutralization properties than vaccinations with single immunogens.

Example 8. A Multivalent Clade C HIV-1 Env Trimer Cocktail Elicits Higher Magnitude Neutralizing Antibodies than any Individual Component The sequence diversity of human immunodeficiency virus type 1 (HIV-1) presents a formidable challenge to the generation of an HIV-1 vaccine. One strategy to address such sequence diversity is to utilize multivalent mixtures of HIV-1 envelope (Env) immunogens. Here we report the generation and characterization of three novel, acute clade C HIV-1 Env gp140 trimers (459C, 405C and 939C), each with unique antigenic properties. We evaluated the immunogenicity of various mixtures of clade C Env trimers and found that a quadrivalent cocktail of clade C trimers elicited a greater magnitude of neutralizing antibodies (NAbs) against a panel of Tier 1A and 1B viruses than any single clade C trimer alone, demonstrating that the mixture had an advantage over any individual component of the cocktail. This is the first time that a cocktail of HIV-1 Env trimers has been shown to elicit a greater magnitude of NAbs than any individual component. These data show that vaccination with a mixture of clade C Env trimers, each with unique antigenic properties, can be used to increase the magnitude of vaccine-elicited NAb responses.

Materials and Methods

Plasmids, Cell Lines, Protein Production, and Antibodies

The full-length gp160 envelope sequences for HIV-1 Env 405C, 459C, and 939C were cloned from virus in acutely infected participants from South Africa (HVTN503) and were generously provided by Dr. Leonidas Stamatatos (Seattle BioMed) (Gray et al., The Lancet Infectious Diseases 11:507-515, 2011). These sequences represent consensus sequences from individual subjects from less than 90 days post-infection.

Codon-optimized synthetic genes for the HIV-1 Env 405C, 459C, and 939C gp140 trimers were produced by GeneArt (Life Technologies). All constructs contained a consensus leader signal sequence peptide, as well as a C-terminal foldon trimerization tag followed by a His-tag as described previously (Nkolola et al., *J. Virol.* 84: 3270-3279, 2010; Frey et al., *Proceedings of the National Academy of Sciences* 105:3739-3744, 2008). The codon-optimized synthetic genes for the full-length HIV-1 Env 405C, 459C, and 939C gp120s were cloned from their respective gp140 construct and a C-terminal His-tag was added. HIV-1 Env C97ZA012.1, 92UG037.8, and Mosaic (MosM.3.1) gp140 were produced as described previously (Nkolola et al., supra; Nkolola et al., *Journal of Virology,* 2014).

All constructs were generated in 293T cells utilizing transient transfections with polyethylenimine. Cell lines were grown in DMEM with 10% FBS to confluence and then changed to Freestyle 293 expression medium for protein purification (Invitrogen). Cell supernatants were harvested five days after medium change, centrifuged for clarification, and brought to a final concentration of 10 mM imidazole.

All His-tagged proteins were purified by HisTrap Ni-NTA column (GE Healthcare). Ni-NTA columns were washed with 20 mM imidazole (pH 8.0) and protein was eluted with 300 mM imidazole (pH 8.0). Fractions containing protein were pooled and concentrated. Protein constructs were further purified utilizing gel filtration chromatography on Superose 6 (GE Healthcare) for gp140 trimeric constructs and Superdex 200 (GE Healthcare) for gp120 monomeric constructs in running buffer containing 25 mM Tris (pH 7.5) and 150 mM sodium chloride. Purified proteins were concentrated using CentriPrep YM-50 concentrators (Millipore), frozen in liquid nitrogen, and stored at −80° C. To assess protein stability, 5 ug of protein was run on an SDS-PAGE gel (Bio-Rad) either after a single freeze/thaw cycle or after incubation at 4° C. for 2 weeks.

Soluble two-domain CD4 was produced as described previously (Freeman et al., Structure 18:1632-1641, 2010).

17b hybridoma was provided by James Robinson (Tulane University, New Orleans, La.) and purified as described previously (Kovacs et al., *PNAS* 109:12111-12116, 2012). VRCO1 was obtained through the NIH AIDS Reagent Program. 3BNC117 and 10-1074 were provided by Michel Nussenzweig (Rockefeller University, New York, N.Y.). PGT121, PGT126, and PGT145 were provided by Dennis Burton (The Scripps Research Institute, La Jolla, Calif.). 2F5, 4E10, and PG9 were purchased from Polymun Scientific.

Surface Plasmon Resonance Binding Analysis

SPR experiments were conducted on a Biacore 3000 (GE Healthcare) at 25° C. utilizing HBS-EP [10 mM Hepes (pH 7.4), 150 mM NaCl, 3 mM EDTA, 0.005% P20] (GE Healthcare) as the running buffer. Immobilization of CD4 (1,500 RU) or protein A (ThermoScientific) to CM5 chips was performed following the standard amine coupling procedure as recommended by the manufacturer (GE Healthcare). Immobilized IgGs were captured at 300-550 RU. Binding experiments were conducted with a flow rate of 50 ul/min with a 2-minute associate phase and a 5-minute dissociation phase. Regeneration was conducted with one injection (3 seconds) of 35 mM sodium hydroxide, 1.3 M sodium chloride at 100 ul/min followed by a 3-minute equilibration phase in HBS-EP. Identical injections over blank surfaces were subtracted from the binding data for analysis. Binding kinetics were determined using BIAevaluation software (GE Healthcare) and the Langmuir 1:1 binding model. A bivalent binding model was used to fit PGT145 IgG binding. All samples were run in duplicate and yielded similar kinetic results. Single curves of the duplicates are shown in all figures.

Guinea Pig Vaccinations

Outbred female Hartley guinea pigs (Elm Hill) were used for all vaccination studies. Guinea pigs were immunized (n=5-14/group) with protein trimers intramuscularly in the quadriceps bilaterally at 4-week intervals for a total of 3 injections. Vaccine formulations for each guinea pig consisted of a total of 100 μg of trimer per injection formulated in 15% Emulsigen (vol/vol) oil-in-water emulsion (MVP Laboratories) and 50 μg CpG (Midland Reagent Company) as adjuvants. In multivalent vaccination regimens, the total amount of injected protein was maintained at 100 μg and divided equally among total the number of immunogens in the mixture. Multivalent mixtures included the C97ZA012 and 459C gp140 trimers [2C Mixture], C97ZA012, 459C, and 405C gp140 trimers [3C Mixture] and C97ZA012, 405C, 459C, and 939C gp140 trimers [4C Mixture]. Serum samples were obtained from the vena cava of anesthetized animals four weeks after each immunization.

Endpoint ELISAs

Serum binding antibodies against gp140 were measured by endpoint enzyme-linked immunosorbant assays (ELISAs) as described previously (Nkolola et al., supra). Briefly, ELISA plates (Thermo Scientific) were coated with individual trimers and incubated overnight. Guinea pig sera were then added in serial dilutions and later detected with an HRP-conjugated goat anti-guinea pig secondary antibody (Jackson ImmunoResearch Laboratories). Plates were developed and read using the Spectramax Plus ELISA plate reader (Molecular Devices) and Softmax Pro-4.7.1 software. End-point titers were considered positive at the highest dilution that maintained an absorbance >2-fold above background values.

TZM.bl Neutralization Assay

Functional neutralizing antibody responses against HIV-1 Env pseudovirions were measured using the TZM.bl neutralization assay, a luciferase-based virus neutralization assay in TZM.bl cells as described previously (Nkolola et al., supra; Montefiori, Curr Protoc Immunol Chapter 12:Unit 12.11, 2005). ID50 was calculated as the serum dilution that resulted in a 50% reduction in relative luminescence units of TZM.bl cells compared to virus-only control wells after the subtraction of a cell-only control. Briefly, serial dilutions of sera were incubated with pseudovirions and then overlaid with TZM.bl cells. Murine leukemia virus (MuLV) was included as a negative control in all assays. HIV-1 Env pseudovirions, including Tier 1 isolates from clade A (DJ263.8, Q23.17, MS208.A1), clade B (SF162.LS, BaL.26, SS1196.1, 6535.3), and clade C (MW965.26, TV1.21, ZM109F.PB4, ZM197M.PB7), and were prepared as described previously (Montefiori, supra).

Results

Generation of Novel, Acute Clade C Env Trimers

Fifteen acute HIV-1 clade C envelope sequences from South Africa (Gray et al., supra) were cloned into a pCMV expression vector and transiently transfected in human endothelial kidney cells 293T cells utilizing polyethylenimine. Expression levels of Env gp140 were compared by western blot utilizing supernatant from transfected cells (FIG. 14A) and expression data were verified by quantitative binding ELISAs. Western blot analysis showed that eight of the fifteen Env gp140s expressed at a level similar to or greater than that of our previously characterized C97ZA012 gp140 (Kovacs et al., supra; Nkolola et al., 2010, supra); 405C, 459C, 939C, 823cD6, 756C, 823C, 349C, and 706C gp140. The remaining Env gp140s, 426C, 590C, 072C, 327C, 431C, 885C, and 140C, exhibited low expression levels. The eight sequences with the highest expression levels were then screened for expression from large-scale purifications.

The three highest expressing Env gp140 constructs from large-scale purifications (405C, 459C, and 939C) were chosen for further biochemical and immunological analyses. These trimers appeared stable, as negligible degradation was seen both after a freeze/thaw cycle and after incubation at 4° C. for two weeks (FIG. 14B). Additionally, each of these trimers represented a homogenous population as measured by gel filtration chromatography (FIG. 14C). Overall, these trimers appear to be stable, homogenous populations of soluble HIV-1 Env trimers.

Phylogenetic Characterization of Novel, Acute Clade C Immunogens

Figures 15A, 15B, 15C, 15D, 15E:
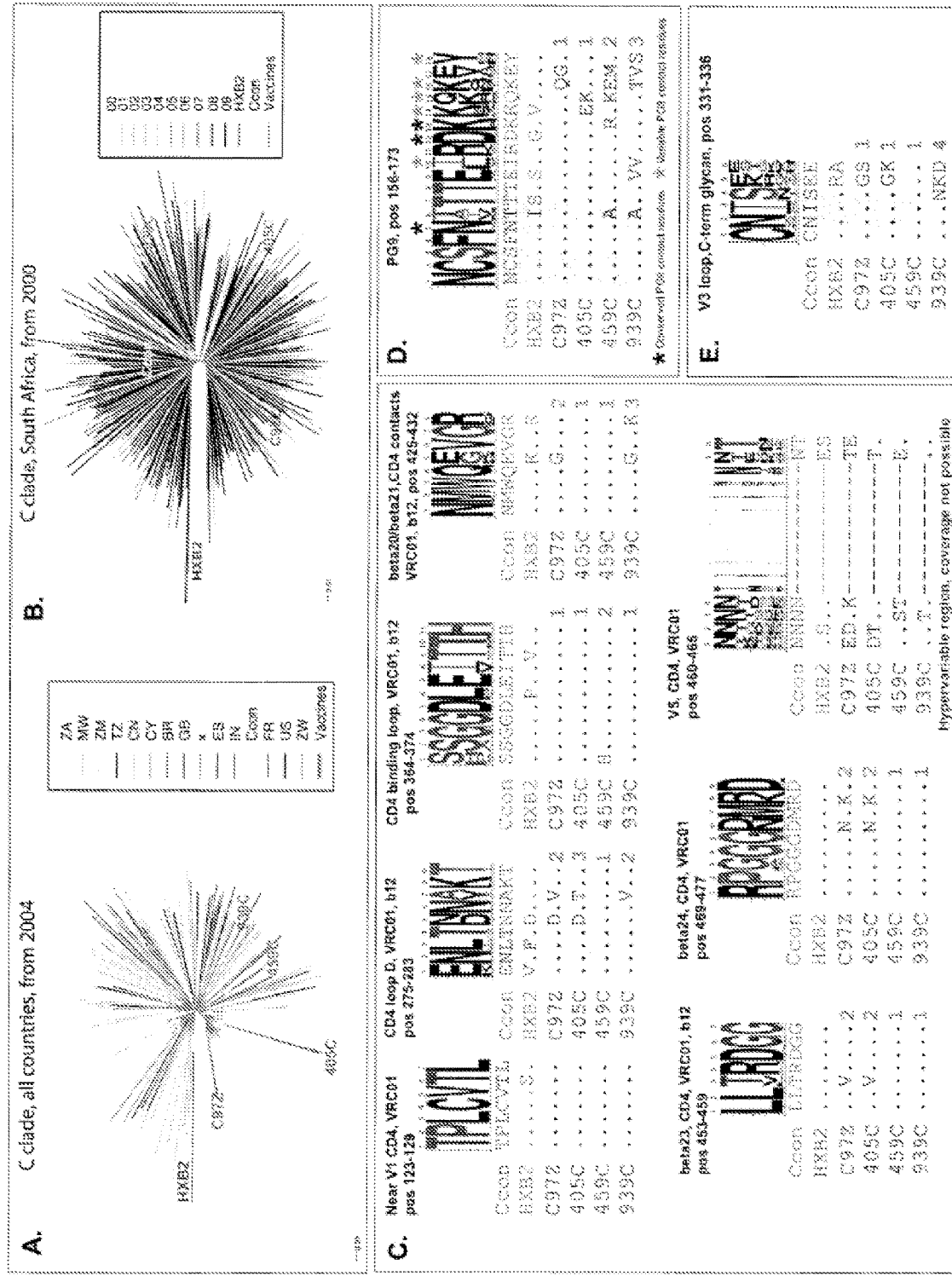
FIGS. 15A-15E are diagrams showing maximum likelihood trees and sequence alignments of clade C gp140 sequences.

We generated a maximum likelihood tree and compared the three novel, acute clade C and the C97ZA012 (Kovacs et al., supra; Nkolola et al., supra) trimer sequences to 489 clade C sequences from different countries and from the same year the acute clade C sequences were isolated (2004) (FIG. 15A). A second tree compared the four gp140 sequences to 506 South African clade C sequences from the years 2000 to 2009 (FIG. 15B). Both of these analyses determined that Env 459C gp140 was the most central of the four sequences, whereas Env 405C gp140 was a sequence outlier.

Sequence analyses were also conducted on specific epitopes to known bNAbs. Env 459C and Env 939C gp140 were closer to the consensus sequence for the CD4 binding site epitope (b12 (Saphire, *Science* 293: 1155-1159, 2001), VRCO1 (Wu et al., *Curr. Protoc. ImmunoL*, Chapter 12: United 12.11, 2010)) than C97ZA012 or 405C gp140 (FIG. 15C). In contrast, Env 405C gp140 was the most central of all of these sequences for PG9/PG16/PGT145-like V1/V2 binding antibodies (Walker et al., *Science* 326: 285-289, 2009; McLellan et al., *Nature* 480: 336-343, 2011; Davenport et al., *J. Virol.* 85: 7095-7107, 2011; Julien et al, *PNAS* 110: 4351-4356, 2013) (FIG. 15D). Additionally, the Env 939C trimer lacked the N-linked glycan at amino acid position 332 (N332; HXB2 reference numbering), which is important for the V3 binding, PGT family of antibodies (Sok et al., *Science Translational Med.* 6:236ra63, 2014; Pejchal et al., *Science* 334: 1097-1103, 2011; Mouquet et al., *PNAS* 109:E3268-3277, 2012; Julien et al., *PLoS Pathog.* 9: e1003342, 2013) (FIG. 15E). These phylogenetic and sequence analyses suggest that each trimer contained unique phylogenetic and sequence characteristics.

Antigenic Properties of Novel, Acute Clade C Immunogens

Figures 16A, 16B, 16C, 16D:
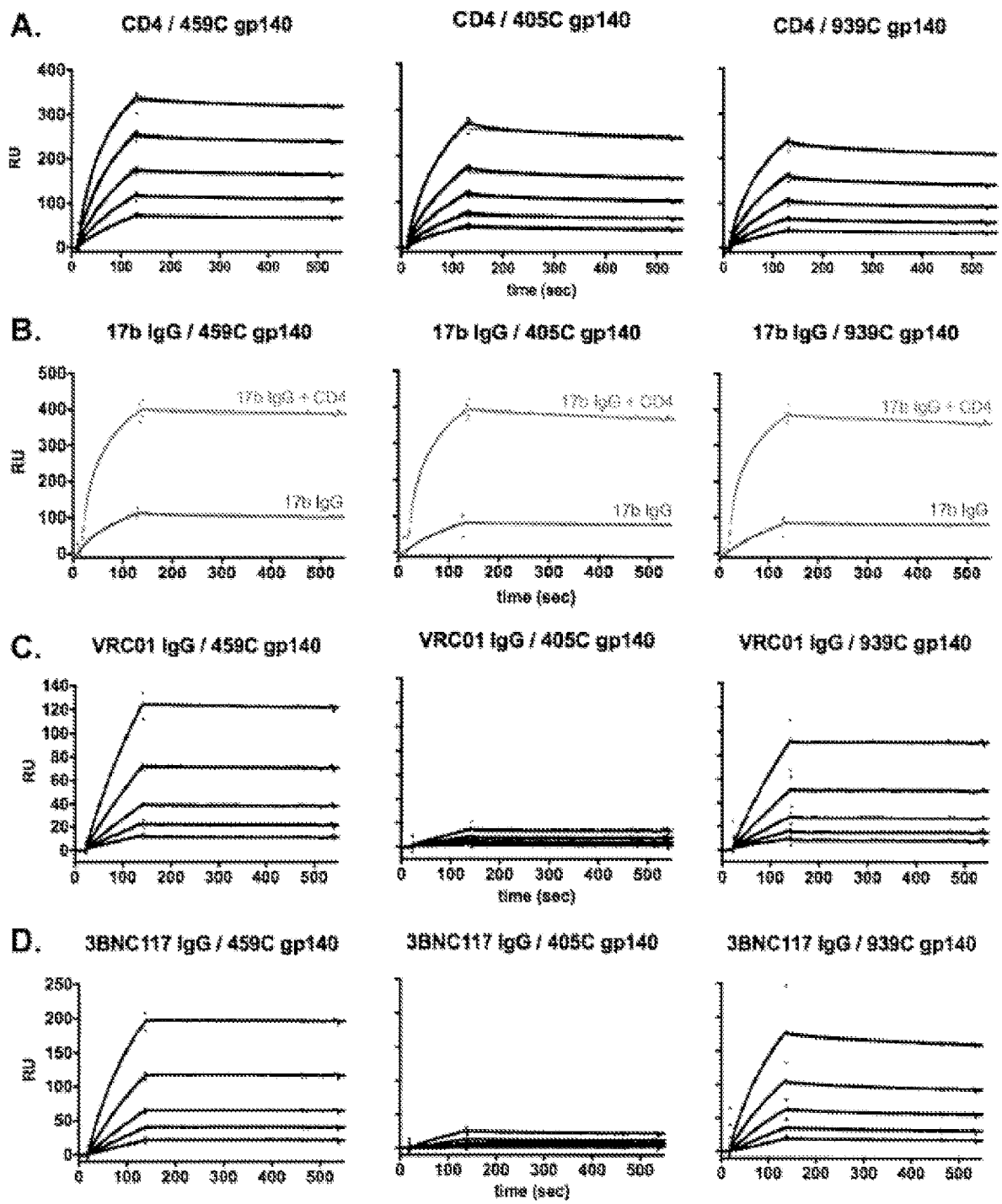
FIGS. 16A-16D are graphs showing presentation of CD4 and CD4i epitopes by acute, clade C trimers.

We next analyzed the antigenic properties of the novel, clade C trimers by surface plasmon resonance (SPR). All of the clade C trimers presented the CD4 binding site and bound well to CD4 (FIG. 16A). While all three trimers showed a low magnitude of 17b IgG (Kwong et al., *Nature* 393:648-659, 1998) binding in the absence of bound CD4, there was a substantial increase in the magnitude of 17b binding in the presence of CD4, as expected (FIG. 16B). While all trimers bound to the CD4 binding site antibodies VRC01 (Zhou et al., supra) and 3BNC117 (Scheid et al., *Science* 333:1633-1637, 2011), the magnitude of binding differed among the different isolates (FIGS. 16C and 16D). In particular, the Env 405C trimer bound VRC01 and 3BNC117 at about a five-fold lower magnitude than Env 459C and 939C trimers, suggesting that 459C and 939C may present the CD4 binding site epitope more optimally than 405C.

Figures 17A, 17B, 17C:
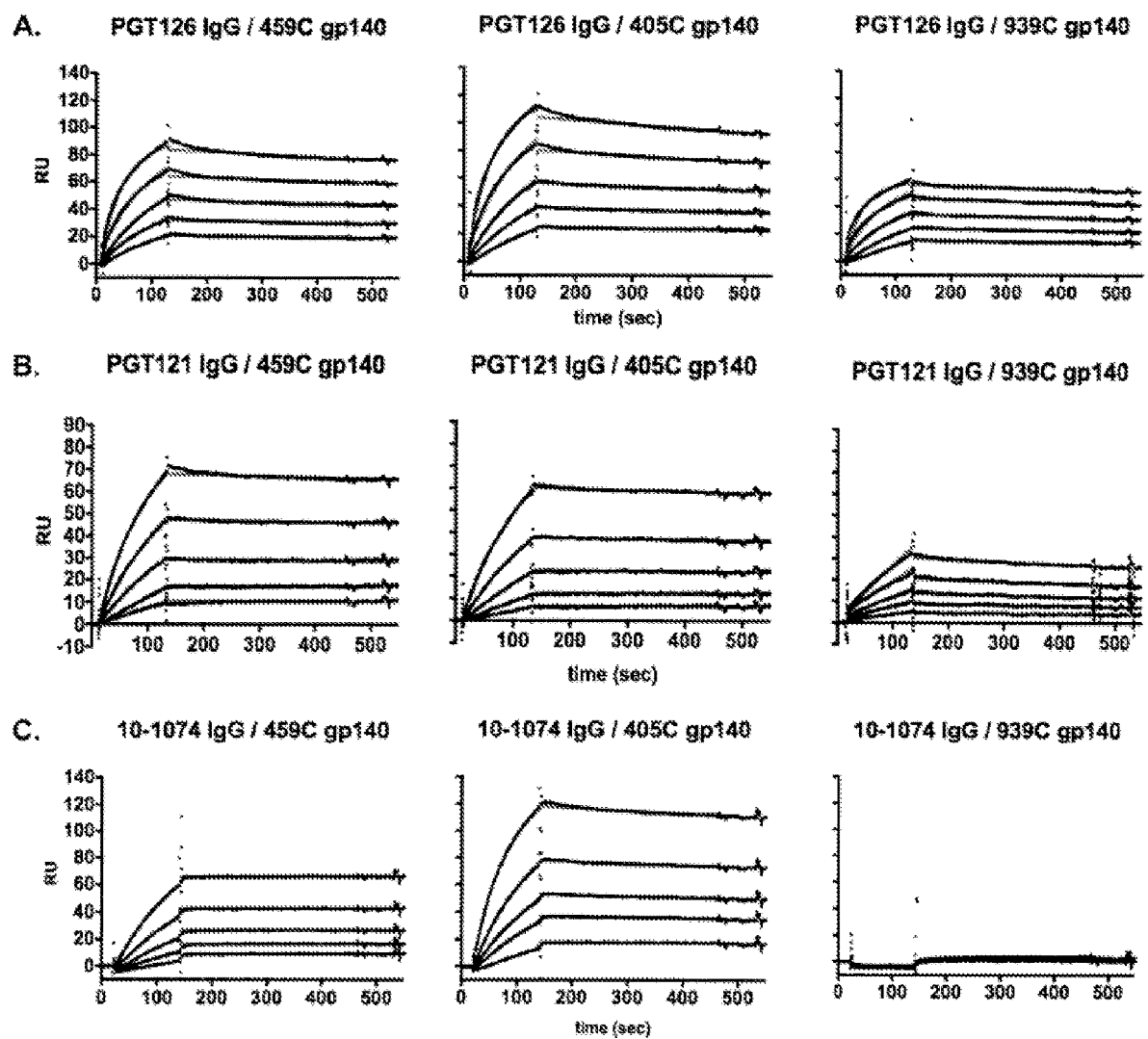
FIGS. 17A-17C are graphs showing presentation of V3 and glycan-dependent epitopes by acute, clade C trimers. For all experiments, protein A was irreversibly coupled to a CM5 chip and IgGs were captured.

The Env 405C and 459C trimers bound the V3 glycan-dependent antibodies PGT121 and PGT126 at a slightly higher magnitude than did Env 939C trimer (FIGS. 17A and 17B). This is expected as Env 939C gp140 lacks the critical N-linked glycan at position 332 (HXB2 reference numbering) that forms part of the epitope for these antibodies (Sok et al., supra; Julien et al., *PLoS Pathog* 9:e1003342, 2013; Pejchal et al., *Science* 334:1097-1103, 2011) (FIG. 15E). Additionally, while Env 405C and 459C gp140s both bound 10-1074, 939C exhibited essentially no binding to this antibody (FIG. 17C), which is expected as N332 is critical for 10-1074 binding (Mouquet et al., *Proceedings of the National Academy of Sciences* 109:E3268-77, 2012).

Figures 18A, 18B, 18C, 18D, 18E, 18F, 18G, 18H:
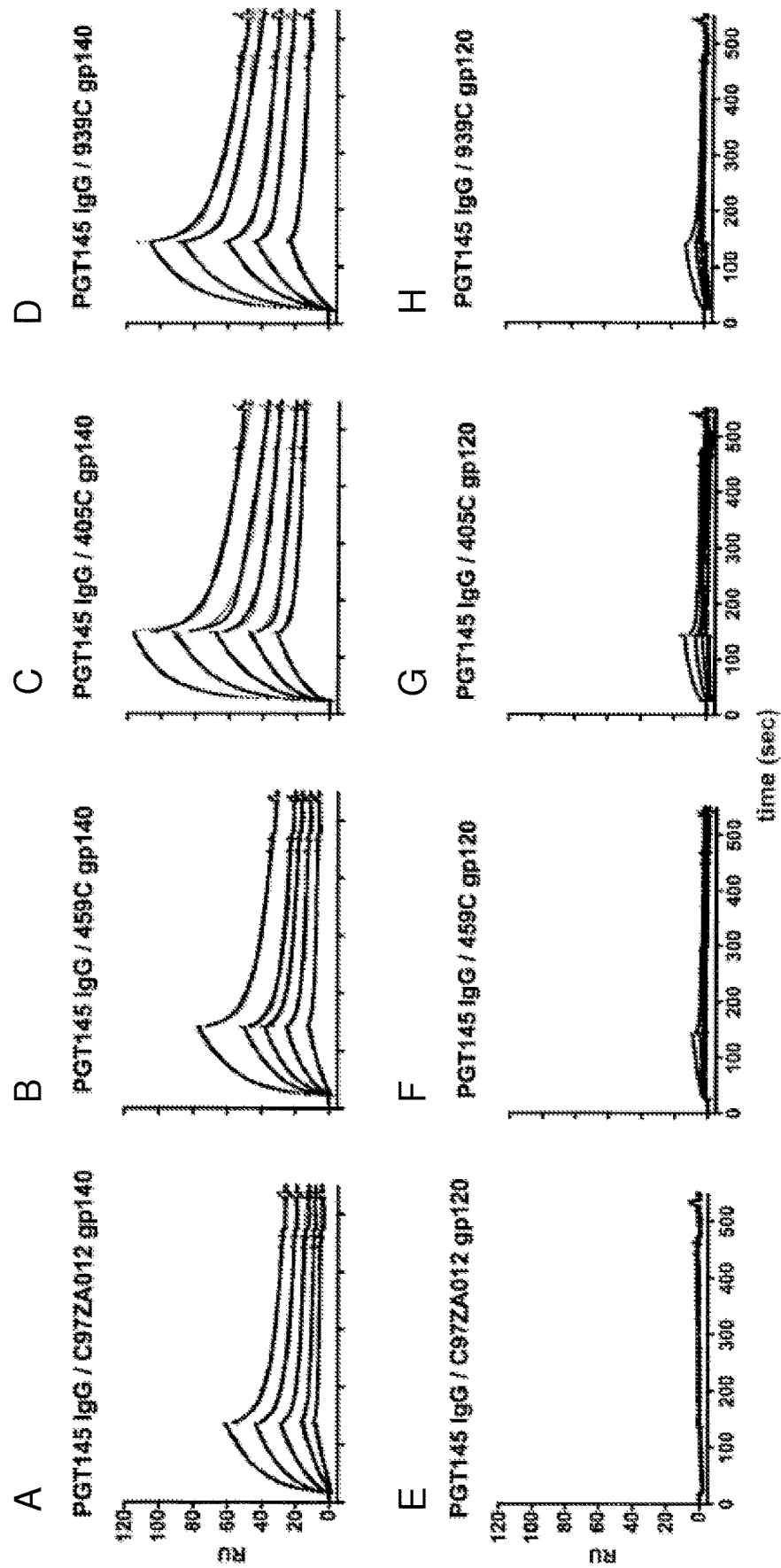
FIGS. 18A-18H are graphs showing presentation of V1/V2, glycan-dependent, quaternary-preferring epitopes by acute, clade C trimers and monomers. For all experiments, protein A was irreversibly coupled to a CM5 chip and IgGs were captured. 459C, 405C, and 939C trimers (FIGS. 18A-18D) and monomers (FIGS. 18E-18H) were flowed over bound PGT145 IgG at concentrations of 62.5-1000 nM. Sensorgrams presented in black, kinetic fits in gray. RU, response units.

The quaternary structure of the acute, clade C gp140 trimers was assessed utilizing PGT145 IgG, which preferentially binds to intact trimers and targets variable loops 1 and 2 (V1/V2) and N-linked glycans in this region (Yasmeen et al., supra; McLellan et al., *Nature* 1-10, 2011). PGT145 bound all the Env gp140 trimers but exhibited essentially no binding to the sequence-matched gp120 monomers (FIG. 18). PG9 IgG (Walker et al., supra; Davenport et al., *Journal of Virology*, 2011; Julien et al., supra) similarly bound the Env gp140 trimers at a low magnitude but not the sequence-matched monomers. None of the trimers bound 4E10 IgG (Cardoso et al., *Immunity* 22:163-173, 2005) in SPR analyses despite the presence of the sequence by western blot analyses, suggesting that these epitopes are buried in the context of the folded trimer, as we have reported previously (Kovacs et al., supra; Nkolola et al., *Journal of Virology* 88:9538-9552, 2014).

Immunogenicity of Novel, Acute Clade C Trimers

Figure 19A:
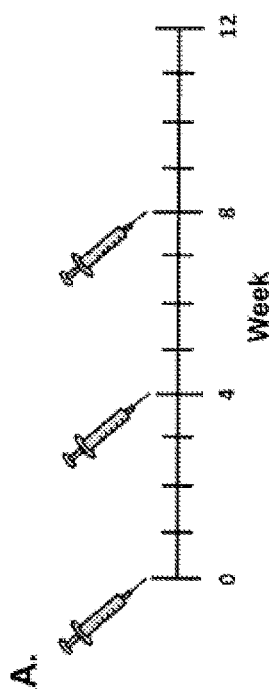
FIGS. 19A and 19B are diagrams and graphs showing binding antibody titers from guinea pigs vaccinated with clade C trimers.
Figure 19B:
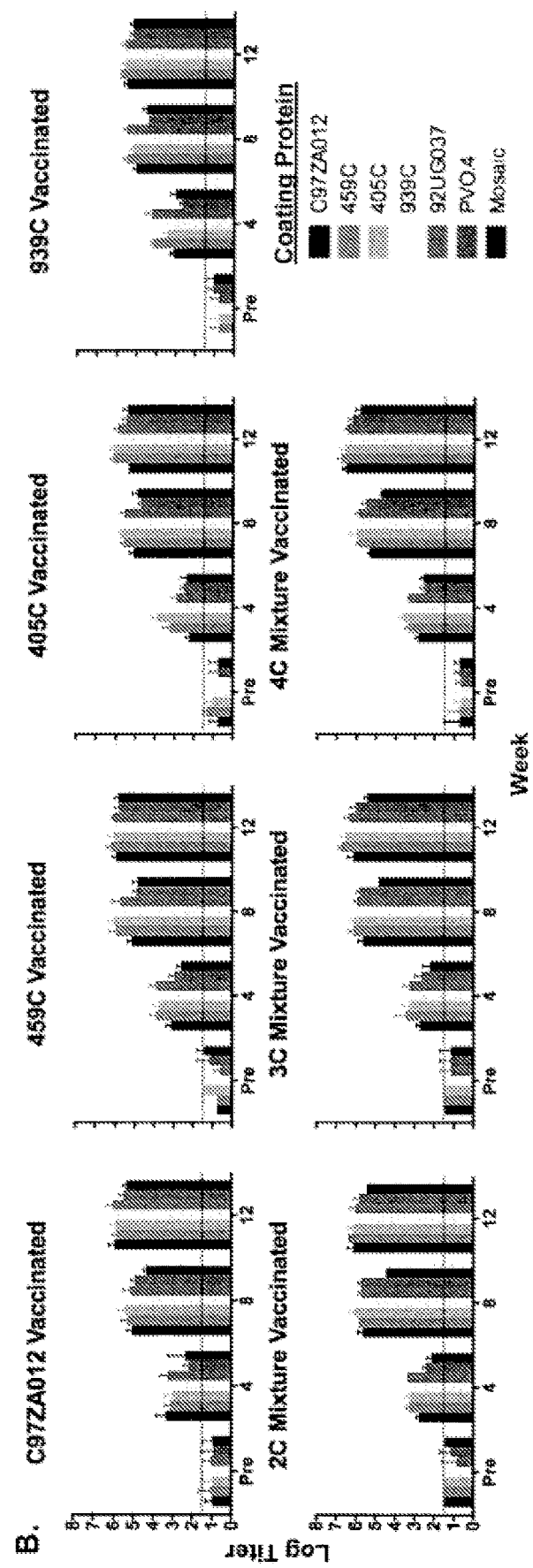

To assess the immunogenicity of our novel, acute clade C trimers, we immunized guinea pigs with trimers three times at monthly intervals, and animals were bled four weeks after each vaccination (FIG. 19A). Four groups of guinea pigs were vaccinated with the single Env trimers C97ZA012 (n=14), 459C (n=10), 405C (n=5), and 939C (n=5). Additionally, guinea pigs were vaccinated with multivalent trimer cocktails, including mixtures of two (2C; C97ZA012+459C) (n=5), three (3C; C97ZA012+459C+405C) (n=5), or four clade C trimers (4C; C97ZA012+459C+405C+939C) (n=10). Binding antibody responses were assessed by utilizing a panel of Envs as coating proteins from clade C (C97ZA012, 459C, 405C, and 939C), clade A (92UG037), clade B (PV0.4), and a mosaic (MosM) sequence. All guinea pigs developed similar magnitudes of antibody titers by ELISA (FIG. 19B). Animals showed low levels of binding antibodies after the first vaccination, which were boosted after the second vaccination, at which point the titers of binding antibodies largely plateaued. These data show that single immunogens and cocktails of immunogens developed high titer binding antibodies with similar kinetics and breadth.

Figure 20A:
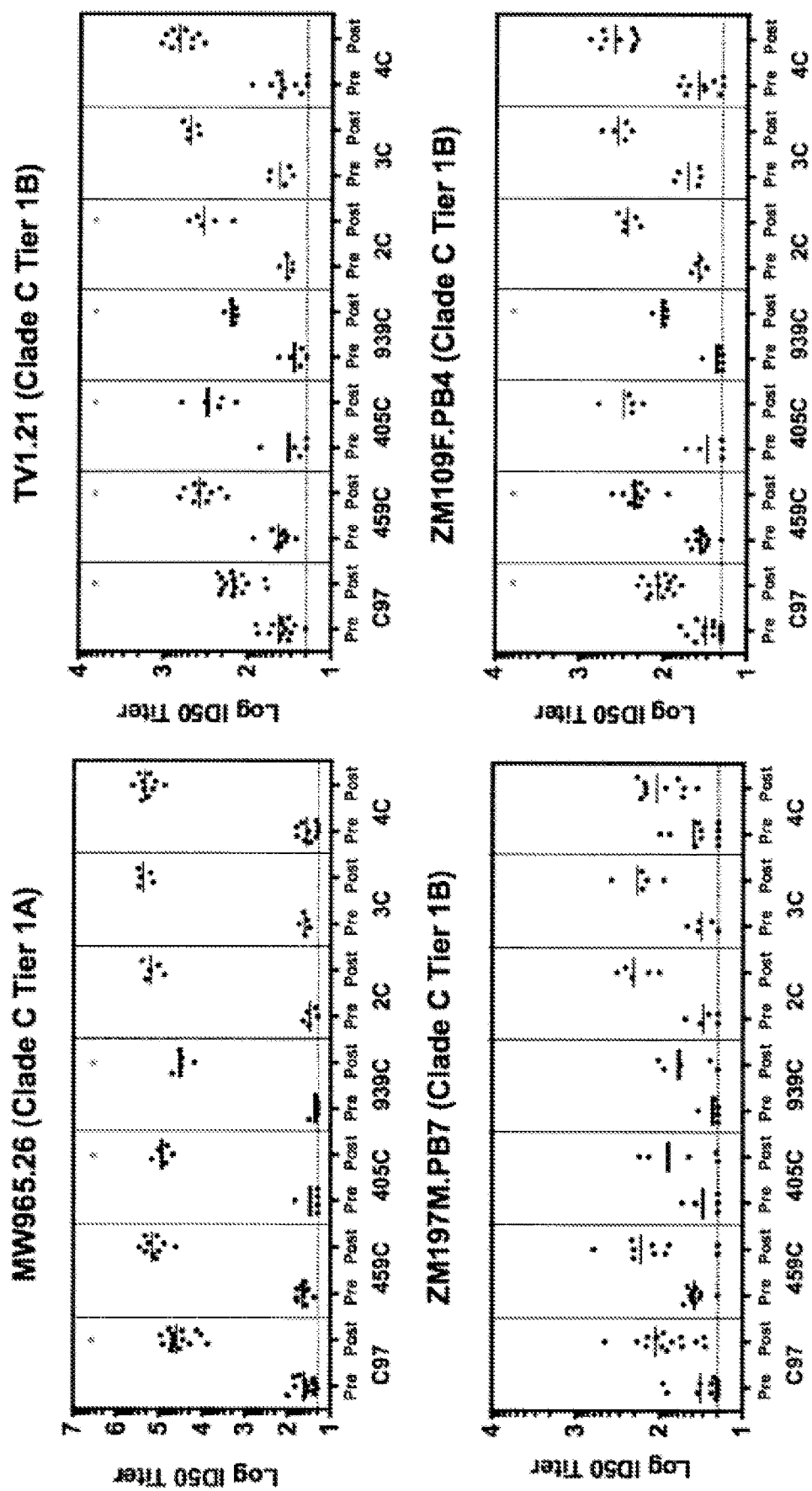
FIGS. 20A-20C are graphs showing magnitude of neutralizing antibody titers after vaccination with single clade C or multivalent vaccination regimens. Guinea pig sera obtained pre-vaccination (pre) and four weeks after the third vaccination were tested against a multi-clade panel of Tier 1 neutralization-sensitive isolates in the TZM.bl neutralization assay.

To determine the neutralization capacity of antibodies elicited by each of the novel trimers, a multi-clade panel of Tier 1A and 1B pseudovirions was utilized in the TZM.bl neutralization assay. Against clade C pseudovirions, guinea pigs vaccinated with Env 459C and 405C gp140 trended towards eliciting a greater magnitude of NAbs than Env C97ZA012 or 939C gp140 alone (FIG. 20A). Env 459C gp140 was the only trimer to elicit consistently positive NAbs against the 6535.3 pseudovirion. By Wilcoxon rank-sum tests, animals vaccinated with Env 459C gp140 elicited a statistically superior magnitude of neutralizing antibodies compared to Env 405C gp140 (cutoff 1=0.0034; cutoff 2=0.0105, as defined in the methods) and 405C elicited a superior magnitude of neutralizing antibodies when compared to Env 939C or C97ZA012 gp140s alone (cutoff 1=0.0007; cutoff 2=0.0105; cutoff 1=0.00081; cutoff 2=0.00061, respectively) (FIG. 21A; Table 5). A generalized linear model further supported the finding that guinea pigs vaccinated with Env 459C gp140 elicited a superior magnitude of neutralizing antibodies against the multiclade panel of pseudovirions than any other single trimer tested (FIG. 21B; Table 6). In particular, Env 459C gp140 exhibited the greatest neutralization advantage against clade B pseudovirions, possibly due to a region of the V3 loop that closely resembled the sequence of V3 in the clade B pseudovirions.

TABLE 5

Statistical comparison of vaccination regimens

| Test | Comparison | Cutoff 1: Post-Pre | Cutoff 2: Post-3*Pre |
|---|---|---|---|
| Friedman | 5 vaccines (including Quad) | P = 2.717e−07 | 4.456e−06 |
| Friedman | 4 vaccines (excluding Quad) | P = 1.402e−05 | 0.0004837 |
| Wilcoxon | 459C < Quad | P = 0.0024 | 0.0034 |
| Wilcoxon | 459C > 405C | P = 0.0034 | 0.0105 |
| Wilcoxon | 459C > C97Z | P = 0.0002 | 0.0005 |
| Wilcoxon | 459C > 939C | P = 0.0002 | 0.0002 |
| Wilcoxon | 405C > C97Z | P = 0.0081 | 0.0001 |
| Wilcoxon | 405C > 939C | P = 0.0007 | 0.0105 |

Figure 20B:
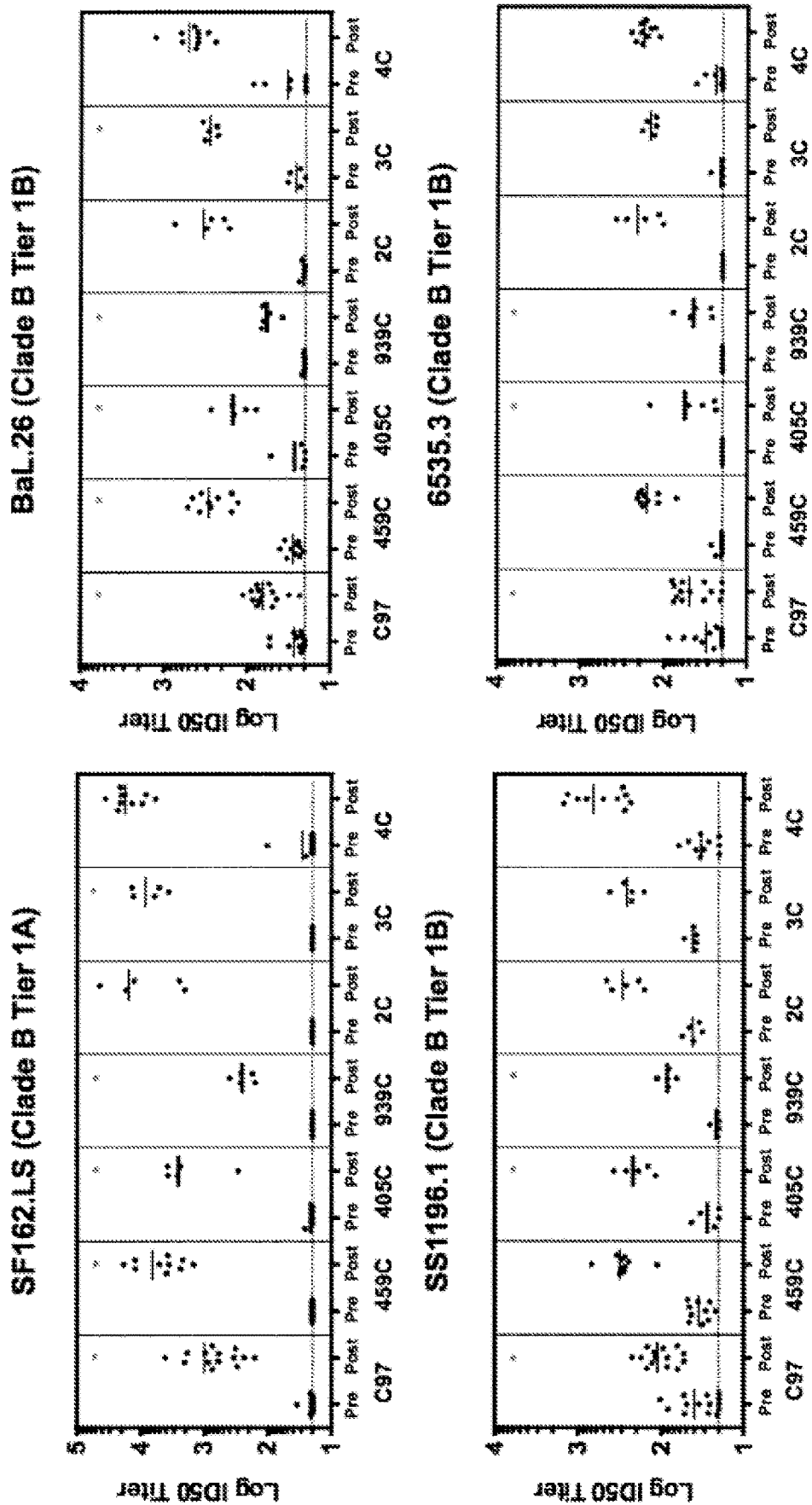
Figure 20C:
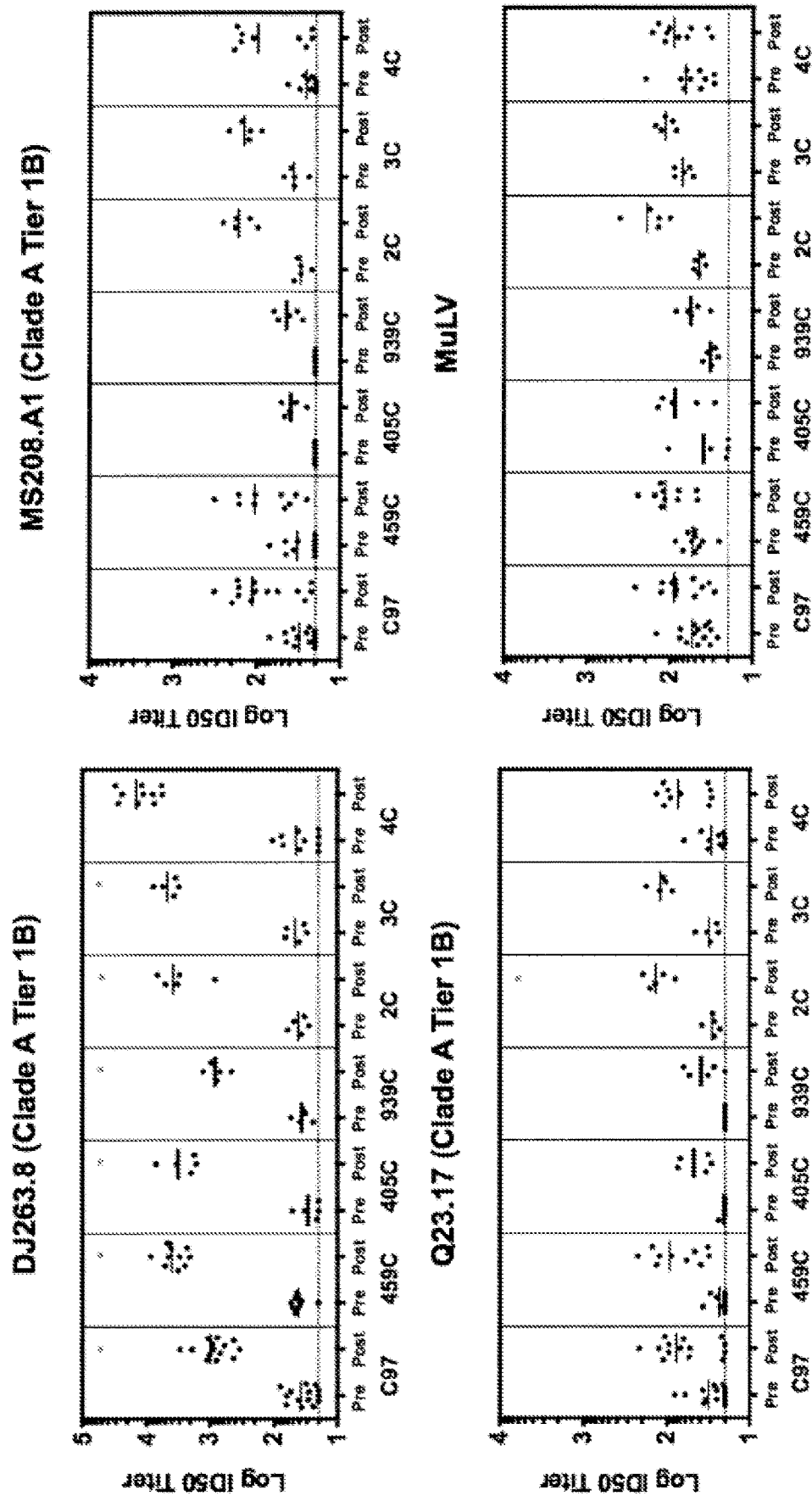

For the mixtures of trimers, there was a trend toward an increased magnitude of NAbs as each additional component was added to the mixture, suggesting that the unique antigenic properties of each trimer may contribute to the increased NAbs (FIG. 20A-20C). In particular, against DJ263.8, the quadrivalent mixture of trimers was significantly superior to all other monovalent and multivalent vaccination regimens tested (Mann-Whitney U, p<0.05). Moreover, the quadrivalent mixture of clade C trimers was superior to any of the single trimers alone against TV1.21, SF162.LS, BaL.26, and DJ263.8 (Mann-Whitney U, p<0.05) and showed similar trends against MW965.26, ZM109F.PB4, SS1196.1, and 6535.3. These data show that single clade C trimers and cocktails containing mixtures of clade C trimers can be used to neutralize HIV, with the mixtures exhibiting better neutralization characteristics.

To further evaluate the differences in NAbs elicited by each individual clade C trimer as compared to the quadrivalent mixture of clade C trimers, we grouped animals by vaccination regimen and compared the mean magnitude of neutralization obtained for each pseudovirion. We found that all groups exhibited statistical differences from each other (Friedman test, cutoff 1=2.717e-07; cutoff 2=4.456e-06) (Table 5) with the quadrivalent 4C mixture eliciting the greatest magnitude of neutralizing antibodies compared to 459C, which elicited the greatest magnitude of neutralizing antibodies compared to all other single immunogens (Wilcoxon rank sum, cutoff 1=0.0024; cutoff 2=0.0034) (FIG. 21A; Table 6). Additionally, by generalized linear model analysis, we found that the 4C mixture was superior to all monovalent vaccination regimens against clade A, B, and C pseudovirions, with the greatest advantage against clade B pseudovirions (FIG. 21B; Table 6). By heat map analysis of neutralization magnitude, 459C and 4C vaccinated animals tended to cluster together, C97ZA012 and 939C vaccinated animals tended to cluster together, and 405C vaccinated animals were spread throughout these two clusters (FIG. 21C). These data imply that 459C helps to drive the neutralization advantage observed in the 4C mixture but that other components also contribute. These neutralization data show that multivalent mixtures of trimeric HIV-1 Env immunogens can be used to increase the magnitude of NAb in vaccinated guinea pigs, and would be expected to provide similar results in the context of human therapy.

Discussion

In this study, we report the generation and characterization of three novel, acute clade C HIV-1 Env gp140 trimers. All trimers proved relatively stable and homogenous, and phylogenetic data suggested that Env 459C gp140 was the most central sequence. Antigenicity studies similarly demonstrated that Env 459C gp140 bound to a larger number of bNAbs than the other trimers. While all single and multivalent combinations of Env immunogens raised similar titers of binding antibodies, the cocktail containing all four clade C trimers was capable of eliciting a greater magnitude NAbs than any individual component and any other vaccination regimen tested. These data suggest an immunological advantage to a cocktail of antigenically diverse Envs.

Developing bNAbs remains an elusive goal of the HIV vaccine field, and several strategies have been utilized to increase the magnitude and/or breadth of NAbs through vaccination. These strategies include the use of centralized (consensus or ancestral) immunogens and the use of multivalent cocktails of immunogens. While centralized immunogens proved capable of eliciting NAb of modest magnitude and breadth, they did not possess any distinct neutralization advantage over single wild type immunogens (Liao et al., supra; Liao et al., supra; Kothe et al., supra; Kothe et al., supra; Gao et al., *Journal of Virology* 79:1154-1163, 2004). A distinct strategy is the utilization of cocktails of Env immunogens. Most prior studies have utilized cocktails of HIV Envs from different clades. In the present study, we found that a cocktail of all clade C immunogens increased the overall magnitude of NAbs. We also observed a neutralization benefit in utilizing this mixture, although neutralization using individual components alone was also robust. These data show the benefits of utilizing individual and multivalent cocktails of soluble, stable, well-formed HIV Env trimers in HIV therapy. Each of the trimers raises a unique, complementary repertoire of neutralizing antibodies.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

TABLE 6

Comparison of magnitude of response by generalized linear model with Gaussian distribution

| Clade | C97 Vaccination | 405C Vaccination | 939C Vaccination | 4C Vaccination |
|---|---|---|---|---|
| Cutoff 1: Post-Pre | | | | |
| A | 0.51 | 0.58 | 0.36 | 1.21 |
| B | 0.19 | 0.45 | 0.17 | 1.84 |
| C | 0.49 | 0.84 | 0.41 | 1.42 |
| Cutoff 1: Post-Pre*3 | | | | |
| A | 0.44 | 0.44 | 0.37 | 1.23 |
| B | 0.10 | 0.33 | 0.11 | 1.84 |
| C | 0.36 | 1.05 | 0.43 | 1.62 |

The invention claimed is:

1. An immunogenic composition comprising a gp140 polypeptide, wherein the polypeptide comprises:
   (a) at least 90% sequence identity over the entire length of SEQ ID NO: 1 and has a V1/V2 epitope corresponding to amino acids 166-183 of SEQ ID NO: 1 and a V3 epitope corresponding to amino acids 342-348 of SEQ ID NO: 1;
   (b) at least 90% sequence identity over the entire length of SEQ ID NO: 2 and has a V1/V2 epitope corresponding to amino acids 155-172 of SEQ ID NO: 2 and a V3 epitope corresponding to amino acids 330-335 of SEQ ID NO: 2; or
   (c) at least 90% sequence identity over the entire length of SEQ ID NO: 3 and has a V1/V2 epitope corresponding to amino acids 150-167 of SEQ ID NO: 3 and a V3 epitope corresponding to amino acids 328-334 of SEQ ID NO: 3;
   wherein the polypeptide is capable of inducing a neutralizing antibody response.

2. The immunogenic composition of claim 1 comprising a stabilized trimer of the gp140 polypeptide, wherein each of the gp140 polypeptides of the stabilized trimer has the same amino acid sequence.

3. The immunogenic composition of claim 2 comprising at least two different stabilized trimers.

4. The immunogenic composition of claim 2, wherein the amino acid sequence of each of the gp140 polypeptides of the stabilized trimer has at least 95% sequence identity over the entire length of any one of SEQ ID NOs: 1, 2, and 3.

5. The immunogenic composition of claim 2, wherein said composition further comprises a stabilized C97ZA012 gp140 trimer.

6. The immunogenic composition of claim 1, further comprising: (i) a pharmaceutically acceptable carrier, excipient, or diluent, and/or (ii) an adjuvant.

7. A kit comprising:
   (a) the immunogenic composition of claim 1;
   (b) a pharmaceutically acceptable carrier, excipient, or diluent; and
   (c) instructions for use thereof, wherein said kit optionally includes an adjuvant.

8. The immunogenic composition of claim 1, wherein the amino acid sequence of the gp140 polypeptide has at least 95% sequence identity over the entire length of SEQ ID NO: 1, 2, or 3.

9. The immunogenic composition of claim 8, wherein the amino acid sequence of the gp140 polypeptide comprises the amino acid sequence of SEQ ID NO: 1, 2, or 3.

10. The immunogenic composition of claim 4, wherein the amino acid sequence of each of the gp140 polypeptides of the stabilized trimer has at least 99% sequence identity over the entire length of any one of SEQ ID NOs: 1, 2, and 3.

11. The immunogenic composition of claim 10, wherein each of the gp140 polypeptides of the stabilized trimer comprises the amino acid sequence of any one of SEQ ID NOs: 1, 2, and 3.

12. The immunogenic composition of claim 8, wherein the amino acid sequence of the gp140 polypeptide has at least 99% sequence identity over the entire length of SEQ ID NO: 1, 2, or 3.

13. The immunogenic composition of claim 1, wherein the polypeptide of (a) further comprises one or more of amino acids 121-128, 287-295, 375-386, 434-441, 462-468, or 478-486 of SEQ ID NO: 1.

14. The immunogenic composition of claim 1, wherein the polypeptide of (b) further comprises one or more of amino acids 121-128, 275-283, 361-372, 408-415, 436-442, or 455-463 of SEQ ID NO: 2.

15. The immunogenic composition of claim 1, wherein the polypeptide of (c) further comprises one or more of amino acids 121-128, 273-281, 361-372, 419-426, 447-453, or 466-474 of SEQ ID NO: 3.

16. The immunogenic composition of claim 1, wherein the polypeptide of (a) further comprises amino acids 121-128, 287-295, 375-386, 434-441, 462-468, and 478-486 of SEQ ID NO: 1.

17. The immunogenic composition of claim 1, wherein the polypeptide of (b) further comprises amino acids 121-128, 275-283, 361-372, 408-415, 436-442, and 455-463 of SEQ ID NO: 2.

18. The immunogenic composition of claim 1, wherein the polypeptide of (c) further comprises amino acids 121-128, 273-281, 361-372, 419-426, 447-453, and 466-474 of SEQ ID NO: 3.

* * * * *